(12) United States Patent
Bartkovitz et al.

(10) Patent No.: US 8,088,815 B2
(45) Date of Patent: Jan. 3, 2012

(54) SPIROINDOLINONE PYRROLIDINES

(75) Inventors: David Joseph Bartkovitz, Nutley, NJ (US); Xin-Jie Chu, Livingston, NJ (US); Qingjie Ding, Bridgewater, NJ (US); Bradford James Graves, Nutley, NJ (US); Nan Jiang, Pine Brook, NJ (US); Jing Zhang, Parsippany, NJ (US); Zhuming Zhang, Hillsborough, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/939,234

(22) Filed: Nov. 4, 2010

(65) Prior Publication Data

US 2011/0130398 A1    Jun. 2, 2011

Related U.S. Application Data

(60) Provisional application No. 61/388,054, filed on Sep. 30, 2010, provisional application No. 61/265,792, filed on Dec. 2, 2009.

(51) Int. Cl.
*A61K 31/4015* (2006.01)
*C07D 487/10* (2006.01)

(52) U.S. Cl. ........................ 514/409; 548/410

(58) Field of Classification Search .................. 548/410; 514/409

See application file for complete search history.

(56) References Cited

U.S. PATENT DOCUMENTS

| | | | |
|---|---|---|---|
| 2,759,935 A | 8/1956 | Speeter | |
| 3,441,570 A | 4/1969 | Meyer | |
| 3,686,210 A | 8/1972 | Bell | |
| 4,020,179 A | 4/1977 | Irvine | |
| 6,511,974 B1 | 1/2003 | Dusza et al. | |
| 6,774,132 B1 | 8/2004 | Claesson et al. | |
| 7,495,007 B2 | 2/2009 | Chen et al. | |
| 7,553,833 B2 | 6/2009 | Liu et al. | |
| 7,638,548 B2 | 12/2009 | Liu et al. | |
| 2008/0009486 A1 | 1/2008 | Chen et al. | |
| 2008/0114013 A1 | 5/2008 | Liu et al. | |
| 2010/0075948 A1 | 3/2010 | Ding et al. | |
| 2011/0112052 A1* | 5/2011 | Wang et al. ........... | 514/81 |

FOREIGN PATENT DOCUMENTS

| | | |
|---|---|---|
| EP | 0288847 | 4/1988 |
| EP | 0947511 | 10/1999 |
| JP | 55 129284 | 6/1980 |
| JP | 2000191661 | 7/2000 |
| WO | 97/15556 | 5/1997 |
| WO | 98/54167 | 12/1998 |
| WO | 00/15657 | 3/2000 |
| WO | 00/71129 | 11/2000 |
| WO | 01/05790 | 1/2001 |
| WO | 03/008407 | 1/2003 |
| WO | 03/078394 | 9/2003 |
| WO | 2006/080574 | 8/2006 |
| WO | 2006091646 | 8/2006 |
| WO | 2006/136606 | 12/2006 |
| WO | 2007104664 | 9/2007 |
| WO | 2007104714 | 9/2007 |
| WO | 2008036168 | 3/2008 |
| WO | 2008/055812 | 5/2008 |
| WO | 2008080822 | 7/2008 |
| WO | 2008005268 | 10/2008 |
| WO | 2009080488 | 7/2009 |

OTHER PUBLICATIONS

Simplicio, Ana, Molecules 2008. 519-547.
Sairim, Carbohydrate Research 338_2003_303-306.
Sun, Cancer Biology & Therapy (2008) 7 (6), 845-852.
Ansel et al., Pharmaceutical Dosage Forms and Drug Delivery Systems (6th Ed. 1995) at pp. 196.
Ansel et al., Pharmaceutical Dosage Forms and Drug Delivery Systems (6th Ed. 1995) at p. 456-457.
Kraynack, E. A.; Dalgard, J. E.; Gaeta, F. C. A. Tetrahedron Letters, 1998, 39, 7679-7682.
Elliott, I. W.; Rivers, P. J. Org. Chem. 1964, 29, 2438-2440.
Andreani, A.; et al., Eur. J. Med. Chem. 1990, 25, 187-190.
Christopher Hulme, et al., Bioorganic & Medicinal Chemistry Letters, vol. 8, pp. 175-178 (1998), XP002405133.
F.D. Dopp, et al., J. Heterocyclic Chem., vol. 17, No. 9, pp. 1329-1330 (1980), XP002405134.
Gordon N. Walker, et al., J. Med. Chem., vol. 8, pp. 626-637 (1965), XP002405135.
Stanislav Kafka, et al., J. Org. Chem., vol. 66, pp. 6394-6399 (2001), XP002405136.
Amarnath Natarajan, et al., J. Med. Chem., vol. 47, pp. 1882-1885 (2004), XP002405137.
James C. Powers, J. Org. Chem., vol. 30, pp. 2534-2540 (1965), XP002405138.
Sengodagounder Muthusamy, et al., Synlett, vol. 2002, No. 11, pp. 1783-1786 (2002), XP002405139.
Ward C. Sumpter, J. Am. Chem Soc., vol. 54, pp. 2917-2918 (1932), XP002405141.

(Continued)

*Primary Examiner* — Andrew D Kosar
*Assistant Examiner* — Karen Cheng
(74) *Attorney, Agent, or Firm* — George W. Johnson; Patricia S. Rocha-Tramaloni

(57) ABSTRACT

There are provided compounds of the formula

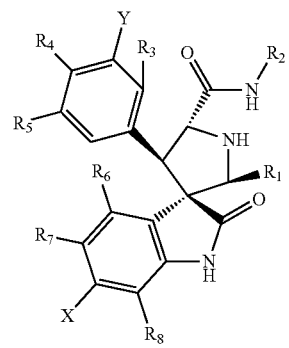

wherein X, Y and $R_1$ to $R_8$ are described herein along with the enantiomers, pharmaceutically acceptable salts and esters thereof. The compounds are useful as anticancer agents.

22 Claims, No Drawings

OTHER PUBLICATIONS

H.E. Zaugg, et al., J. Am. Chem. Soc., vol. 84, pp. 4574-4578 (1962), XP002418406.
Steven P. Govek, et al., J. Am. Chem. Soc., vol. 123, pp. 9468-9469 (2001), XP002418407.
Rita Kapiller-Dezofi, et al., New J. Chem., vol. 28, pp. 1214-1220 (2004), XP002418408.
David W. Robertson, et al., J. Med. Chem., vol. 29, pp. 1832-1840 (1986), XP002418409.
Kazuo Takayama, et al., Tetrahedron Letters, vol. 5, pp. 365-368 (1973), XP002418410.
Audris Huang, et al., J. Am. Chem. Soc., vol. 126, pp. 14043-14053 (2004), XP002418411.
Masaru Ogata, et al., Eur. J. Med. Chem.—Chimica Therapeutica, vol. 16, No. 4, pp. 373-379 (1981), XP00907847.
Istvan Moldvai, et al., Arch. Pharm. Pharm. Med. Chem., vol. 329, pp. 541-549 (1996), XP009078456.
Hossein Pajouheish, et al., J. Pharm. Sci., vol. 72, No. 3, pp. 318-321 (1983), XP009078411.
Krishna C. Joshi, et al., Journal of Fluorine Chemistry, vol. 44, pp. 59-72 (1989), XP002418412.
Piyasena Hewawasam, et al., Bioorganic & Medicinal Chemistry Letters, vol. 12, pp. 1023-1026 (2002), XP002418413.
Santiago Barroso, et al., J. Org., Chem., vol. 69, pp. 6821-6829 (2004), XP002418416.
Paul Aeberli, et al., J. Org. Chem., vol. 33, No. 4 pp. 1640-1643 (1968), XP002418417.
A. Walser, et al., J. Org. Chem., vol. 38, No. 3, pp. 449-456 (1973), XP002418418.
Javad Azizian, et al., Synthesis, vol. 2005, No. 7, pp. 1095-1098 (2005), XP 002418427.
Andrew Fensome, et al., Bioorganic & Medicinal Chemistry Letters, vol. 12, pp. 3487-3490 (2002), XP002418428.
T.V. Rajanbabu, et al., J. Org. Chem., vol. 51, pp. 1704-1712 (1986), XP002418429.
Karnail S. Atwal, et al., J. Med. Chem., vol. 39, pp. 304-313 (1996), XP002418430.
Balazs Volk, et al., Eur. J. Org. Chem., pp. 3991-3996 (2003), XP002418431.
Keith Smith, et al., J. Chem. Soc. Perkin Trans. 1, vol. 1999, pp. 2299-2303 (1999), XP002418432.
R.L. Hinman, et al., J. Org. Chem., vol. 29, pp. 2431-2437 (1964), XP002418433.
J. Amer. Chem. Soc (2005) 127 PG. 10130.
Hellmann, H. et al, Chemische Berichte, ISSN:009-2440, vol. 86, 1346-1361 (1953) XP002481520.
Dhigemori, H. et al, Che. Abstracts Service XP002481522.
Alarcon-Vargas, D et al, Carcinogenesis, 23(4):541-547 (2002) XP002481521.
Arndt, Hans-Dieter, Kleine Molekule pp. 4664-4673—XP-002465843.
Lippa, Blaise, Bioorganic & Medicinal Chemistry Letters 18, (2008) 3359-3363.
Ding, Journal of Medicinal Chemistry (2006), 49(12), 3432-3435.
Chosez, L., Tetrahedron, (1995) 11021-11042.
Ashimori A. Journal of Organic Chem 57: 17 (2002) 4571-4572 XP002527583.
Ashimori A. Journal of American Chem Society 120 (1998) 6477-6477-6487 XP001038246.
Johnson R.S., Journal of American Chem Society (1900) 796-800 xp002156747.
Ding, Tetrahedron Letters (2005), 46 (35), 5949-5951SUN.
Shangary, Molecular Cancer Therapeutics (2008), 7(6) 1533-1542.
Shangary, Proceedings of National Academy of Science (2008) 105(10) 3933-3938.
Saddler, Blood (2008), 111(3), 1584-1593.
Yu, J. Med. Chem. 52:24, 7970-7973 (2009).
Alemparte, Organic Letters, 7:21 4569-4579 (2005).
International Search Report for PCT/EP210/068353 dated Mar. 25, 2011.

* cited by examiner

SPIROINDOLINONE PYRROLIDINES

PRIORITY TO RELATED APPLICATION(S)

This application claims the benefit of U.S. Provisional Application No. 61/388,054, filed Sep. 30, 2010, and U.S. Provisional Application No. 61/265,792, filed Dec. 2, 2009, which is hereby incorporated by reference in its entirety.

SUMMARY OF THE INVENTION

The present invention relates to spiroindolinone pyrrolidines I which act as antagonists of mdm2 interactions and hence are useful as potent and selective anticancer agents. The present compounds are of the general formula

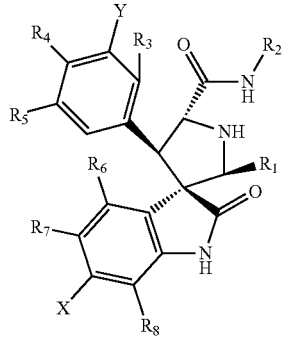

I wherein X, Y and $R_1$ to $R_8$ are as described herein and the enantiomers and pharmaceutically acceptable salts thereof.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis: p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

DETAILED DESCRIPTION OF THE INVENTION

The present invention relates to pyrrolidine-2-carboxamide derivatives I which act as antagonists of mdm2 interactions and hence are useful as potent and selective anticancer agents. The present compounds are of the general formula

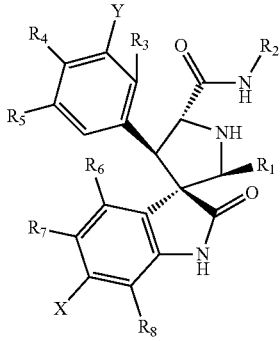

I wherein
X is selected from the group consisting of F, Cl, and Br;
Y is selected from the group consisting of F, Cl, and Br;
$R_1$ is a substituted lower alkyl selected from

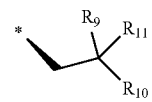

where $R_9$, $R_{10}$ are both methyl, or linked to form a cyclopropyl, cyclobutyl, cyclopentyl or cyclohexyl group;
$R_{11}$ is $(CH_2)_q$—$R_{12}$;
$R_{12}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle;
q is 0, 1 or 2;
$R_2$ is selected from the group consisting of aryl, substituted aryl, heteroaryl and substituted heteroaryl;
$R_3$, $R_4$, $R_5$ is selected from H or F with the proviso that at least two of $R_3$, $R_4$, $R_5$ are hydrogen;
$R_6$, $R_7$, $R_8$ is selected from H or F with the proviso that at least two of $R_6$, $R_7$, $R_8$ are hydrogen and the pharmaceutically acceptable salts and enantiomers thereof.
More preferred are compounds of the formula II

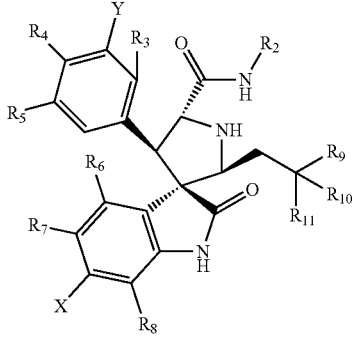

II wherein,

X is selected from F, Cl or Br;

Y is selected from F, Cl or Br;

$R_9$, $R_{10}$ are both methyl, or linked to form a cyclopropyl, cyclobutyl, cyclopentyl or cyclohexyl group;

$R_{11}$ is selected from hydrogen, methyl, ethyl, hydroxymethyl, 2-hydroxylethyl, hydroxycarbonyl, methoxycarbonyl, 2-methoxyethyl, isopropyl, cyclopropyl, 4-pyranyl, substituted 4-piperidinyl, substituted phenyl, substituted benzyl or substituted 2-furanyl;

$R_2$ is selected from the group consisting of aryl, substituted aryl, heteroaryl and substituted heteroaryl having the formulas

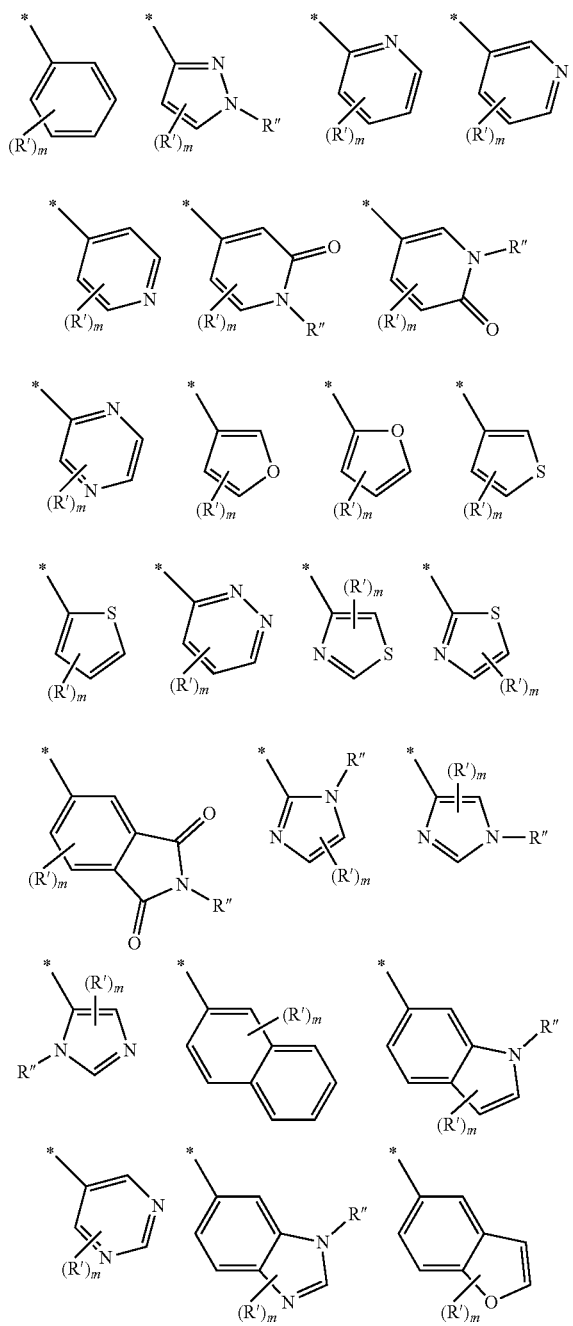

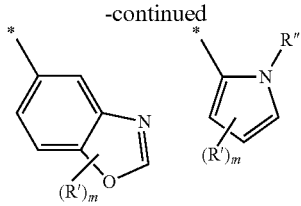

R' is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, $NH_2$, N(H, lower-alkyl) or N(lower-alkyl)$_2$, R" is one group selected from the group consisting of hydrogen, lower alkyl, lower-alkenyl, lower-alkynyl, hydroxy, CN, $CF_3$, aminocarbonyl, carboxy, lower-alkoxy, thio-lower-alkoxy, lower-alkylsulfonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, $NH_2$, N(H, lower-alkyl) or N(lower-alkyl)$_2$, m=1-5, $R_3$, $R_4$, $R_5$ is selected from H or F with the proviso that at least two of $R_3$, $R_4$, $R_5$ are hydrogen;

$R_6$, $R_7$, $R_8$ is selected from H or F with the proviso that at least two of $R_6$, $R_7$, $R_8$ are hydrogen and the pharmaceutically acceptable salts and enantiomers thereof.

Further preferred are compounds of formula I in which

X is F, Cl or Br;

Y is F, Cl or Br;

$R_1$ is

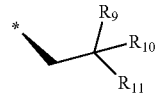

$R_9$, $R_{10}$, $R_{11}$ are methyl;

$R_2$ is selected from the group consisting of aryl, substituted aryl, heteroaryl and substituted heteroaryl having the formulas

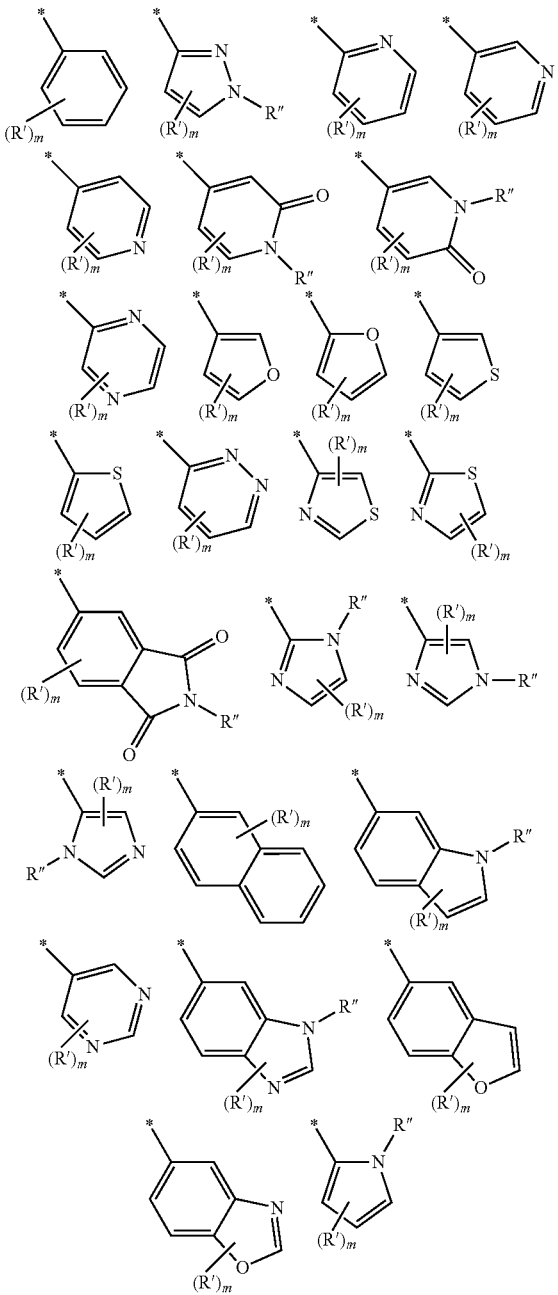

R' is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, $NH_2$, N(H, lower-alkyl) or N(lower-alkyl)$_2$, R" is selected from the group consisting of hydrogen, lower alkyl, lower-alkenyl, lower-alkynyl, hydroxy, CN, $CF_3$, aminocarbonyl, carboxy, lower-alkoxy, thio-lower-alkoxy, lower-alkylsulfonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, $NH_2$, N(H, lower-alkyl) or N(lower-alkyl)$_2$, m=1-3, $R_3$, $R_4$, $R_5$ is selected from H or F with the proviso that at least two of $R_3$, $R_4$, $R_5$ are hydrogen; and $R_6$, $R_7$, $R_8$ is selected from H or F with the proviso that at least two of $R_6$, $R_8$ are hydrogen and the pharmaceutically acceptable salts and esters and enantiomers thereof.

Further preferred are compounds of formula I in which

X is F, Cl or Br;

Y is F, Cl or Br;

$R_1$ is

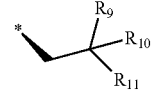

$R_9$, $R_{10}$, $R_{11}$ are methyl;

$R_2$ is selected from the group consisting of heteroaryl and substituted heteroaryl having the formulas

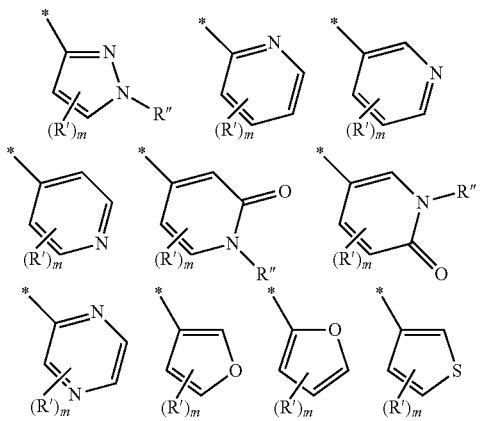

-continued

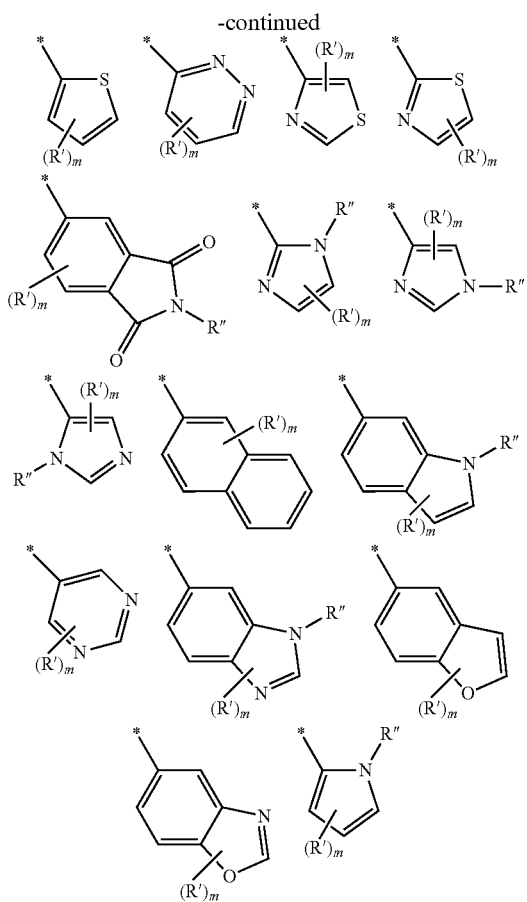

R' is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, N(H, lower-alkyl) or N(lower-alkyl)$_2$, R" is selected from the group consisting of hydrogen, lower alkyl, lower-alkenyl, lower-alkynyl, hydroxy, CN, $CF_3$, aminocarbonyl, carboxy, lower-alkoxy, thio-lower-alkoxy, lower-alkylsulfonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, $NH_2$, N(H, lower-alkyl) or N(lower-alkyl)$_2$, m=1-3, $R_3$, $R_4$, $R_5$ is selected from H or F with the proviso that at least two of $R_3$, $R_4$, $R_5$ are hydrogen; and $R_6$, $R_7$, $R_8$ is selected from H or F with the proviso that at least two of $R_6$, $R_7$, $R_8$ are hydrogen and the pharmaceutically acceptable salts and esters and enantiomers thereof.

Further preferred are compounds of formula I in which
X is F, Cl or Br;
Y is F, Cl or Br;
$R_1$ is

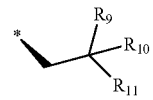

$R_9$, $R_{10}$, $R_{11}$ are methyl;
$R_2$ is a substituted phenyl of the formula

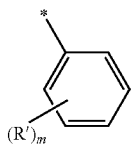

R' is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$, m=1-3, $R_3$, $R_4$, $R_5$ is selected from H or F with the proviso that at least two of $R_3$, $R_4$, $R_5$ are hydrogen;

$R_6$, $R_7$, $R_8$ is selected from H or F with the proviso that at least two of $R_6$, $R_7$, $R_8$ are hydrogen and the pharmaceutically acceptable salts and esters and enantiomers thereof.

Further preferred are compounds of formula I in which
X is F, Cl or Br;
Y is F, Cl or Br;
$R_1$ is

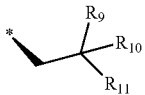

$R_9$, $R_{10}$, $R_{11}$ are methyl;
$R_2$ is a substituted phenyl of the formula

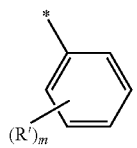

R' is selected from the group consisting of lower-alkenyl, lower-alkynyl, dioxo-lower-alkylene (forming e.g. a benzodioxyl group), hydroxy, CN, $CF_3$, aminocarbonyl, lower-alkylaminocarbonyl, carboxy, $NO_2$, thio-lower-alkoxy, lower-alkylsulfonyl, aminosulfonyl, lower-alkyl-carbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$,
m=1-3,
$R_3$, $R_4$, $R_5$ is selected from H or F with the proviso that at least two of $R_3$, $R_4$, $R_5$ are hydrogen;
$R_6$, $R_7$, $R_8$ is selected from H or F with the proviso that at least two of $R_6$, $R_7$, $R_8$ are hydrogen and the pharmaceutically acceptable salts and esters and enantiomers thereof.

Especially preferred are compounds selected from the group consisting of
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide,
rac-(2'S,3'R,4'S,5')-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide,
chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonyl-phenyl)-amide,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide,
chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-fluoro-phenyl)-amide,
rac-5-{[(2'S,3'R,4'S,5'R)-6-chloro-4'-(3-chloro-2-fluoro-phenyl)-2',2-dimethyl-propyl)-2-oxo-1,2-dihydro-spiro[indole-3,3'-pyrrolidine]-5'-carbonyl]amino}-thiophene-2-carboxylic acid methyl ester,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-benzoic acid methyl ester,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid,
chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide,
chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-chloro-phenyl)-amide,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide,
chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide,
rac-2-chloro-4-{[2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester,
rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-2-oxo-1,2-dihydro-pyridin-4-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1-propyl-1,2-dihydro-pyridin-4-yl)-amide, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid p-tolylamide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-methanesulfonyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-acetyl)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [1-(2-hydroxy-ethyl)-1H-pyrazol-3-yl]-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide,
rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide,
rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide,
rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide,
rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide,
rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-phenyl)-amide,
rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-phenyl)-amide,
acetic acid rac-3-[(2'S,3'R,4'S,5'R)-6-chloro-4'-(3-chloro-2-fluoro-phenyl)-5'-(4-cyano-phenylcarbamoyl)-2-oxo-1,2-dihydro-spiro[indole-3,3'-pyrrolidin]-2'-yl]-2,2-dimethyl-propyl ester,
rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid (4-cyano-phenyl)-amide,
rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid (4-carbamoyl-phenyl)-amide,
rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester,
rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]amino}-3-methoxy-benzoic acid,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid,
chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl-amino}-3-methoxy-benzoic acid,
rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-2-methoxy-phenyl)-amide,
rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-2-methoxy-phenyl)-amide,
rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide,
rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide,
rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-2-methoxy-phenyl)-amide,
rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide,
rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide,
rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide,
rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]-amino}-3-methoxy-benzoic acid methyl ester,
rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]amino}-3-methoxy-benzoic acid,
rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester,
rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid,
rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester,
rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid,
rac-4-{[(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester,
rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid methyl ester,
rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-ethoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-nitro-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-amino-2-methoxy-phenyl)-amide, rac-(2'S,3'R,4'S,511)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetylamino-2-methoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-2-methoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-morpholin-4-yl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2,6-dimethyl-morpholin-4-yl)-2-methoxy-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-trifluoromethoxy-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid phenylamide, chiral (2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide, rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester, rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-butoxy-4-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-tetrazol-1-yl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonylamino-2-methoxy-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(tetrahydro-pyran-4-yloxy)-phenyl]-amide, chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-phenyl)-acetic acid tert-butyl ester, chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-phenyl)-acetic acid, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethyl-2-methoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-methoxy-pyridin-4-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylamino-2-methoxy-phenyl)-amide, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methylamino-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methylamino-benzoic acid, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(2-methylsulfanyl-ethoxy)-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfonyl-ethoxy)-2-methoxy-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfinyl-ethoxy)-2-methoxy-phenyl]-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-phenyl)-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-2-methoxy-phenyl)-amide, rac-(2'S,3'R,4'S,512)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-2-methoxy-phenyl)-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid [4-(2-hydroxy-ethoxy)-2-methoxy-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(3-methanesulfonyl-propoxy)-2-methoxy-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-cyano-pyridin-3-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-carbamoyl-pyridin-3-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-cyano-pyrimidin-5-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-carbamoyl-pyrimidin-5-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [6-(2-hydroxy-ethoxy)-4-methoxy-pyridin-3-yl]-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-1-methyl-1H-pyrrole-2-carboxylic acid tert-butyl ester, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-1H-pyrrol-2-yl)-amide, rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid ethyl ester, rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-thiazol-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-pyridin-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-pyridin-2-yl)-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-furan-2-carboxylic acid methyl ester, acetic acid chiral 2-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-phenoxy)-ethyl ester, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-3-methoxy-phenyl]-amide, rac-(4-{[(2'S,3'R,4'S,512)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid methyl ester, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid, rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid methyl ester, rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-methoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-carbamoyl-ethyl-phenyl]-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzo[b]thiophene-2-carboxylic acid methyl ester, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzo[b]thiophene-2-carboxylic acid, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-fluoro-5-methoxy-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-fluoro-5-methoxy-benzoic acid, rac-(4-{[(2'S,3'R,4'S,5'R)-6-chloro-4'-(3-chloro-2-fluoro-phenyl)-2'-(2,2-dimethyl-propyl)-2-oxo-1,2-dihydrospiro[indole-3,3'-pyrrolidine]-5'-carbonyl]-amino}-phenylamino)-acetic acid ethyl ester, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenylamino)-acetic acid, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-acetic acid ethyl ester, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-acetic acid, chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid, chiral 3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid and chiral (2'S,3'R,4'S,5'R)-6-chloro-4'-(3-chloro-2-fluorophenyl)-N-(4-(cyanocarbamoyl)-2-methoxyphenyl)-2'-(2,2-dimethyl-propyl)-2-oxospiro[indoline-3,3'-pyrrolidine]-5'-carboxamide.

TERMS & DEFINITIONS

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carbamoyl, aminocarbonyl, carboxy lower alkoxy, oxo and CN. Preferred substituents for alkyl are alkoxy and N(lower alkyl)$_2$.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably, fluorine and chlorine.

"Aryl" means a monovalent, monocyclic or bicyclic, aromatic carbocyclic hydrocarbon preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both may be substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like.

Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formulas I and II as well as their salts that have at least one asymmetric carbon atom may be present as racemic mixtures or different stereoisomers. The various isomers can be isolated by known separation methods, e.g., chromatography.

Compounds disclosed herein and covered by formulas I and II above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The present invention provides novel methods for the synthesis of spiroindolinones of formulas I and II. Compounds of this invention can be synthesized according to the following general schemes. Suitable processes for synthesizing these compounds are provided in the examples.

Preparations of intermediates II and III are illustrated in Scheme 1 and 2. In general an appropriately selected aldehyde can be reacted with glycine tert-butyl ester to generate imine II and were used as a crude product (Scheme 1).

Scheme 1

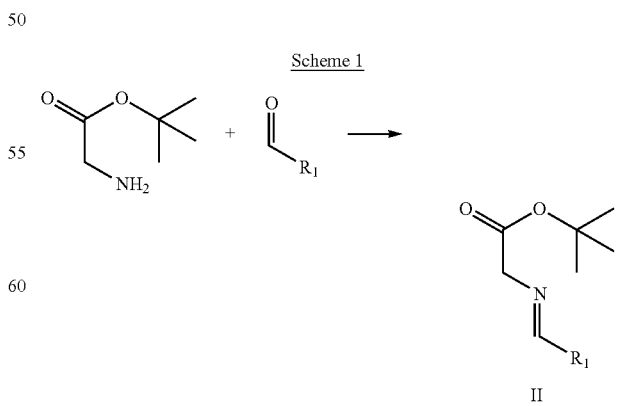

Reagents and conditions:
$CH_2Cl_2$, room temperature, 3 h

An intermediate of formula III can be made from a base-catalyzed condensation reaction of appropriately selected substituted 2-oxindole and substituted benzaldehyde in methanol. The choice of bases includes but is not limited to pyrrolidine or piperidine. The reaction generates III as a mixture of Z- and E-isomers with E-isomer as the major product.

Scheme 2

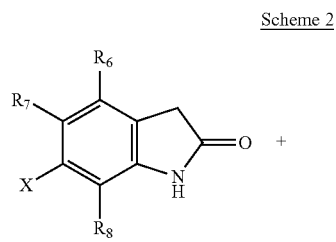

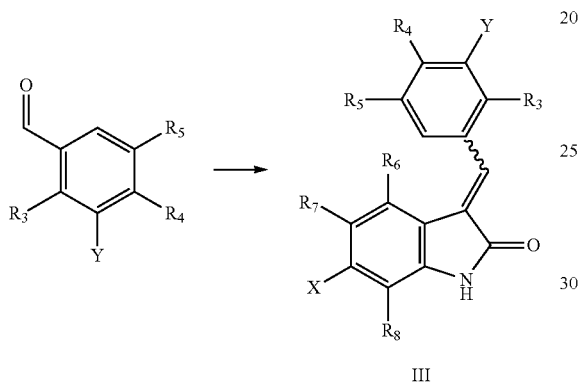

Reagents and conditions:
pyrrolidine or piperidine, MeOH, 50° C., 3 h

As illustrated in Scheme 3, spiroindolinones of formula IV and its enantiomer IV' as a racemic mixture can be made from intermediates II and III by the 1,3-dipolar cylcoaddition reaction mediated by lewis acid AgF and triethylamine, immediately followed by an isomerization reaction using DBU as the base in tert-butanol at an elevated temperature of 100° C. to 150° C. The [2+3] cycloaddition reactions of azomethine ylides 1,3-dipoles with olefinic dipolarphiles to form pyrrolidine ring formation have been described in published procedures including Jorgensen, K. A. et at (*Org. Lett.* 2005, Vol 7, No. 21, 4569-4572), Grigg, R. et al (*Tetrahedron*, 1992, Vol 48, No. 47, 10431-10442; *Tetrahedron*, 2002, Vol 58, 1719-1737), Schreiber, S. L. et al (*J. Am. Chem. Soc.*, 2003, 125, 10174-10175), and Carretero, J. C. et al (*Tetrahedron*, 2007, 63, 6587-6602). Racemic mixtures of compounds IV and IV' are subsequently converted to racemic mixture of acid V and V' by deprotection reaction using trifluoroacetic acid, followed by amide formation with various aryl or heteroaryl amines using diphenylphsphinic chloride as the coupling reagent to give the racemic mixture of compounds in formula I and I'. Finally, the racemic mixture of compounds I and I' can be chirally separated using chiral Super Fluid Chromatography (SFC) or chiral HPLC or chiral column chromatography to afford chirally pure or enriched compounds in formula I.

Scheme 3

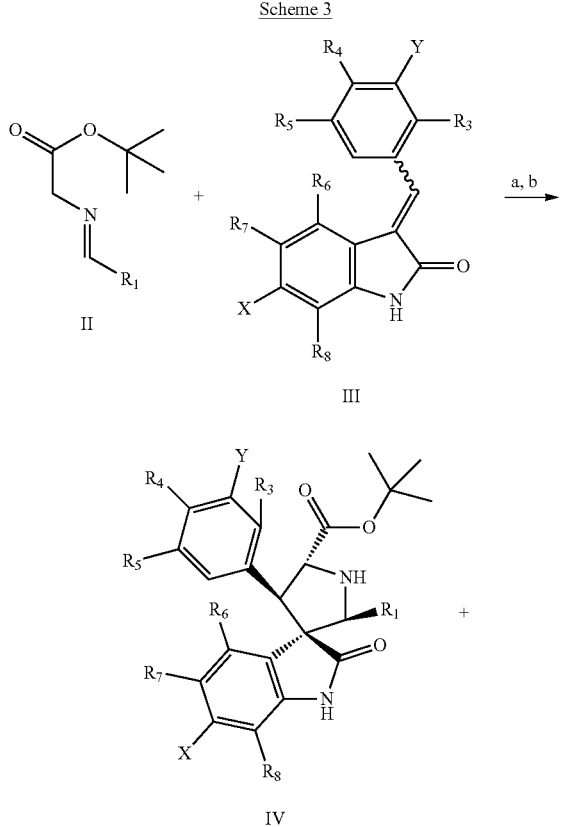

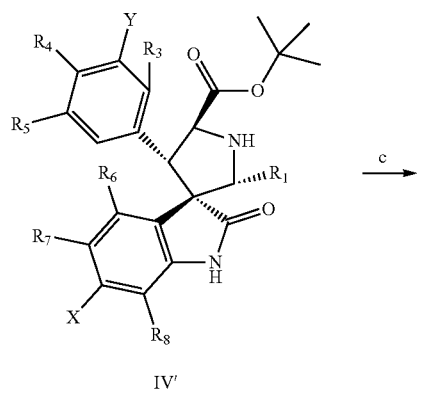

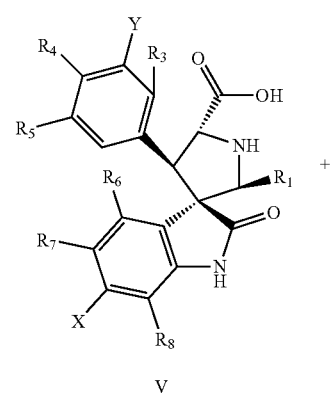

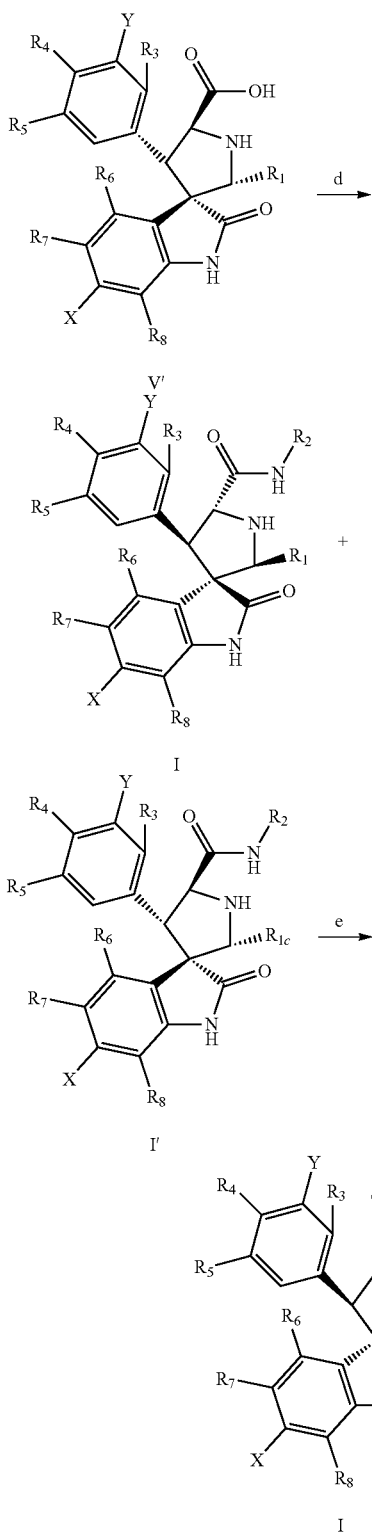

The racemic mixture of intermediates pair IV and IV', or V and V' can also be chirally separated using chiral Super Fluid Chromatography (SFC) or chiral HPLC or chiral column chromatography to their corresponding optically pure or enriched form IV or V. Intermediates IV or V can be converted into analogues I in a similar manner by following the synthetic routes outlined in Scheme 3 without any further chiral separations.

EXAMPLES

The compounds of the present invention may be synthesized according to novel techniques. The following examples and references are provided to aid the understanding of the present invention, the true scope of which is set forth in the appended claims.

Example 1

Preparation of intermediate [3,3-dimethyl-but-(E)-ylideneamino]-acetic acid tert-butyl ester

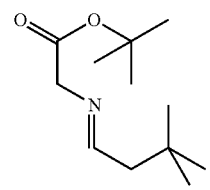

M.W. 213.32
$C_{12}H_{23}NO_2$

A mixture of glycine tert-butyl ester (Alfa) (2.71 g, 20.0 mmol) and 3,3-dimethyl-butyraldehyde (Alfa) (2.21 g, 21.0 mmol) in $CH_2Cl_2$ (50 mL) was stirred at rt overnight. The reaction mixture was concentrated and the residue was dried in vacuo to give [3,3-dimethyl-but-(E)-ylideneamino]-acetic acid tert-butyl ester (4.29 g, 100%) as colorless oil which was used in the next step without further purification.

Example 2

Preparation of intermediate E/Z-6-chloro-3-(3-chloro-2-fluoro-benzylidene)-1,3-dihydro-indol-2-one

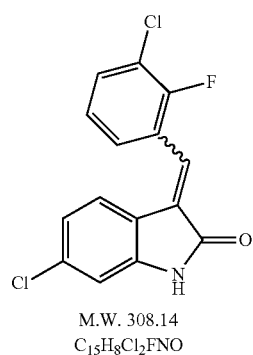

M.W. 308.14
$C_{15}H_8Cl_2FNO$

Reagents and conditions:
a. AgF, NEt₃, CH₂Cl₂ or ClCH₂CH₂Cl, rt, 18 h;
b. DBU, t-BuOH, 120° C., 2 h;
c. TFA, CH₂Cl₂, rt, 18 h;
d. NH₂R₂, diphenylphosphinic chloride, iPr₂NEt, CH₂Cl₂ or ClCH₂CH₂Cl, rt or 60° C., 18 h;
e. Chiral SFC separation To the mixture of 6-chloro-2-oxindole (11 g, 65.6 mmol) (Crescent) and 3-chloro-2-fluorobenzaldehyde (12 g, 75.7 mmol) (Aldrich) in methanol (140 mL) was added piperidine (5.59 g, 65.6 mmol) (Aldrich) dropwise. The mixture was then heated at 50° C. for 3 h. After cooled to 4° C., the mixture was filtered and resulting precipitate was collected, dried to give E/Z-6-chloro-3-(3-chloro-2-fluoro-benzylidene)-1,3-dihydro-indol-2-one as a yellow solid (Yield 18 g, 89%).

Example 3

Preparation of intermediate rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester

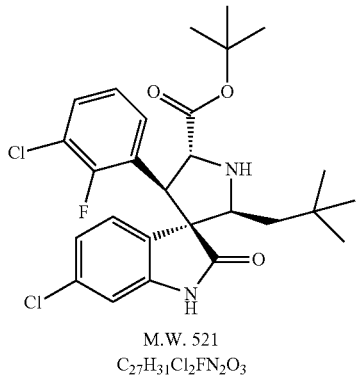

M.W. 521
$C_{27}H_{31}Cl_2FN_2O_3$

To a solution of [3,3-dimethyl-but-(E)-ylideneamino]-acetic acid tert-butyl ester (3.37 g, 15.8 mmol) prepared in Example 1 and E/Z-6-chloro-3-(3-chloro-2-fluoro-benzylidene)-1,3-dihydro-indol-2-one (4 g, 13 mmol) prepared in Example 2 in dichloromethane (100 mL) were added triethylamine (6.6 mL, 47.4 mmol) and AgF (2 g, 15.8 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into t-butanol (30 mL), and 1,8-diazabicyclo[5.4.0]undec-7-ene (DBU, Fluka) (7.2 g, 47.4 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (EtOAc:hexanes=1:3, 1:2) to give as rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester a white foam (2.7 g, 33%)

Example 4

Preparation of intermediate rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid

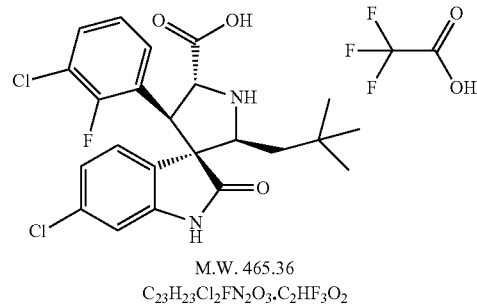

M.W. 465.36
$C_{23}H_{23}Cl_2FN_2O_3 \cdot C_2HF_3O_2$

A solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester (2.6 g, 4.8 mmol) in dichloromethane (60 mL) was added trifluoroacetic acid (8 mL). The reaction mixture was stirred at room temperature for 18 h, then concentrated. The residue was then triturated with ethyl ether hexanes, concentrated, dried in vacuo to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid as a off white solid (2.8 g, 93%).

Example 5

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester

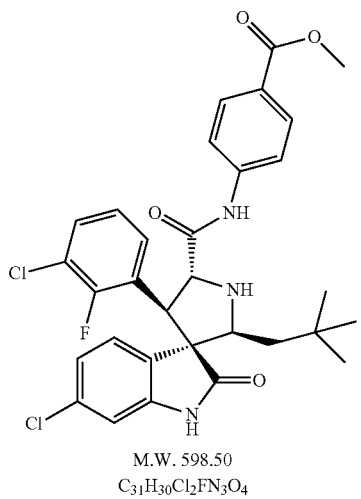

M.W. 598.50
$C_{31}H_{30}Cl_2FN_3O_4$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid (0.86 g, 1.48 mmol) in dichloromethane (20 mL) was added diisopropylethylamine (1.53 g, 11.9 mmol), diphenylphosphinic chloride (Aldrich) (1.41 g, 5.94 mmol) respectively. The mixture was stirred at room temperature for 0.5 h, then methyl aminobenzoate (Acros) (0.22 g, 1.48 mmol) was added. The reaction mixture was stirred at room temperature for 20 h. The mixture was concentrated. The residue was partitioned between ethyl acetate and water. The organic layer was separated, washed with water, brine, dried over $Na_2SO_4$, then concentrated. The residue was purified by chromatography (3-10% of EtOAc in $CH_2Cl_2$) to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester as a off white solid (0.34 g, 38%).

HRMS (ES$^+$) m/z Calcd for $C_{31}H_{30}Cl_2FN_3O_4$+H [(M+H)$^+$]: 598.1070, found: 598.1670.

Example 6

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid

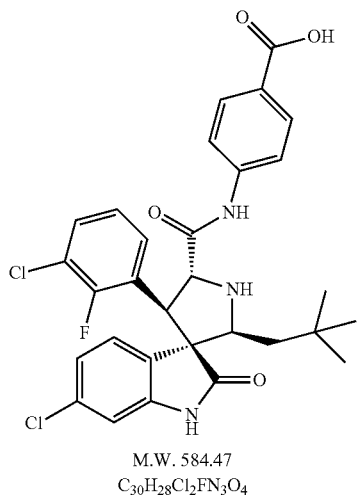

M.W. 584.47
$C_{30}H_{28}Cl_2FN_3O_4$

To a solution of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester prepared in Example 5 (57 mg, 0.095 mmol) in tetrahydrofuran (9 mL) was added an aqueous solution (1N) of NaOH (9 mL, 9 mmol) and methanol (3 mL). The reaction mixture was heated at 80° C. for 1 h, and then cooled to room temperature. The "pH" of the mixture was adjusted to 5-6 by aqueous HCl solution, then concentrated to a small volume. The residue was partitioned between ethyl acetate and water. The organic layer was separated, and the aqueous layer was extracted with ethyl acetate twice. The organic extracts were combined, washed with water, brine, dried over $MgSO_4$, and concentrated to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid as a off white solid (46 mg, 83%).

HRMS (ES$^+$) m/z Calcd for $C_{30}H_{28}Cl_2FN_3O_4$+H [(M+H)$^+$]: 584.1514, found: 584.1518.

Example 7

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide

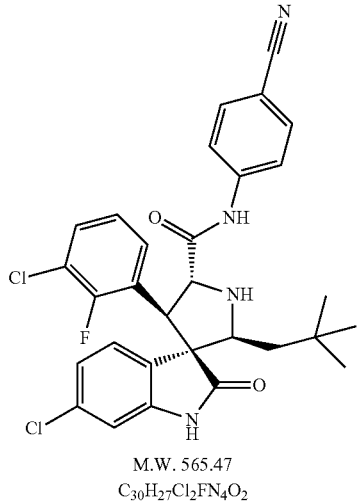

M.W. 565.47
$C_{30}H_{27}Cl_2FN_4O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (2.94 g, 5.07 mmol), was reacted with diisopropylethylamine (5.25 g, 40.6 mmol), diphenylphosphinic chloride (4.8 g, 20.3 mmol), then reacted with 4-aminobenzonitrile (Aldrich) (2.4 g, 20.3 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a off white foam (Yield 1 g, 34%).

HRMS (ES$^+$) m/z Calcd for $C_{30}H_{27}Cl_2FN_4O_2$+H [(M+H)$^+$]: 565.1568, found: 565.1568.

Example 8

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

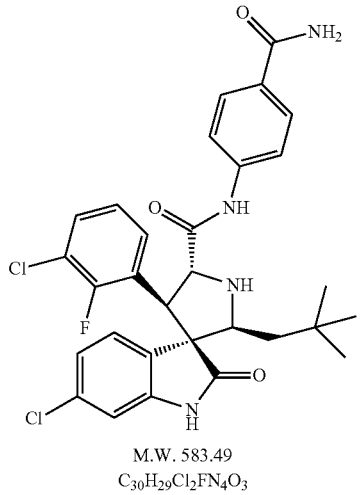

M.W. 583.49
$C_{30}H_{29}Cl_2FN_4O_3$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide (0.35 g, 0.62 mmol) prepared in Example 7 in DMSO (7 mL) at 0° C. was added an aqueous solution (30% Aldrich) of $H_2O_2$ (1.05 g, 9.3 mmol), then aqueous solution (1N) of NaOH (3 mL, 3 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50% to 100% EtOAc in $CH_2Cl_2$) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (Yield 0.26 g, 72%)

HRMS (ES+) m/z Calcd for $C_{30}H_{29}Cl_2FN_4O_3$+H [(M+H)+]: 583.1674, found: 583.1672.

Example 9

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

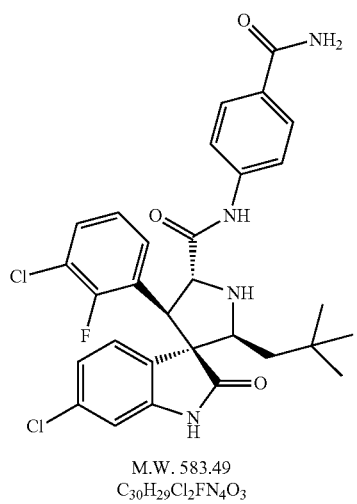

M.W. 583.49
$C_{30}H_{29}Cl_2FN_4O_3$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide prepared in Example 8 (0.53 g) was separated by chiral SFC chromatography to provide chiral (2'S,3'R,4'S,5'R)-6-chloro-4'-(3-chloro-2-fluoro-phenyl)-2'-(2,2-dim-ethyl-propyl)-2-oxo-1,2-dihydro-spiro[indole-3,3'-pyrrolidine]-5'-carboxylic acid (4-carbamoyl-phenyl)-amide as a white solid (0.134 g, 25%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (0.14 g, 26%).

HRMS (ES+) m/z Calcd for $C_{30}H_{29}Cl_2FN_4O_3$+H [(M+H)+]: 583.1674, found: 583.1674.

Example 10

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonyl-phenyl)-amide

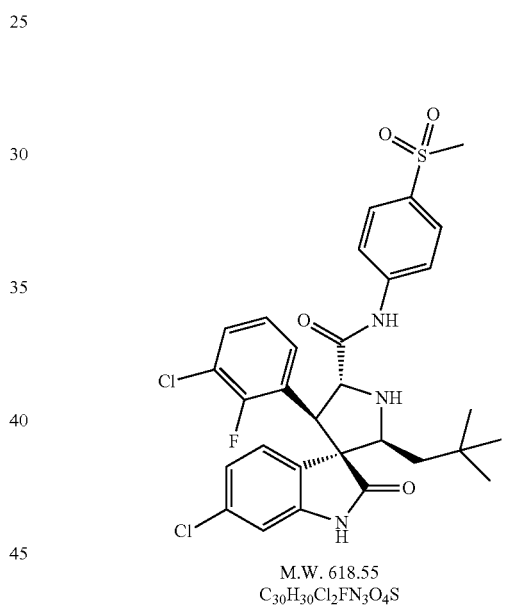

M.W. 618.55
$C_{30}H_{30}Cl_2FN_3O_4S$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.33 g, 0.57 mmol), was reacted with diisopropylethylamine (0.59 g, 4.6 mmol), diphenylphosphinic chloride (0.54 g, 2.3 mmol), then reacted with 4-(methylsulfonyl)aniline (Oakwood) (0.098 g, 0.57 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonyl-phenyl)-amide as a off white foam (Yield 0.11 g, 31%).

HRMS (ES+) m/z Calcd for $C_{30}H_{30}Cl_2FN_3O_4S$+H [(M+H)+]: 618.1391, found: 618.1392.

Example 11

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide

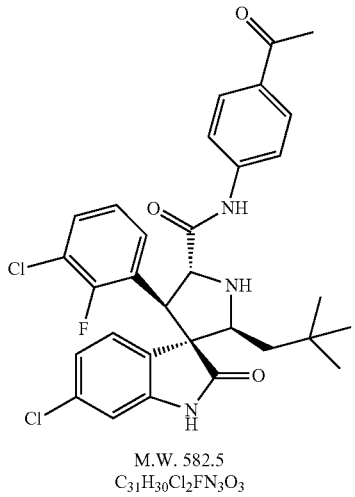

M.W. 582.5
$C_{31}H_{30}Cl_2FN_3O_3$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.36 mmol), was reacted with diisopropylethylamine (0.18 g, 1.4 mmol), diphenylphosphinic chloride (0.17 g, 0.71 mmol), then reacted with 1-(4-aminophenyl)ethanone (Aldrich) (0.058 g, 0.43 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide as a yellow solid (Yield 0.078 g, 38%).

HRMS (ES$^+$) m/z Calcd for $C_{31}H_{30}Cl_2FN_3O_3$+H [(M+H)$^+$]: 582.1721, found: 582.1720.

Example 12

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide

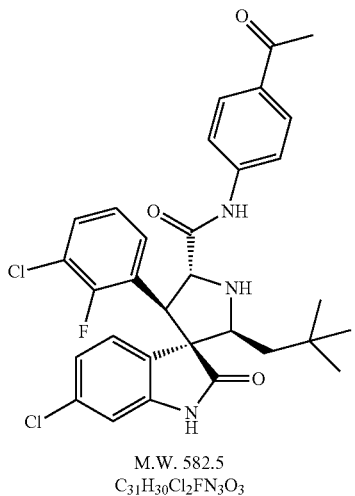

M.W. 582.5
$C_{31}H_{30}Cl_2FN_3O_3$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide prepared in Example 11 (0.125 g) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide as a light yellow solid (0.055 g, 55%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide as a light yellow solid (0.056 g, 44%).

HRMS (ES$^+$) m/z Calcd for $C_{31}H_{30}Cl_2FN_3O_3$+H [(M+H)$^+$]: 582.1721, found: 582.1719.

Example 13

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-fluoro-phenyl)-amide

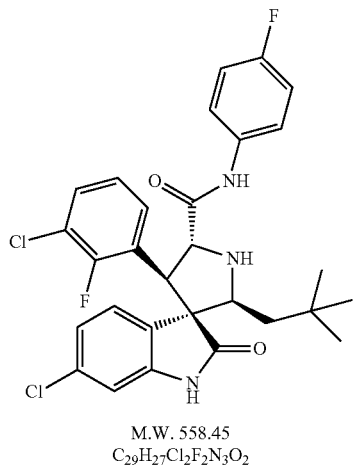

M.W. 558.45
$C_{29}H_{27}Cl_2F_2N_3O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.36 mmol), was reacted with diisopropylethylamine (0.18 g, 1.4 mmol), diphenylphosphinic chloride (0.17 g, 0.71 mmol), then reacted with 4-fluoroaniline (Aldrich) (0.047 g, 0.43 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-fluoro-phenyl)-amide as a yellow solid (Yield 0.094 g, 47%).

HRMS (ES$^+$) m/z Calcd for $C_{29}H_{27}Cl_2F_2N_3O_2$+H [(M+H)$^+$]: 558.1521, found: 558.1523.

Example 14

Preparation of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-thiophene-2-carboxylic acid methyl ester

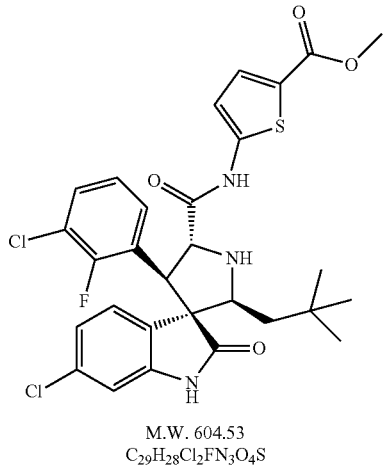

M.W. 604.53
$C_{29}H_{28}Cl_2FN_3O_4S$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.44 mmol), was reacted with diisopropylethylamine (0.23 g, 1.8 mmol), diphenylphosphinic chloride (0.32 g, 1.3 mmol), then reacted with methyl 5-aminothiophene-2-carboxylate (PrincetonBio) (0.084 g, 0.53 mmol) to give rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-thiophene-2-carboxylic acid methyl ester as a off white solid (Yield 0.05 g, 19%).

HRMS (ES$^+$) m/z Calcd for $C_{29}H_{28}Cl_2FN_3O_4S$+H [(M+H)$^+$]: 604.1235, found: 604.1232.

Example 15

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-benzoic acid methyl ester

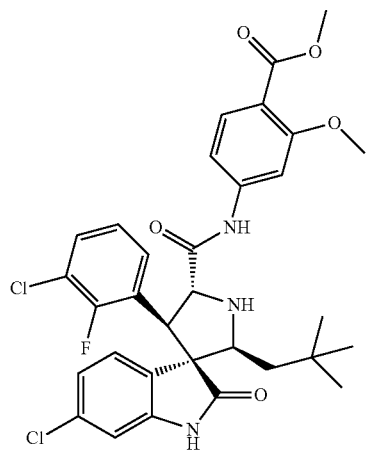

M.W. 628.53
$C_{32}H_{32}Cl_2FN_3O_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.36 mmol), was reacted with diisopropylethylamine (0.18 g, 1.4 mmol), diphenylphosphinic chloride (0.25 g, 1.1 mmol), then reacted with methyl 4-amino-2-methoxybenzoate (Acros) (0.077 g, 0.43 mmol) to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-benzoic acid methyl ester as a white solid (Yield 0.012 g, 54%).

HRMS (ES$^+$) m/z Calcd for $C_{32}H_{32}Cl_2FN_3O_5$+H [(M+H)$^+$]: 1628.1776, found: 628.1774.

Example 16

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid

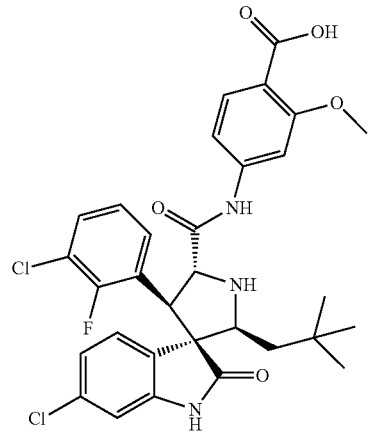

M.W. 614.50
$C_{31}H_{30}Cl_2FN_3O_5$

In a manner similar to the method described in Example 6, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-benzoic acid methyl ester prepared in Example 15 (0.1 g, 0.16 mmol), was heated with aqueous NaOH in methanol and tetrahydrofuran at 78° C. to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid as a off white solid (Yield 0.075 g, 77%).

HRMS (ES$^+$) m/z Calcd for $C_{31}H_{30}Cl_2FN_3O_5$+H [(M+H)$^+$]: 614.1620, found: 614.1618.

Example 17

Preparation of chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid

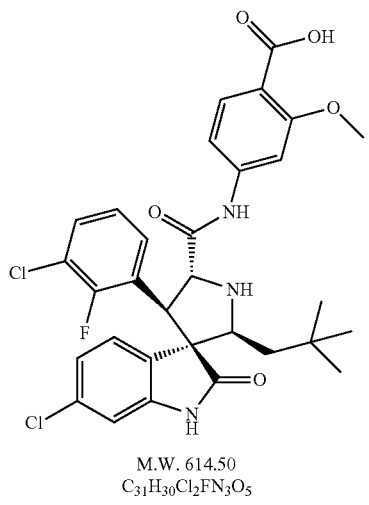

M.W. 614.50
$C_{31}H_{30}Cl_2FN_3O_5$

Rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid prepared in Example 16 (0.11 g) was separated by chiral SFC chromatography to provide chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid as a light yellow solid (40 mg, 36%) and chiral 4-{[(2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-benzoic acid as a light yellow solid (39 mg, 35%).

HRMS (ES+) m/z Calcd for $C_{31}H_{30}Cl_2FN_3O_5$+H [(M+H)+]: 614.1620, found: 614.1617.

Example 18

Preparation of intermediate 2-(4-amino-phenoxy)-ethanol

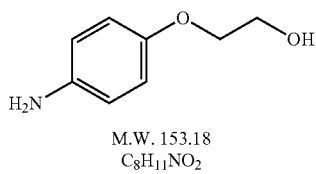

M.W. 153.18
$C_8H_{11}NO_2$

A suspension of 2-(4-nitrophenoxy)ethanol (Aldrich) (2 g, 10.9 mmol) and Pd/C (Aldrich, 10%, 0.2 g) in methanol (50 mL) was vigorously shaken in a Parr under atmosphere of $H_2$ (50 psi) for 1 h. The mixture was filtered through a short pad of celite. The filtrate was concentrated to give 2-(4-aminophenoxy)-ethanol as a light yellow solid (1.6 g, 96%).

Example 19

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide

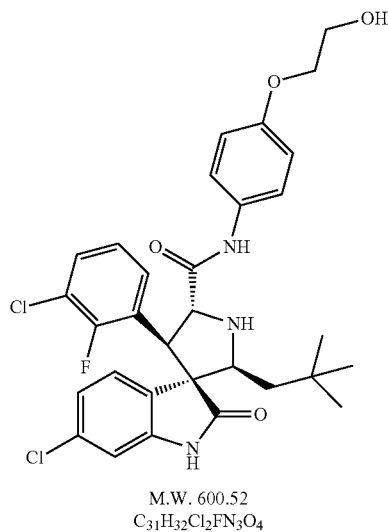

M.W. 600.52
$C_{31}H_{32}Cl_2FN_3O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.44 mmol), was reacted with diisopropylethylamine (0.23 g, 1.8 mmol), diphenylphosphinic chloride (0.32 g, 1.3 mmol), then reacted with 2-(4-aminophenoxy)ethanol (0.082 g, 0.53 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide as a yellow solid (Yield 0.11 g, 41%).

HRMS (ES+) m/z Calcd for $C_{31}H_{32}Cl_2FN_3O_4$+H [(M+H)+]: 600.1827, found: 600.1827.

Example 20

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide

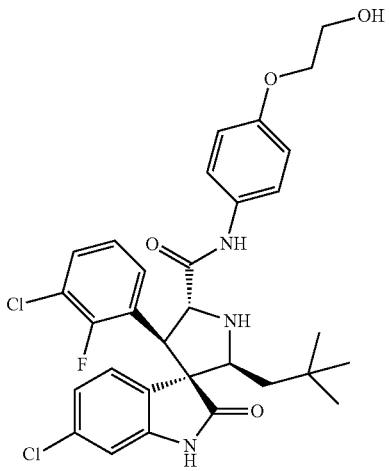

M.W. 600.52
$C_{31}H_{32}Cl_2FN_3O_4$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide prepared in Example 19 (92 mg) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide as a off white solid (38 mg, 41%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide as a off white solid (36 mg, 40%).

HRMS (ES$^+$) m/z Calcd for $C_{31}H_{32}Cl_2FN_3O_4$+H [(M+H)$^{30}$]: 600.1827, found: 600.1824.

Example 21

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-chloro-phenyl)-amide

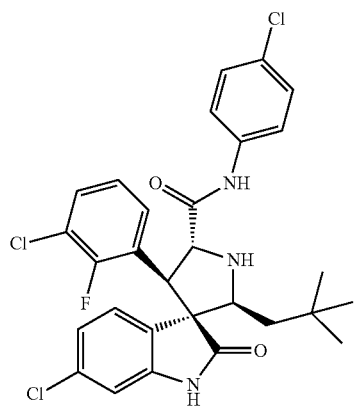

M.W. 574.91
$C_{29}H_{27}Cl_3FN_3O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.36 mmol), was reacted with diisopropylethylamine (0.18 g, 1.4 mmol), diphenylphosphinic chloride (0.25 g, 1.1 mmol), then reacted with 4-chloroaniline (Fluka) (0.054 g, 0.43 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-chloro-phenyl)-amide as a off white solid (Yield 95 mg, 47%).

HRMS (ES$^+$) m/z Calcd for $C_{29}H_{27}Cl_3FN_3O_2$+H [(M+H)$^+$]: 574.1226, found: 574.1224.

Example 22

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide

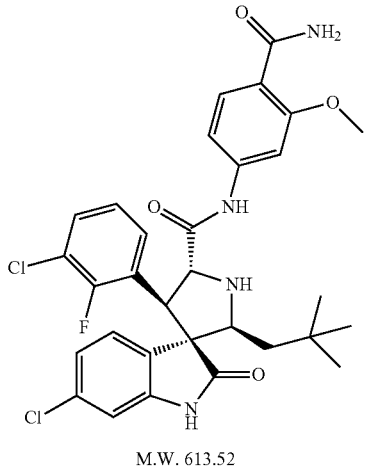

M.W. 613.52
$C_{31}H_{30}Cl_2FN_4O_4$

To a solution of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid prepared in Example 16 (55 mg, 0.09 mmol) in N,N-dimethylformamide (2 mL) was added EDCI (34 mg, 0.18 mmol), HOBt (24 mg, 0.18 mmol), NH$_4$Cl (48 mg, 0.9 mmol), and triethylamine (18 mg, 0.18 mmol) sequentially. The reaction mixture was heated at 80° C. for 1 h. The mixture was poured into water, then extracted with ethyl acetate three times. The organic layers were combined, washed with water, brine, dried over MgSO$_4$, and concentrated. The residue was purified by chromatography (25% to 100% EtOAc in hexanes) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide as a off white solid (Yield, 35 mg, 64%)

HRMS (ES$^+$) m/z Calcd for $C_{31}H_{30}Cl_2PN_4O_4$+H [(M+H)$^+$]: 613.1779, found: 613.1779.

Example 23

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide

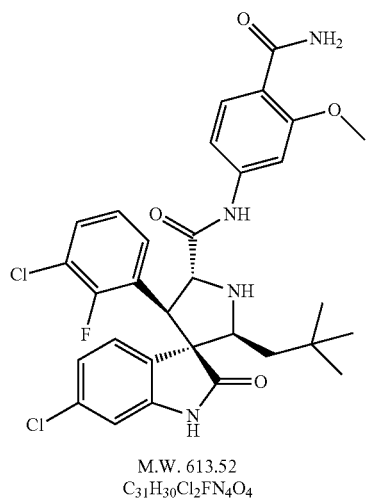

M.W. 613.52
$C_{31}H_{30}Cl_2FN_4O_4$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide prepared in Example 22 (70 mg) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide as a off white solid (10 mg, 14%) and chiral (2'R,3'S,4'S,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide as a off white solid (10 mg, 14%).

MS (ES$^+$) m/z Calcd for $C_{31}H_{30}Cl_2FN_4O_4$+H [(M+H)$^+$]: 613, found: 613.

Example 24

Preparation of intermediate 4-amino-2-chlorobenzoic acid methyl ester

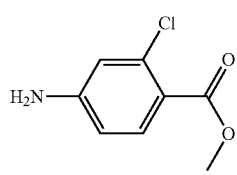

A solution of 4-nitro-2-chlorobenzoic acid methyl ester (Aldrich, 700 mg, 3.24 mmol) in ethyl acetate (50 mL) was added 10% Pd/C (50 mg). The mixture was vigorously shaken in a Parr under an atmosphere of hydrogen (50 psi) for 3 h. The mixture was filtered through a short pad of celite and the filtrate was concentrated to give 4-amino-2-chlorobenzoic acid methyl ester as a light yellow solid which was directly used for the next step.

Example 25

Preparation of rac-2-chloro-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester

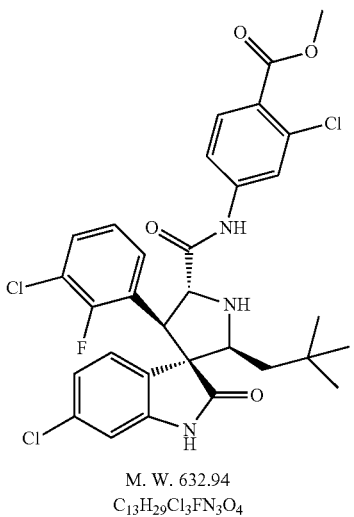

M. W. 632.94
$C_{13}H_{29}Cl_3FN_3O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.44 mmol), was reacted with diisopropylethylamine (0.23 g, 1.8 mmol), diphenylphosphinic chloride (0.32 g, 1.3 mmol), then reacted with methyl 4-amino-2-chlorobenzoate (0.099 g, 0.53 mmol) to give rac-2-chloro-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester as a white solid (Yield 0.09 g, 32%).

HRMS (ES$^+$) m/z Calcd for $C_{31}H_{29}Cl_3FN_3O_4$+H [(M+H)$^+$]: 632.1281, found: 632.1281.

Example 26

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide

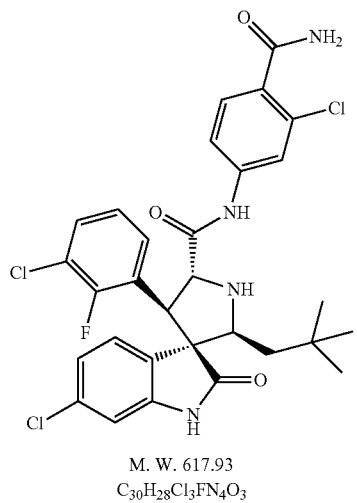

M. W. 617.93
$C_{30}H_{28}Cl_3FN_4O_3$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide prepared in Example 224 (0.14 g) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide as a white solid (46 mg, 33%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide as a white solid (38 mg, 27%).

HRMS (ES$^+$) m/z Calcd for $C_{30}H_{28}Cl_3FN_4O_3$+H [(M+H)$^{3O}$]: 617.1284, found: 617.1285.

Example 27

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-2-oxo-1,2-dihydro-pyridin-4-yl)-amide

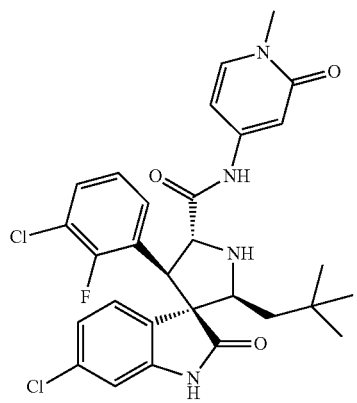

M. W. 571.48
$C_{29}H_{29}Cl_2FN_4O_3$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.33 g, 0.57 mmol) in 1,2-dichloroethane (30 mL) was added diisopropylethylamine (0.59 g, 4.6 mmol), diphenylphosphinic chloride (Aldrich) (0.54 g, 2.3 mmol) respectively. The mixture was stirred at room temperature for 0.5 h, then 4-amino-1-methyl-pyridin-2-one (Molbridge) (0.07 g, 0.57 mmol) was added. The reaction mixture was heated and stirred at 60° C. for 10 h. The mixture was concentrated. The residue was partitioned between ethyl acetate and water. The organic layer was separated, washed with water, brine, dried over $Na_2SO_4$, then concentrated. The residue was purified by chromatography (5-10% of MeOH in EtOAc) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-2-oxo-1,2-dihydro-pyridin-4-yl)-amide as a off white solid (32 mg, 10%).

HRMS (ES$^+$) m/z Calcd for $C_{29}H_{29}Cl_2FN_4O_3$+H [(M+H)$^+$]: 571.1674, found: 571.1673.

Example 28

Preparation of intermediate 4-amino-1-[2-(tert-butyl-dimethyl-silanyloxy)-ethyl]-1H-pyridin-2-one

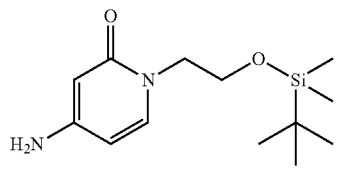

M. W. 268.43
$C_{13}H_{24}N_2O_2Si$

To a solution of 4-aminopyridin-2(1H)-one (Molbridge) (0.9 g, 8.17 mmol) in DMF (30 mL) was added NaH (60%, 490 mg, 12.3 mmol). The mixture was stirred at room temperature for 30 min before (2-bromoethoxy)(tert-butyl)dimethylsilane (2.15 g, 8.99 mmol) was added. The reaction mixture was heated at 78° C. for 15 h. The mixture was cooled and poured into $H_2O$ (100 mL) and extracted with ethyl acetate (3×50 mL). The organic layers were combined, washed with $H_2O$ (5×50 mL), brine (50 mL), dried over $MgSO_4$ and concentrated. The residue was purified by flash chromatography (silica gel, 40+S, 0% to 10% MeOH in EtOAc) to give 4-amino-1-[2-(tert-butyl-dimethyl-silanyloxy)-ethyl]-1H-pyridin-2-one as a white solid (0.9 g, 41%).

Example 29

Preparation of intermediate rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {1-[2-(tert-butyl-dimethyl-silanyloxy)-ethyl]-2-oxo-1,2-dihydro-pyridin-4-yl}-amide

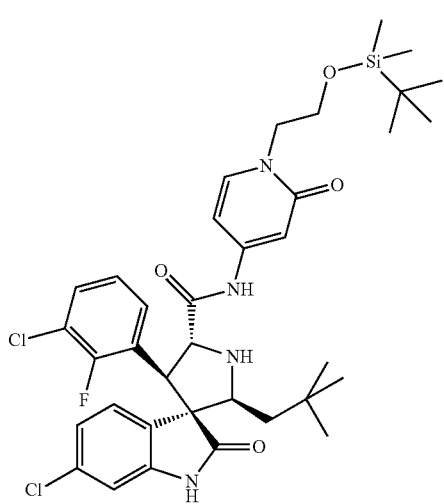

M. W. 715.77  $C_{36}H_{45}Cl_2FN_4O_4Si$

In a manner similar to the method described in Example 27, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.5 g, 0.86 mmol), was reacted with diisopropylethylamine (0.89 g, 6.9 mmol), diphenylphosphinic chloride (0.82 g, 3.5 mmol), then reacted with 4-amino-1-[2-(tert-butyl-dimethyl-silanyloxy)-ethyl]-1H-pyridin-2-one (0.23 g, 0.86 mmol) at 60° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {1-[2-(tert-butyl-dimethyl-silanyloxy)-ethyl]-2-oxo-1,2-dihydro-pyridin-4-yl}-amide as a off white foam (Yield 0.2 g, 32%).

Example 30

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1-propyl-1,2-dihydro-pyridin-4-yl)-amide

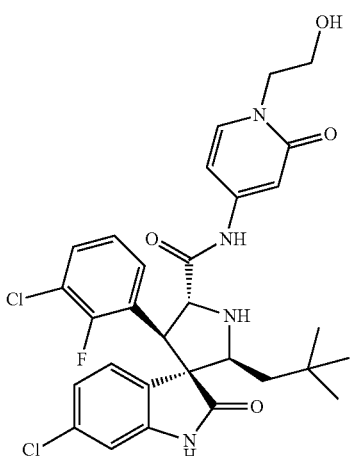

M. W. 601.5  $C_{30}H_{31}Cl_3FN_4O_4$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {1-[2-(tert-butyl-dimethyl-silanyloxy)-ethyl]-2-oxo-1,2-dihydro-pyridin-4-yl}-amide (0.1 g, 0.14 mmol) in tetrahydrofuran (3 mL) was added aqueous HCl solution (1N, 3 mL, 3 mmol). The reaction mixture was stirred at room temperature for 1 h. The mixture was concentrated. The residue was partitioned between ethyl acetate and aqueous saturated NaHCO$_3$ solution. The organic layer was separated, washed with water, brine, dried over Na$_2$SO$_4$, then concentrated. The residue was purified by chromatography (10-15% of MeOH in EtOAc) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1-propyl-1,2-dihydro-pyridin-4-yl)-amide as a white solid (Yield, 12 mg, 14%).

HRMS (ES$^+$) m/z Calcd for $C_{30}H_{31}Cl_2FN_4O_4$+H [(M+H)$^+$]: 601.1779, found: 601.1781.

Example 31

Preparation of rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid methyl ester

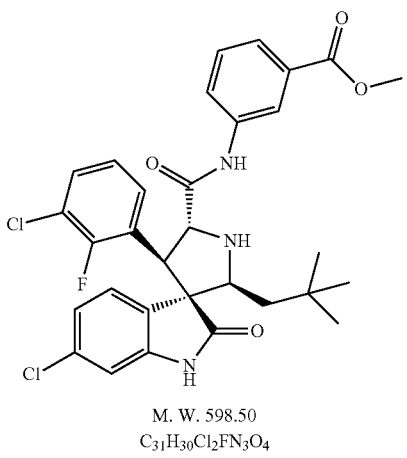

M. W. 598.50
C₃₁H₃₀Cl₂FN₃O₄

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.53 mmol), was reacted with diisopropylethylamine (0.28 g, 2.1 mmol), diphenylphosphinic chloride (0.38 g, 1.6 mmol), then reacted with methyl 3-aminobenzoate (Aldrich) (0.12 g, 0.8 mmol) to give rac-3-{[(2'S,3'R,4'S,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester as a off white solid (Yield, 0.07 g, 22%).

HRMS (ES⁺) m/z Calcd for $C_{31}H_{30}Cl_2FN_3O_4$+H [(M+H)⁺]: 598.1670, found: 598.1669.

Example 32

Preparation of rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid

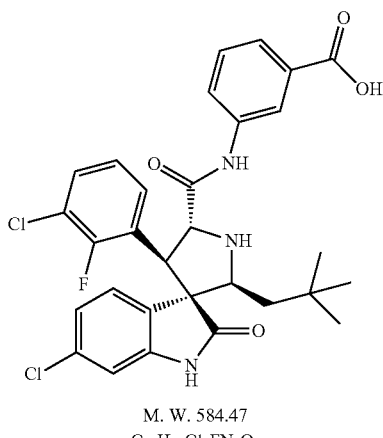

M. W. 584.47
C₃₀H₂₈Cl₂FN₃O₄

In a manner similar to the method described in Example 16, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester (60 mg, 0.1 mmol) was reacted with aqueous NaOH in methanol and tetrahydrofuran at 60° C. to rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid as a yellow solid (Yield, 50 mg, 85%).

HRMS (ES⁺) m/z Calcd for $C_{30}H_{28}Cl_2FN_3O_4$+H [(M+H)⁺]: 584.1514, found: 584.1513.

Example 33

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-carbamoyl-phenyl)-amide

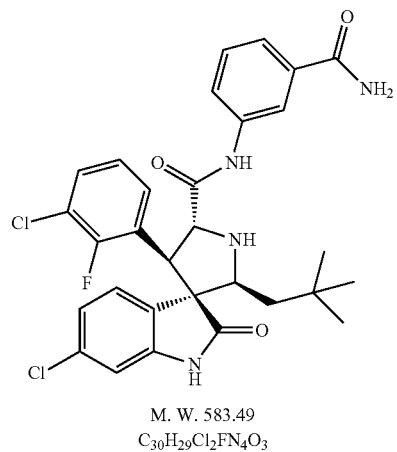

M. W. 583.49
C₃₀H₂₉Cl₂FN₄O₃

In a manner similar to the method described in Example 22, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid (42 mg, 0.072 mmol) was reacted with EDCI (28 mg, 0.14 mmol), HOBt (19 mg, 0.14 mmol), triethylamine (15 mg, 0.14 mmol), and NH₄Cl (38 mg, 0.72 mmol) at 80° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-carbamoyl-phenyl)-amide as a light yellow solid (Yield, 25 mg, 60%).

HRMS (ES⁺) m/z Calcd for $C_{30}H_{29}Cl_2FN_4O_3$+1-1 [(M+H)⁺]: 583.1674, found: 583.1672.

Example 34

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide

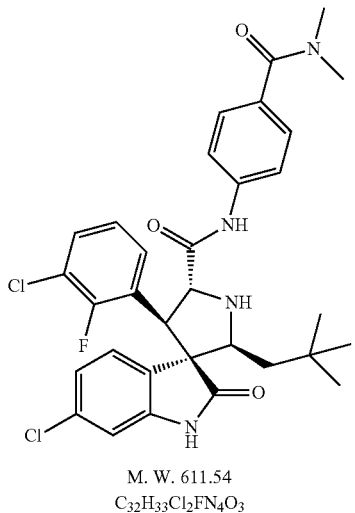

M. W. 611.54
$C_{32}H_{33}Cl_2FN_4O_3$

In a manner similar to the method described in Example 22, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid (30 mg, 0.051 mmol) was reacted with EDCI (19 mg, 0.1 mmol), HOBt (14 mg, 0.1 mmol), and dimethylamine (0.1 mL, $O_2$ mmol) at 60° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide as a light yellow solid (Yield, 10 mg, 32%).

HRMS (ES+) m/z Calcd for $C_{32}H_{33}Cl_2FN_4O_3$+H [(M+H)+]: 611.1987, found: 611.1983.

Example 35

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide

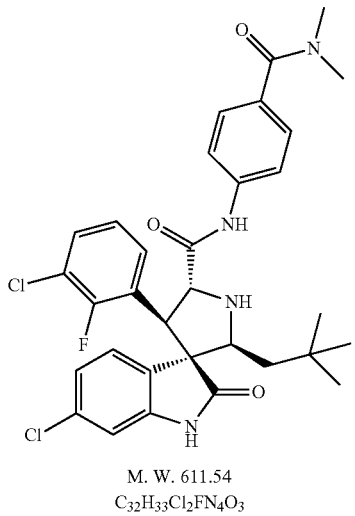

M. W. 611.54
$C_{32}H_{33}Cl_2FN_4O_3$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide prepared (95 mg) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide as a off white solid (24 mg, 25%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide as a off white solid (26 mg, 27%).

HRMS (ES+) m/z Calcd for $C_{32}H_{33}Cl_2FN_4O_3$+H [(M+H)+]: 611.1987, found: 611.1986.

Example 36

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid p-tolylamide

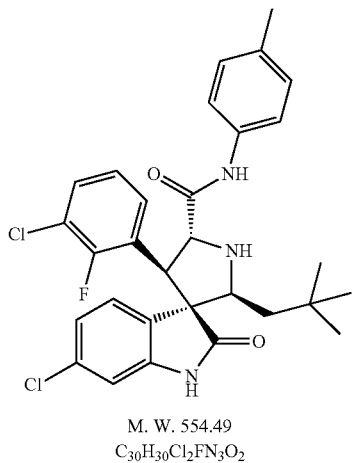

M. W. 554.49
$C_{30}H_{30}Cl_2FN_3O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.36 mmol), was reacted with diisopropylethylamine (0.18 g, 1.4 mmol), diphenylphosphinic chloride (0.25 g, 1.1 mmol), then reacted with p-toluidine (Aldrich) (0.057 g, 0.53 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid p-tolylamide as a white solid (Yield, 30 mg, 15%).

HRMS (ES+) m/z Calcd for $C_{30}H_{30}Cl_2FN_3O_2$+H [(M+H)+]: 554.1772, found: 554.1772.

Example 37

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-methanesulfonyl-phenyl)-amide

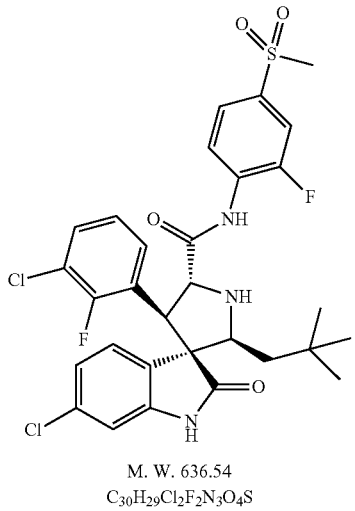

M. W. 636.54
C₃₀H₂₉Cl₂F₂N₃O₄S

In a manner similar to the method described in Example 27, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.36 g, 0.62 mmol), was reacted with diisopropylethylamine (0.64 g, 5 mmol), diphenylphosphinic chloride (0.59 g, 2.5 mmol), then reacted with 2-fluoro-4-(methylsulfonyl)aniline (Matrix) (0.12 g, 0.62 mmol) at 80° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-methanesulfonyl-phenyl)-amide as a off white solid (Yield 20 mg, 5%).

HRMS (ES⁺) m/z Calcd for $C_{30}H_{29}Cl_2F_2N_3O_4S+H$ [(M+H)⁺]: 636.1297, found: 636.1295.

Example 38

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide

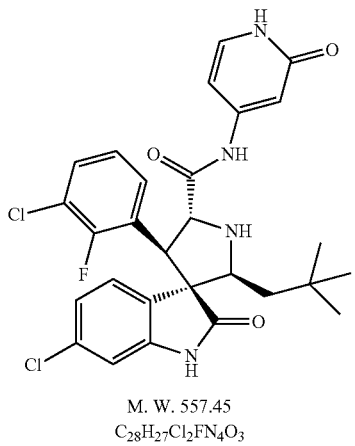

M. W. 557.45
C₂₈H₂₇Cl₂FN₄O₃

In a manner similar to the method described in Example 27, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.45 g, 0.78 mmol), was reacted with diisopropylethylamine (0.8 g, 6.2 mmol), diphenylphosphinic chloride (0.74 g, 3.1 mmol), then reacted with 4-aminopyridin-2(1H)-one (Molbridge) (0.086 g, 0.78 mmol) in 1,2-dichloroethane at 60° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide as a off white solid (Yield 28 mg, 6%).

HRMS (ES⁺) m/z Calcd for $C_{28}H_{27}Cl_2FN_4O_3+H$ [(M+H)⁺]: 557.1517, found: 557.1513.

Example 39

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide

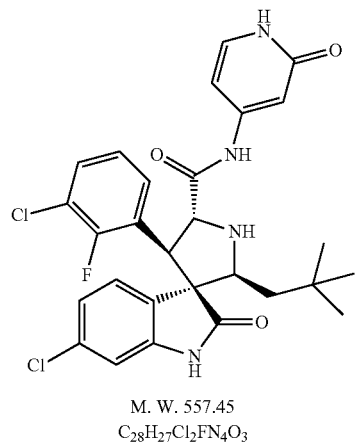

M. W. 557.45
C₂₈H₂₇Cl₂FN₄O₃

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide (0.1 g) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide as a off white solid (32 mg, 32%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide as a off white solid (31 mg, 31%).

MS (ES⁺) m/z Calcd for $C_{28}H_{27}Cl_2FN_4O_3+H$ [(M+H)⁺]: 557, found: 557.

Example 40

Preparation of intermediate 1-(4-amino-phenyl)-2-(tert-butyl-dimethyl-silanyloxy)-ethanone

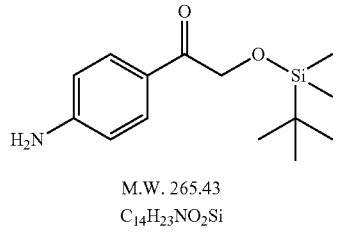

M.W. 265.43
C₁₄H₂₃NO₂Si

Step A.

To a solution of 2-hydroxy-1-(4-nitrophenyl)ethanone (1 g, 5.52 mmol) in DMF (25 ml) was added imidazole (564 mg, 8.28 mmol), followed by the addition of tert-butylchlorodimethylsilane (915 mg, 6.07 mmol). The reaction mixture was stirred at room temperature for 3 h. The mixture was poured into H₂O (25 mL) and extracted with ethyl acetate (3×25 mL). The organic layers were combined, washed with H₂O (5×25 mL), brine (1×25 mL), dried over MgSO₄ and concentrated in vacuo to give 2-(tert-butyldimethylsilyloxy)-1-(4-nitrophenyl)ethanone as a yellow solid (1.6 g, 98%).

Step B.

To a solution of 2-(tert-butyldimethylsilyloxy)-1-(4-nitrophenyl)ethanone (0.54 g, 1.83 mmol) in methanol (60 mL) was added an aqueous solution (15 mL) of ammonium chloride (0.98 g, 18.3 mmol), followed by the addition of Zinc (1.2 g, 18.3 mmol). The reaction mixture was stirred at room temperature for 1 h. The mixture was filtered through a short pad of celite. The filtrate was concentrated to a small volume, then hen partitioned between ethyl acetate and water. The organic layer was separated, the aqueous layer was extracted with ethyl acetate. The organic layers were combined, washed with water, brine, dried over MgSO₄, and concentrated to give 1-(4-amino-phenyl)-2-(tert-butyl-dimethyl-silanyloxy)-ethanone as a white foam (0.4 g, 82%)

Example 41

Preparation of intermediate rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {4-[2-(tert-butyl-dimethyl-silanyloxy)-acetyl]-phenyl}-amide

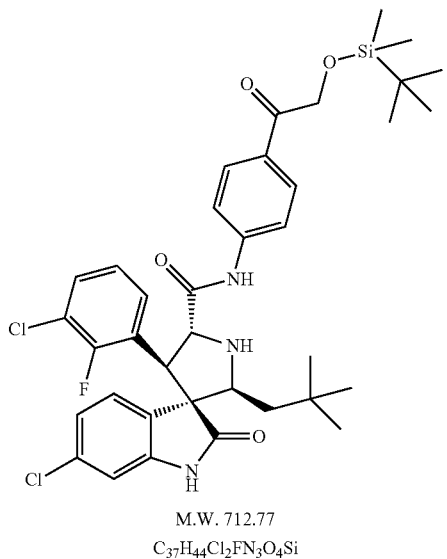

M.W. 712.77
C₃₇H₄₄Cl₂FN₃O₄Si

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.53 mmol), was reacted with diisopropylethylamine (0.28 g, 2.1 mmol), diphenylphosphinic chloride (0.38 g, 1.6 mmol), then reacted with 1-(4-amino-phenyl)-2-(tert-butyl-dimethyl-silanyloxy)-ethanone (0.21 g, 0.8 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {4-[2-(tert-butyl-dimethyl-silanyloxy)-acetyl]-phenyl}-amide as a yellow foam (Yield 0.1 g, 26%).

Example 42

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-acetyl)-phenyl]-amide

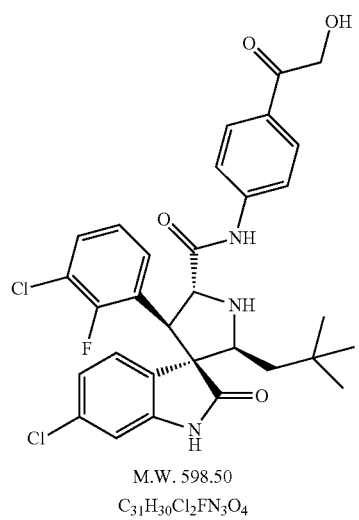

M.W. 598.50
C₃₁H₃₀Cl₂FN₃O₄

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {4-[2-(tert-butyl-dimethyl-silanyloxy)-acetyl]-phenyl}-amide (0.1 g, 0.14 mmol) in tetrahydrofuran (5 mL) was added aqueous HCl solution (1N, 5 mL, 5 mmol). The reaction mixture was stirred at room temperature for 0.5 h. The mixture was concentrated. The residue was partitioned between ethyl acetate and aqueous saturated NaHCO₃ solution. The organic layer was separated, washed with water, brine, dried over Na₂SO₄, then concentrated. The residue was purified by chromatography (silica gel, 5-80% of EtOAc in hexanes) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-acetyl)-phenyl]-amide as a yellow solid (Yield, 35 mg, 42%).

HRMS (ES⁺) m/z Calcd for $C_{31}H_{30}Cl_2FN_3O_4$+H [(M+H)⁺]: 598.1670, found: 598.1670.

Example 43

Preparation of intermediate rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {1-[2-(tert-butyl-dimethyl-silanyloxy)-ethyl]-1H-pyrazol-3-yl}-amide

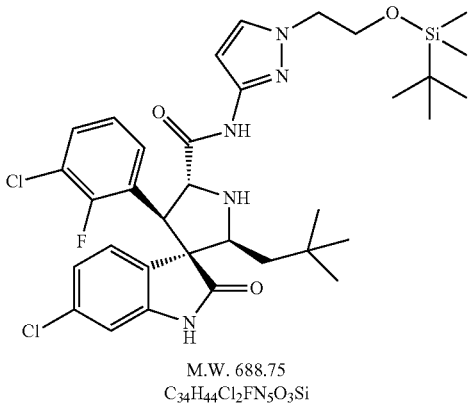

M.W. 688.75
$C_{34}H_{44}Cl_2FN_5O_3Si$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.44 mmol), was reacted with diisopropylethylamine (0.23 g, 1.8 mmol), diphenylphosphinic chloride (0.32 g, 1.3 mmol), then reacted with 1-(2-(tert-butyldimethylsilyloxy)ethyl)-1H-pyrazol-3-amine (WO2009127544) (0.16 g, 0.67 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {1-[2-(tert-butyl-dimethyl-silanyloxy)-ethyl]-1H-pyrazol-3-yl}-amide as a off white foam (Yield 0.1 g, 33%).

Example 44

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [1-(2-hydroxy-ethyl)-1-pyrazol-3-yl]-amide

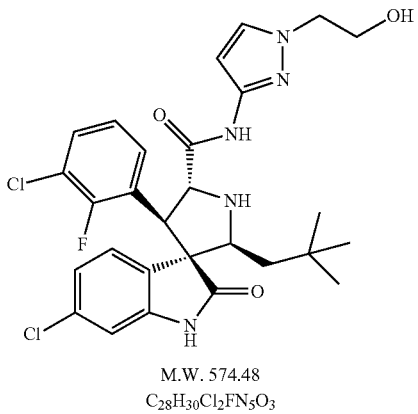

M.W. 574.48
$C_{28}H_{30}Cl_2FN_5O_3$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid {1-[2-(tert-butyl-dimethyl-silanyloxy)-ethyl]-1H-pyrazol-3-yl}-amide (0.1 g, 0.15 mmol) in tetrahydrofuran (5 mL) was added aqueous HCl solution (1N, 5 mL, 5 mmol). The reaction mixture was stirred at room temperature for 0.5 h. The mixture was concentrated. The residue was partitioned between ethyl acetate and aqueous saturated $NaHCO_3$ solution. The organic layer was separated, washed with water, brine, dried over $Na_2SO_4$, then concentrated. The residue was purified by chromatography (silica gel, 25-100% of EtOAc in hexanes) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [1-(2-hydroxy-ethyl)-1H-pyrazol-3-yl]-amide as a white solid (Yield, 45 mg, 54%).

HRMS (ES+) m/z Calcd for $C_{28}H_{30}Cl_2FN_5O_3$+H [(M+H)+]: 574.1783, found: 574.1784.

Example 45

Preparation of intermediate E/Z-6-chloro-3-(3-chloro-2-fluoro-benzylidene)-5-fluoro-1,3-dihydro-indol-2-one

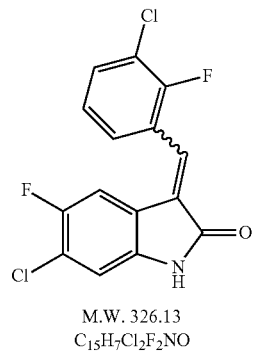

M.W. 326.13
$C_{15}H_7Cl_2F_2NO$

To the mixture of 6-chloro-5-fluoroindolin-2-one (Natrochem) (2.88 g, 15.5 mmol) and 3-chloro-2-fluorobenzaldehyde (3.69 g, 23.3 mmol) (Aldrich) in methanol (140 mL) was added piperidine (3.96 g, 46.6 mmol) (Aldrich) dropwise. The mixture was then heated at 50° C. for 3 h. After cooled to 4° C., the mixture was filtered and resulting precipitate was collected, dried to give E/Z-6-chloro-3-(3-chloro-2-fluoro-benzylidene)-5-fluoro-1,3-dihydro-indol-2-one as a yellow solid (Yield 4.4 g, 87%).

Example 46

Preparation of intermediate rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid tert-butyl ester

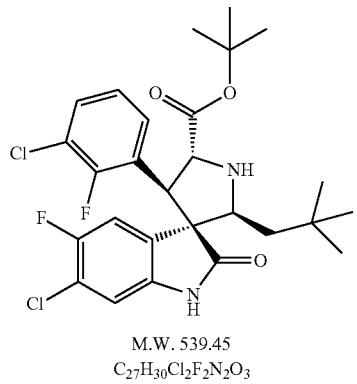

M.W. 539.45
$C_{27}H_{30}Cl_2F_2N_2O_3$

To a solution of [3,3-dimethyl-but-(E)-ylideneamino]-acetic acid tert-butyl ester (2.85 g, 13.3 mmol) prepared in Example 1 and E/Z-6-chloro-3-(3-chloro-2-fluoro-benzylidene)-5-fluoro-1,3-dihydro-indol-2-one (2.9 g, 8.9 mmol) prepared in Example 45 in dichloromethane (100 mL) were added triethylamine (3.7 mL, 27 mmol) and AgF (1.1 g, 8.9 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into t-butanol (30 mL), and DBU (4.0 g, 27 mmol) was added. The reaction mixture was heated at 80° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (EtOAc:hexanes=1:3, 1:2) to give as rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid tert-butyl ester a white solid (1.8 g, 38%)

Example 47

Preparation of intermediate rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid trifluoroacetic acid

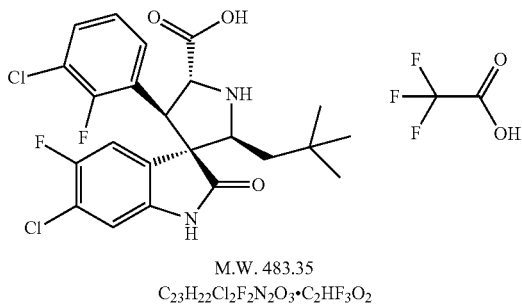

M.W. 483.35
$C_{23}H_{22}Cl_2F_2N_2O_3 \cdot C_2HF_3O_2$

A solution of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid tert-butyl ester (1.8 g, 3.4 mmol) in dichloromethane (20 mL) was added trifluoroacetic acid (7 mL). The reaction mixture was stirred at room temperature for 18 h, then concentrated. The residue was then triturated with ethyl ether hexanes, concentrated, dried in vacuo to give rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid trifluoroacetic acid as a off white solid (2 g, 93%).

Example 48

Preparation of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-phenyl)-amide

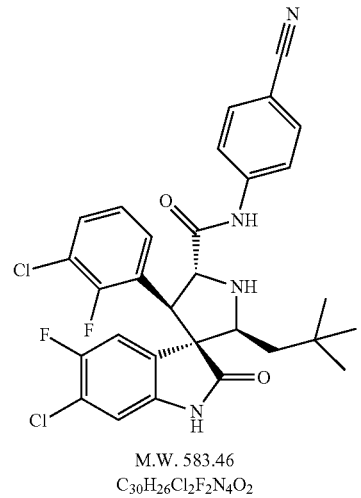

M.W. 583.46
$C_{30}H_{26}Cl_2F_2N_4O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid trifluoroacetic acid prepared in Example 47 (0.33 g, 0.55 mmol), was reacted with diisopropylethylamine (0.29 g, 2.2 mmol), diphenylphosphinic chloride (0.26 g, 1.1 mmol), then reacted with 4-aminobenzonitrile (Aldrich) (0.2 g, 1.7 mmol) to give rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-phenyl)-amide as a white solid (Yield 0.1 g, 31%).

HRMS (ES$^+$) m/z Calcd for $C_{30}H_{26}Cl_2F_2N_4O_2$+H [(M+H)$^+$]: 583.1474, found: 583.1474.

Example 49

Preparation of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide

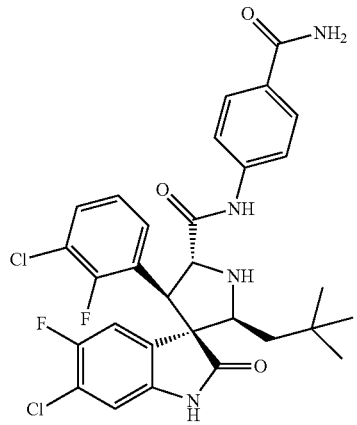

M.W. 601.48
C30H28Cl2F2N4O3

To the solution of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-phenyl)-amide (0.1 g, 0.17 mmol) prepared in Example 48 in DMSO (5 mL) at 0° C. was added an aqueous solution (30% Aldrich) of $H_2O_2$ (0.39 g, 3.4 mmol), then aqueous solution (1N) of NaOH (1.7 mL, 1.7 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was triturated with dichloromethane and hexanes to give rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide as a white solid (Yield 0.1 g, 97%).

HRMS (ES$^+$) m/z Calcd for $C_{30}H_{28}Cl_2F_2N_4O_3$+H [(M+H)$^+$]: 601.1580, found: 601.1581.

Example 50

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

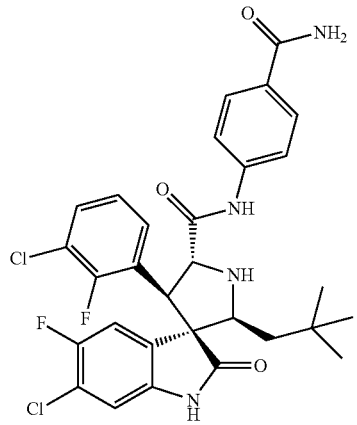

M.W. 601.48
C30H28Cl2F2N4O3

Rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide prepared in Example 49 (0.15 g) was separated by chiral SFC chromatography to provide chiral (2'S,3'R,4'S,5'S)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide as a off white solid (43 mg, 29%) and chiral (2'R,3'S,4'R,5'S)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide as a off white solid (49 mg, 33%).

Example 51

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-iodo-phenyl)-amide

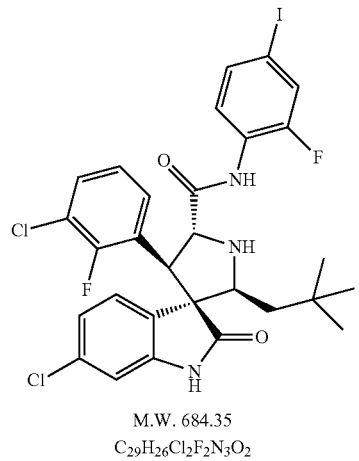

M.W. 684.35
C29H26Cl2F2N3O2

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-, 3,3'-pyrrolidine]-5'-carboxylic acid trifluoroacetic acid prepared in Example 4 (0.3 g, 0.53 mmol), was reacted with diisopropylethylamine (0.28 g, 2.1 mmol), diphenylphosphinic chloride (0.38 g, 1.6 mmol), then reacted with 2-fluoro-4-iodoaniline (Aldrich) (0.15 g, 0.64 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-iodo-phenyl)-amide as a yellow solid (Yield, 0.21 g, 58%).

HRMS (ES$^+$) m/z Calcd for $C_{29}H_{26}Cl_2F_2N_3O_2$+H [(M+H)$^+$]: 684.0488, found: 684.0489.

Example 52

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-fluoro-phenyl)-amide

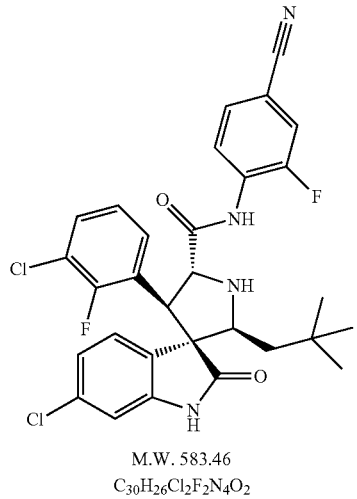

M.W. 583.46
$C_{30}H_{26}Cl_2F_2N_4O_2$

In a manner similar to the method described in Example 27, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.53 g, 0.92 mmol), was reacted with diisopropylethylamine (0.95 g, 7.4 mmol), diphenylphosphinic chloride (0.87 g, 3.7 mmol), then reacted with 4-amino-3-fluorobenzonitrile (Matrix) (0.13 g, 0.92 mmol) in 1,2-dichloroethane at 70° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-fluoro-phenyl)-amide as a off white solid (Yield 0.14 g, 26%).

HRMS (ES+) m/z Calcd for $C_{30}H_{26}Cl_2F_2N_4O_2$+H [(M+H)+]: 583.1474, found: 583.1475.

Example 53

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-fluoro-phenyl)-amide

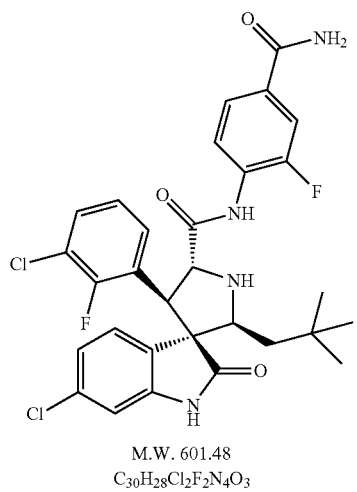

M.W. 601.48
$C_{30}H_{28}Cl_2F_2N_4O_3$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-fluoro-phenyl)-amide (50 mg, 0.086 mmol) in DMSO (1 mL) at 0° C. was added an aqueous solution (30% Aldrich) of $H_2O_2$ (0.15 g, 1.3 mmol), then aqueous solution (1N) of NaOH (0.4 mL, 0.4 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-fluoro-phenyl)-amide as a off white solid (Yield 25 mg, 49%)

HRMS (ES+) m/z Calcd for $C_{30}H_{28}Cl_2F_2N_4O_3$+H [(M+H)+]: 601.1580, found: 601.1575.

Example 54

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-fluoro-phenyl)-amide

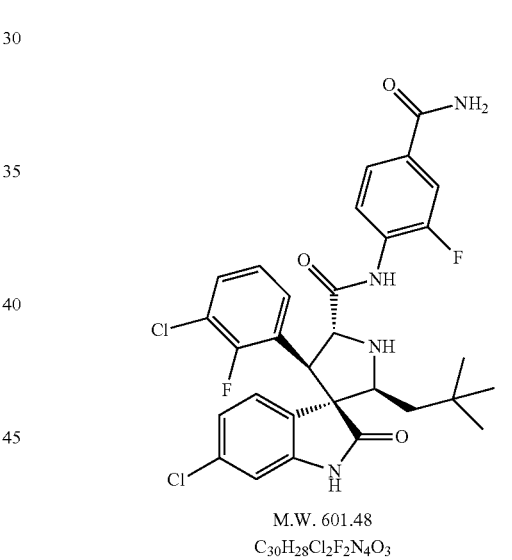

M.W. 601.48
$C_{30}H_{28}Cl_2F_2N_4O_3$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-fluoro-phenyl)-amide (0.15 g) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-fluoro-phenyl)-amide as a off white solid (49 mg, 33%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-fluoro-phenyl)-amide as a off white solid (45 mg, 30%).

MS (ES+) m/z Calcd for $C_{30}H_{28}Cl_2F_2N_4O_3$+H [(M+H)+]: 601, found: 601.

Example 55

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [1-(2-hydroxy-2-methyl-propyl)-1H-pyrazol-3-yl]-amide trifluoroacetic acid

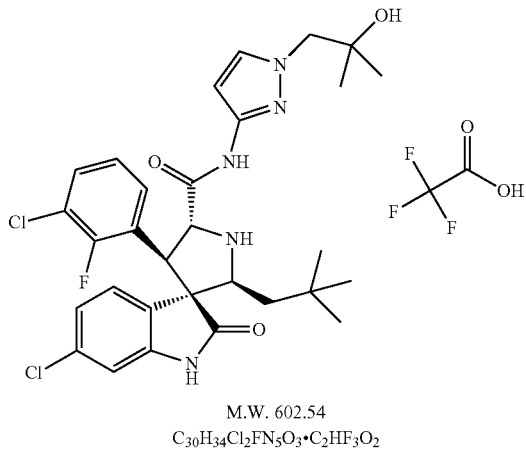

M.W. 602.54
$C_{30}H_{34}Cl_2FN_5O_3 \cdot C_2HF_3O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.44 mmol), was reacted with diisopropylethylamine (0.23 g, 1.8 mmol), diphenylphosphinic chloride (0.32 g, 1.3 mmol), then reacted with 1-(3-amino-1H-pyrazol-1-yl)-2-methylpropan-2-ol (WO2009127544) (0.11 g, 0.67 mmol) at room temperature and purified by Prep-HPLC to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [1-(2-hydroxy-2-methyl-propyl)-1H-pyrazol-3-yl]-amide as a trifluoroacetic acid salt: white solid (Yield 62 mg, 20%).

MS (ES$^+$) m/z Calcd for $C_{30}H_{34}Cl_2FN_5O_3^{-41}$ [(M+H)$^+$]: 602, found: 602.

Example 56

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-iodo-phenyl)-amide

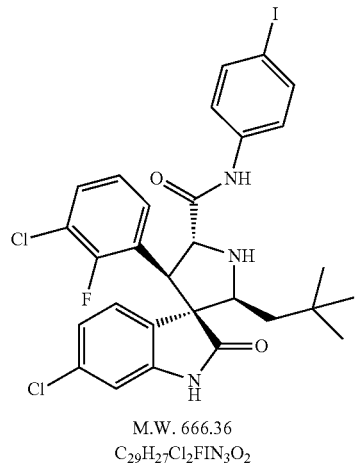

M.W. 666.36
$C_{29}H_{27}Cl_2FIN_3O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.36 mmol), was reacted with diisopropylethylamine (0.18 g, 1.4 mmol), diphenylphosphinic chloride (0.25 g, 1.1 mmol), then reacted with 4-iodoaniline (Aldrich) (0.093 g, 0.43 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-iodo-phenyl)-amide as a off white solid (Yield 0.09 g, 38%).

MS (ES$^+$) m/z Calcd for $C_{29}H_{27}Cl_2FIN_3O_2$+H [(M+H)$^+$]: 666, found: 666.

Example 57

Preparation of intermediate 4-amino-3-methoxy-benzonitrile

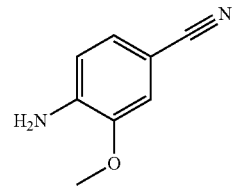

M.W. 148.17
$C_8H_8N_2O$

Step A.

A mixture of 3-methoxy-4-nitrobenzoic acid (Acros) (10 g, 51 mmol) in thionyl chloride (36 g) was heated at reflux for 2 h. The mixture was concentrated. To the residue was added a methanolic solution (7 N) of ammonia. The reaction mixture was stirred at room temperature for 72 h. The mixture was concentrated, and the residue was partitioned between ethyl acetate and water. The precipitate between the two layers was filtered and collected to give 3-methoxy-4-nitrobenzamide as a light yellow solid (8 g, 81%).

Step B.

To a solution of 3-methoxy-4-nitrobenzamide (8 g, 41 mmol) in dioxane (300 mL) was added pyridine (32 g, 408 mmol), followed by dropwise addition of trifluoroacetic anhydride (43 g, 204 mmol). The reaction mixture was stirred at room temperature for 5 h. Water was added to quench the reaction. The mixture was concentrated, then the residue was partitioned between ethyl acetate and water. The organic layer was separated, the aqueous layer was extracted with ethyl acetate. The organic layers were combined, washed with water, aqueous saturated CuSO$_4$ solution, brine, dried over MgSO$_4$, and concentrated to give 3-methoxy-4-nitrobenzonitrile as a off white solid (6.5 g, 90%)

Step C.

To the suspension of 3-methoxy-4-nitrobenzonitrile (11.4 g, 64 mmol) in ethyl acetate (60 mL) was added 10% Pd/C (1 g). The reaction mixture was vigorously shaken in a Parr under an atmosphere of hydrogen (50 psi) at room temperature for 45 min. The mixture was filtered through a short pad of celite, and the filtrate was concentrated to give 4-amino-3-methoxy-benzonitrile as a yellow oil, which solidified at stand (9.5 g, 95%)

Example 58

Preparation of rac-(2'S,3'R,4'S,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide

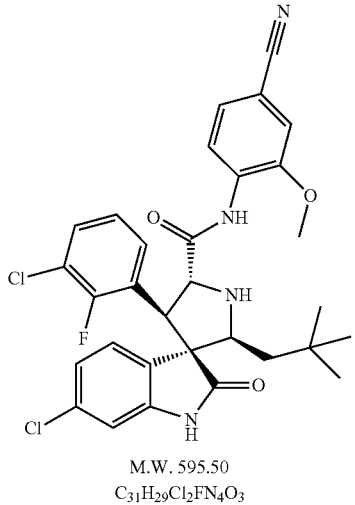

M.W. 595.50
$C_{31}H_{29}Cl_2FN_4O_3$

In a manner similar to the method described in Example 27, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.95 g, 1.64 mmol), was reacted with diisopropylethylamine (1.7 g, 13.1 mmol), diphenylphosphinic chloride (1.55 g, 6.6 mmol), then reacted with 4-amino-3-methoxy-benzonitrile (0.49 g, 3.28 mmol) in 1,2-dichloroethane at 70° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide as a off white foam (Yield, 0.34 g, 35%).

HRMS (ES$^+$) m/z Calcd for $C_{31}H_{29}Cl_2FN_4O_3$+H [(M+H)$^+$]: 595.1674, found: 595.1674.

Example 59

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

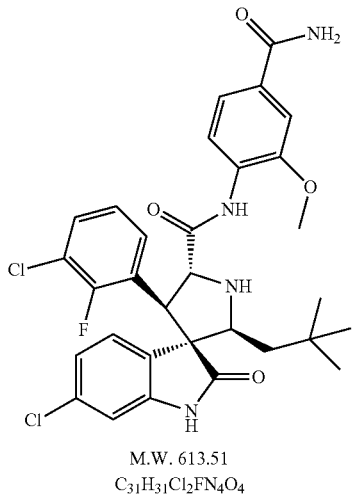

M.W. 613.51
$C_{31}H_{31}Cl_2FN_4O_4$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide (0.34 g, 0.57 mmol) in DMSO (15 mL) at 0° C. was added an aqueous solution (30% Aldrich) of $H_2O_2$ (0.56 g, 16 mmol), then aqueous solution (1N) of NaOH (5.7 mL, 5.7 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50%-100% EtOAc in $CH_2Cl_2$) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a off white solid (Yield, 0.22 g, 63%)

HRMS (ES$^+$) m/z Calcd for $C_{31}H_{31}Cl_2FN_4O_4$+H [(M+H)$^+$]: 613.1779, found: 613.1779.

Example 60

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

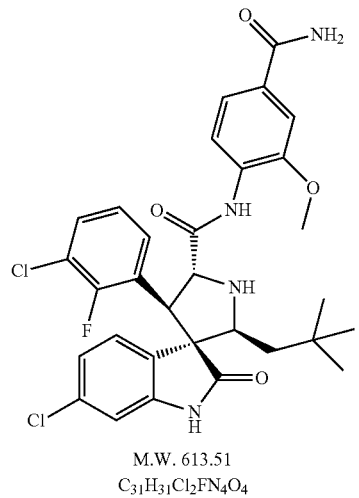

M.W. 613.51
$C_{31}H_{31}Cl_2FN_4O_4$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide (0.22 g) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a off white solid (68 mg, 31%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a off white solid (70 mg, 32%).

Example 61

Preparation of intermediate E/Z-6-chloro-3-(3-chloro-benzylidene)-1,3-dihydro-indol-2-one

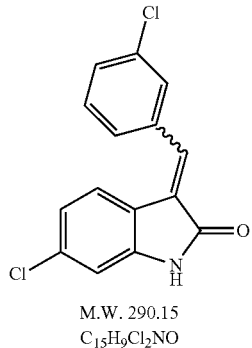

M.W. 290.15
$C_{15}H_9Cl_2NO$

To the mixture of 6-chloro-2-oxindole (16.2 g, 92 mmol) (Crescent) and 3-chloro-benzaldehyde (12.9 g, 92 mmol) (Aldrich) in methanol (109 mL) was added pyrrolidine (6.55 g, 92 mmol) (Aldrich) dropwise. The mixture was then heated at 70° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 25.2 g, 95%).

Example 62

Preparation of intermediate rac-(2'S,3'R,4'S,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid tert-butyl ester

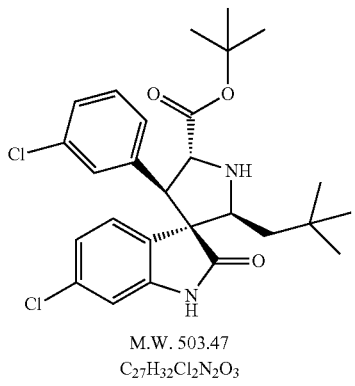

M.W. 503.47
$C_{27}H_{32}Cl_2N_2O_3$

To a solution of [3,3-dimethyl-but-(E)-ylideneamino]-acetic acid tert-butyl ester (4.8 g, 22.5 mmol) prepared in Example 1 and E/Z-6-chloro-3-(3-chloro-benzylidene)-1,3-dihydro-indol-2-one (4.9 g, 17 mmol) prepared in Example 61 in dichloromethane (200 mL) were added triethylamine (14 mL, 99 mmol) and AgF (3.3 g, 26 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into t-butanol (30 mL), and DBU (21 g, 138 mmol) was added. The reaction mixture was heated at 80° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (EtOAc:CH$_2$Cl$_2$=1:20, 1:10) to give as rac-(2'S,3'R,4'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid tert-butyl ester a white solid (3.8 g, 45%)

Example 63

Preparation of intermediate rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid trifluoroacetic acid

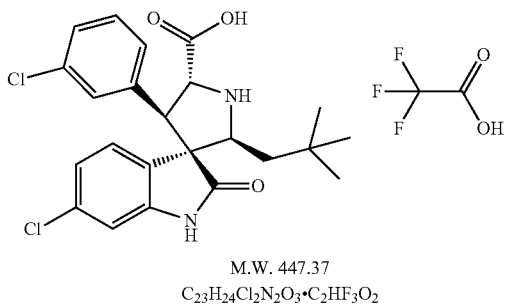

M.W. 447.37
$C_{23}H_{24}Cl_2N_2O_3 \cdot C_2HF_3O_2$

A solution of rac-(2'S,3'R,4'S,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid tert-butyl ester (3.6 g, 7.2 mmol) in dichloromethane (20 mL) was added trifluoroacetic acid (7 mL). The reaction mixture was stirred at room temperature for 18 h, then concentrated. The residue was then triturated with ethyl ether hexanes, concentrated, dried in vacuo to give rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid trifluoroacetic acid as a off white solid (3.8 g, 95%).

Example 64

Preparation of rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-cyano-phenyl)-amide

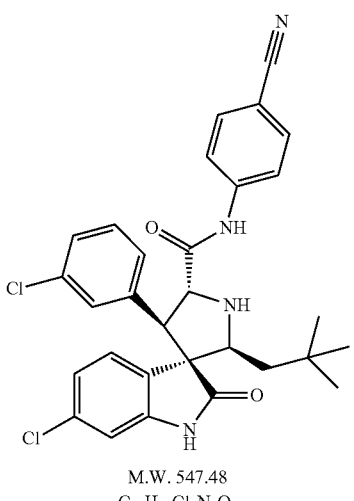

M.W. 547.48
$C_{30}H_{28}Cl_2N_4O_2$

In a manner similar to the method described in Example 5, rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 63 (0.95 g, 1.7 mmol), was reacted with diisopropylethylamine (1.8 g, 14 mmol), diphenylphosphinic chloride (1.6 g, 6.8 mmol), then reacted with 4-aminobenzonitrile (Aldrich) (0.8 g, 6.8 mmol) to give rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a white solid (Yield 0.5 g, 54%).

HRMS (ES$^+$) m/z Calcd for $C_{30}H_{28}Cl_2N_4O_2$+H [(M+H)$^+$]: 547.1662, found: 547.1663.

Example 65A

Preparation of rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

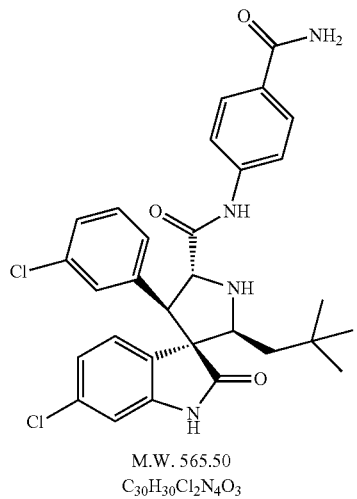

M.W. 565.50
$C_{30}H_{30}Cl_2N_4O_3$

To the solution of rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-cyano-phenyl)-amide (0.5 g, 0.91 mmol) prepared in Example 64 in DMSO (15 mL) at 0° C. was added an aqueous solution (30% Aldrich) of $H_2O_2$ (0.56 mL, 18 mmol), then aqueous solution (1N) of NaOH (4 mL, 4 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatograph (50-100% EtOAc in $CH_2Cl_2$) to give rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (Yield 0.3 g, 58%)

HRMS (ES$^+$) m/z Calcd for $C_{30}H_{30}Cl_2N_4O_3$+11 [(M+H)$^+$]: 565.1768, found: 565.1769.

Example 65B

Preparation of chiral (2'S,3'R,4'R,5'R)-6-chloro-4'-(3-chloro-phenyl)-2'-(2,2-dimethyl-propyl)-2-oxo-1, 2-dihydro-spiro[indole-3,3'-pyrrolidine]-5'-carboxylic acid (4-carbamoyl-phenyl)-amide

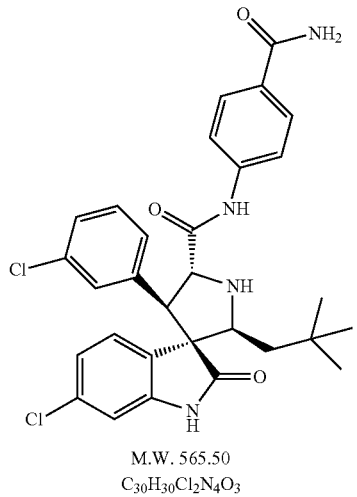

M.W. 565.50
$C_{30}H_{30}Cl_2N_4O_3$

Rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide (0.2 g) was separated by chiral SFC chromatography to provide chiral (2'S,3'R,4'R,5'R)-6-chloro-4'-(3-chloro-phenyl)-2'-(2,2-dimethyl-propyl)-2-oxo-1,2-dihydro-spiro[indole-3, 3'-pyrrolidine]-5'-carboxylic acid (4-carbamoyl-phenyl)-amide as a white solid (92 mg, 46%) and chiral (2'R,3'S,4'S, 5'S)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (91 mg, 45%).

Example 66

Preparation of rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide

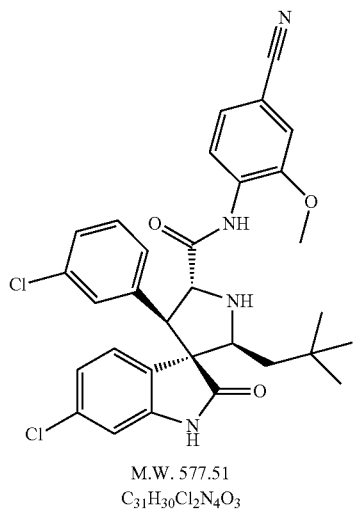

M.W. 577.51
$C_{31}H_{30}Cl_2N_4O_3$

In a manner similar to the method described in Example 5, rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 63 (1.0 g, 1.8 mmol), was reacted with diisopropylethylamine (2.1 g, 16.5 mmol), diphenylphosphinic chloride (1.74 g, 7.3 mmol), then reacted with 4-amino-3-methoxy-benzonitrile prepared in Example 57 (0.54 g, 3.7 mmol) to give rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide as a white solid (Yield, 0.17 g, 16%).

HRMS (ES$^+$) m/z Calcd for $C_{31}H_{30}Cl_2N_4O_3$+H [(M+H)$^+$]: 577.1768, found: 577.1764.

Example 67

Preparation of rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

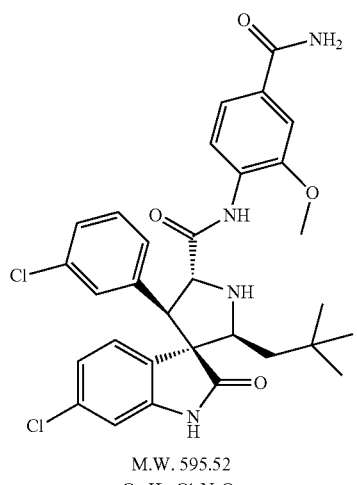

M.W. 595.52
$C_{31}H_{32}Cl_2N_4O_4$

To the solution of rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide (0.16 g, 0.28 mmol) in DMSO (3 mL) at 0° C. was added an aqueous solution (30% Aldrich) of $H_2O_2$ (0.47 g, 4.2 mmol) aqueous solution (1N) of NaOH (1.4 mL, 1.4 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over $MgSO_4$, and concentrated to give rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (Yield, 0.12 g, 73%)

HRMS (ES$^+$) m/z Calcd for $C_{31}H_{32}Cl_2N_4O_4$+H [(M+H)$^+$]: 595.1874, found: 595.1874.

Example 68

Preparation of chiral (2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

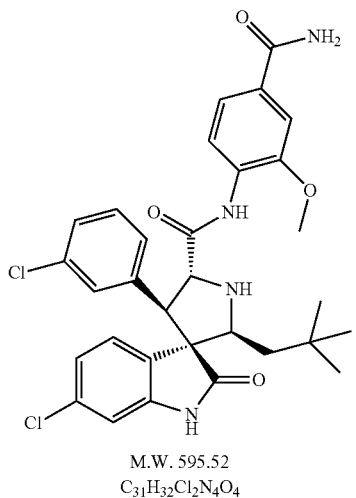

M.W. 595.52
$C_{31}H_{32}Cl_2N_4O_4$

Rac-(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide (0.16 g) was separated by chiral SFC chromatography to provide chiral (2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (64 mg, 40%) and chiral (2'R,3'S,4'S,5'S)-6-chloro-4'-(3-chloro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (61 mg, 38%).

MS (ES$^+$) m/z Calcd for $C_{31}H_{32}Cl_2N_4O_4$+H [(M+H)$^+$]: 595, found: 595.

Example 69

Preparation of intermediate E/Z-6-chloro-3-(3-chloro-2-fluoro-benzylidene)-4-fluoro-1,3-dihydro-indol-2-one

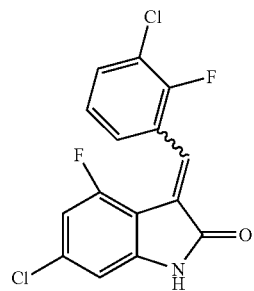

M. W. 326.13 $C_{15}H_7Cl_2F_2NO$

To the mixture of 6-chloro-4-fluoroindolin-2-one (Natrochem, 85% purity) (1.1 g, 5.0 mmol) and 3-chloro-2-fluorobenzaldehyde (2.4 g, 15 mmol) (Oakwood) in methanol (50 mL) was added piperidine (1.7 g, 20 mmol) (Aldrich) dropwise. The mixture was then heated at 50° C. for 3 h. After cooled to 4° C., the mixture was filtered and resulting precipitate was collected, washed with cold methanol, dried to give the first batch of desired product (1.22 g). The filtrate was concentrated, and the residue was partitioned between ethyl acetate and water. The organic layer was separated, washed with water, brine, dried over MgSO$_4$, and concentrated. The residue was purified by chromatography (20-35% EtOAc in hexanes) to give the second batch of desired product (0.32 g). The two batches were combined to give E/Z-6-chloro-3-(3-chloro-2-fluoro-benzylidene)-4-fluoro-1,3-dihydro-indol-2-one as a yellow solid (Yield 1.54 g, 94%).

Example 70

Preparation of intermediate rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid tert-butyl ester

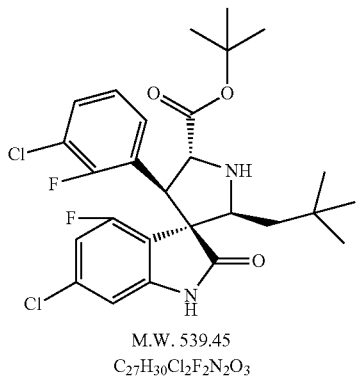

M.W. 539.45
$C_{27}H_{30}Cl_2F_2N_2O_3$

To a solution of [3,3-dimethyl-but-(E)-ylideneamino]-acetic acid tert-butyl ester (3.2 g, 15 mmol) prepared in Example 1 and E/Z-6-chloro-3-(3-chloro-2-fluoro-benzylidene)-4-fluoro-1,3-dihydro-indol-2-one (1.5 g, 4.7 mmol) prepared in Example 69 in dichloromethane (60 mL) were added triethylamine (9.6 mL, 69 mmol) and AgF (3 g, 24 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into t-butanol (20 mL), and DBU (2.5 g, 16 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (EtOAc:hexanes=1:3, 1:2) to give as rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid tert-butyl ester a white solid (1.8 g, 71%)

Example 71

Preparation of intermediate rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid trifluoroacetic acid

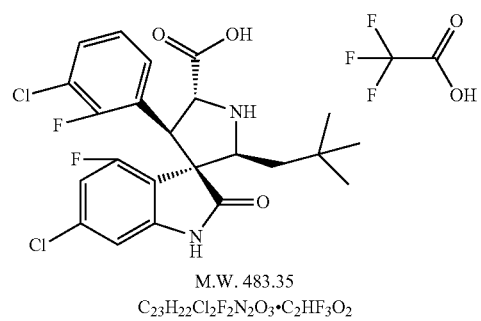

M.W. 483.35
$C_{23}H_{22}Cl_2F_2N_2O_3 \cdot C_2HF_3O_2$

A solution of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid tert-butyl ester (1.8 g, 3.4 mmol) in dichloromethane (10 mL) was added trifluoroacetic acid (5 mL). The reaction mixture was stirred at room temperature for 20 h, then concentrated. The residue was then triturated with ethyl ether hexanes, concentrated, dried in vacuo to give rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid trifluoroacetic acid as a off white solid (1.9 g, 95%).

Example 72

Preparation of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-phenyl)-amide

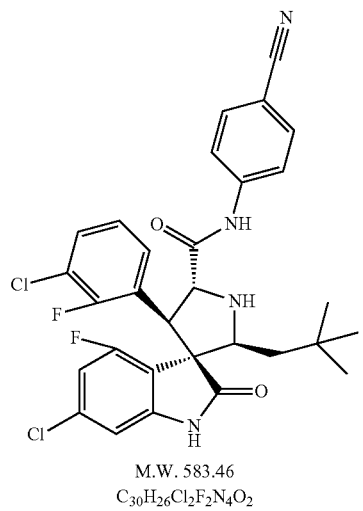

M.W. 583.46
$C_{30}H_{26}Cl_2F_2N_4O_2$

In a manner similar to the method described in Example 27, rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid trifluoroacetic acid prepared in Example 71 (0.4 g, 0.67 mmol), was reacted with diisopropylethylamine (0.69 g, 5.4 mmol), diphenylphosphinic chloride (0.63 g, 2.7 mmol) in 1,2-dichloroethane at room temperature, then reacted with 4-aminobenzonitrile (Aldrich) (0.24 g, 2.1 mmol) at 80° C. to give rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-phenyl)-amide as a white solid (Yield 0.2 g, 51%).

HRMS (ES$^+$) m/z Calcd for $C_{30}H_{26}Cl_2F_2N_4O_2$+H [(M+H)$^{3o}$]: 583.1474, found: 583.1473.

Example 73

Preparation of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide

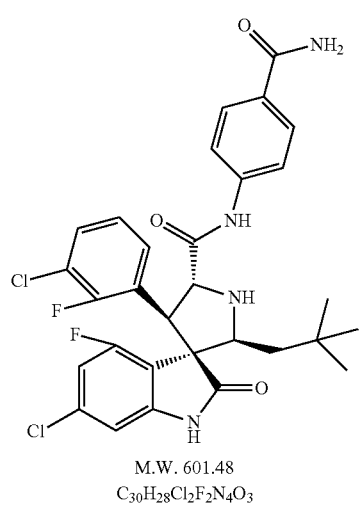

M.W. 601.48
$C_{30}H_{28}Cl_2F_2N_4O_3$

To the solution of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-phenyl)-amide (0.2 g, 0.34 mmol) prepared in Example 72 in DMSO (15 mL) at 0° C. was added an aqueous solution (30% Aldrich) of $H_2O_2$ (0.39 g, 3.4 mmol), then aqueous solution (1N) of NaOH (1.7 mL, 1.7 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide as a white solid (Yield 0.18 g, 87%)

HRMS (ES$^+$) m/z Calcd for $C_{30}H_{28}Cl_2F_2N_4O_3$+H [(M+H)$^+$]: 601.1580, found: 601.1580.

Example 74

Preparation of chiral (2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide

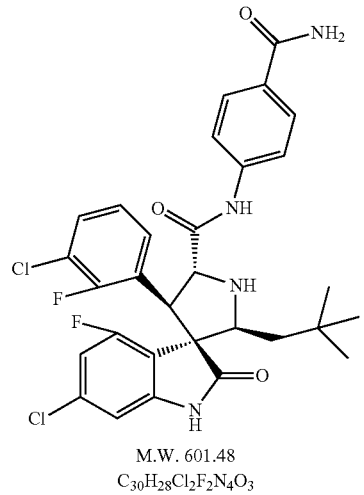

M.W. 601.48
$C_{30}H_{28}Cl_2F_2N_4O_3$

Rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide prepared in Example 73 (0.15 g) was separated by chiral SFC chromatography to provide chiral (2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide as a white solid (67 mg, 39%) and chiral (2'R,3'S,4'R,5'S)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide as a white solid (60 mg, 35%).

Example 75

Preparation of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-2-methoxy-phenyl)-amide

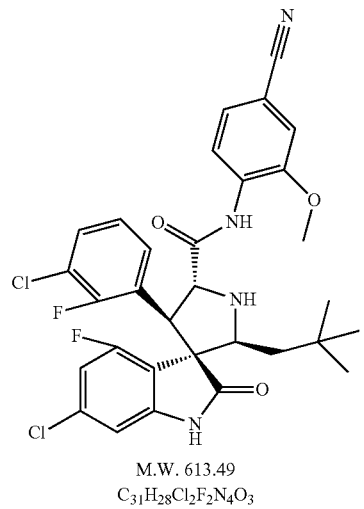

M.W. 613.49
$C_{31}H_{28}Cl_2F_2N_4O_3$

In a manner similar to the method described in Example 27, rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid trifluoroacetic acid prepared in Example 71 (0.95 g, 1.6 mmol), was reacted with diisopropylethylamine (0.82 g, 6.4 mmol), diphenylphosphinic chloride (0.75 g, 3.2 mmol) in 1,2-dichloroethane at room temperature, then reacted with 4-amino-3-methoxy benzonitrile prepared in Example 57 (0.71 g, 4.8 mmol) at 80° C. to give rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-2-methoxy-phenyl)-amide as a white solid (Yield 0.3 g, 31%).

HRMS (ES+) m/z Calcd for $C_{31}H_{28}Cl_2F_2N_4O_3$+H [(M+H)+]: 613.1580, found: 613.1576.

Example 76

Preparation of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-2-methoxy-phenyl)-amide

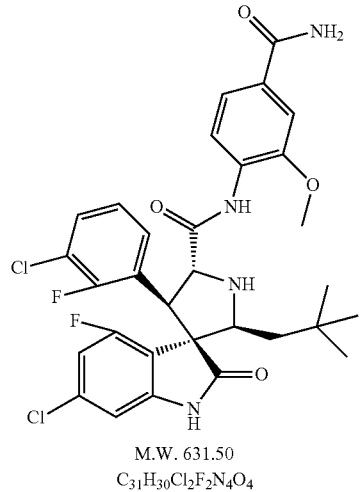

M.W. 631.50
$C_{31}H_{30}Cl_2F_2N_4O_4$

To the solution of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-2-methoxy-phenyl)-amide (0.3 g, 0.49 mmol) prepared in Example 75 in DMSO (15 mL) at 0° C. was added an aqueous solution (30% Aldrich) of $H_2O_2$ (1.1 g, 9.7 mmol), then aqueous solution (1N) of NaOH (4.9 mL, 4.9 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-2-methoxy-phenyl)-amide as a white solid (Yield 0.2 g, 64%)

HRMS (ES+) m/z Calcd for $C_{31}H_{30}Cl_2F_2N_4O_4$+H [(M+H)+]: 631.1685, found: 631.1683.

Example 77

Preparation of chiral (2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-2-methoxy-phenyl)-amide

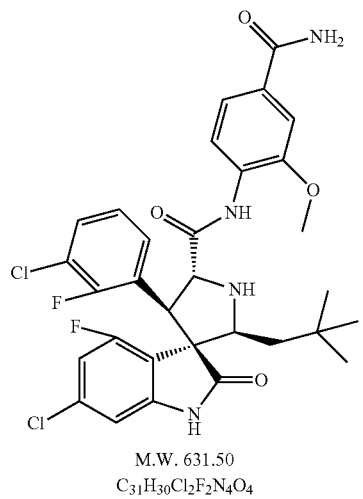

M.W. 631.50
$C_{31}H_{30}Cl_2F_2N_4O_4$

Rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-2-methoxy-phenyl)-amide prepared in Example 76 (0.18 g) was separated by chiral SFC chromatography to provide chiral (2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide as a white solid (56 mg, 31%) and chiral (2'R,3'S,4'R,5'S)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-phenyl)-amide as a white solid (52 mg, 29%).

Example 78

Preparation of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-2-fluoro-phenyl)-amide

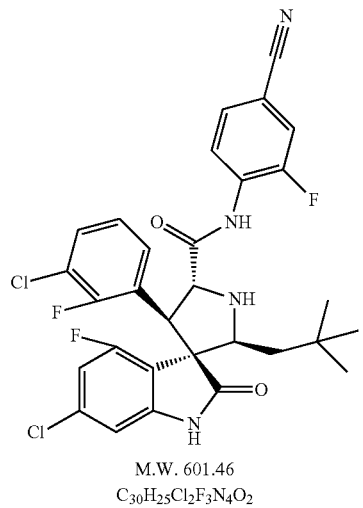

M.W. 601.46
$C_{30}H_{25}Cl_2F_3N_4O_2$

79

In a manner similar to the method described in Example 5, rac-(2'S,3'R,4'S,512)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid trifluoroacetic acid prepared in Example 71 (0.4 g, 0.69 mmol), was reacted with diisopropylethylamine (0.8 g, 6.2 mmol), diphenylphosphinic chloride (0.65 g, 2.8 mmol), then reacted with 4-amino-3-fluorobenzonitrile (Alfa) (0.094 g, 0.69 mmol) to give rac-(2'S,3'R,4'S,5'R)-6-chloro-4'-(3-chloro-2-fluorophenyl)-2'-(2,2-dimethyl-propyl)-4-fluoro-2-oxo-1,2-dihydro-spiro[indole-3,3'-pyrrolidine]-5'-carboxylic acid (4-cyano-2-fluoro-phenyl)-amide as a yellow solid (Yield 0.08 g, 19%).

MS (ES$^+$) m/z Calcd for $C_{30}H_{25}Cl_2F_3N_4O_2$+H [(M+H)$^+$]: 601, found: 601.

Example 79

Preparation of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-2-fluoro-phenyl)-amide

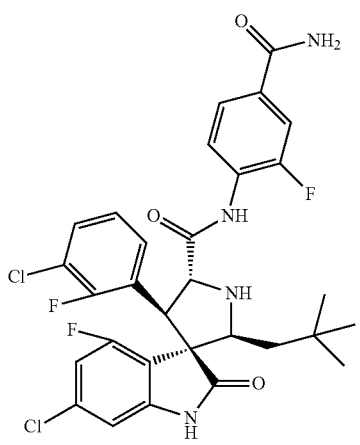

M.W. 619.47
$C_{30}H_{27}Cl_2F_3N_4O_3$

To the solution of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-2-fluoro-phenyl)-amide (0.08 g, 0.13 mmol) prepared in Example 78 in DMSO (2 mL) at 0° C. was added an aqueous solution (30% Aldrich) of $H_2O_2$ (0.23 g, 2 mmol), then aqueous solution (1N) of NaOH (0.7 mL, 0.7 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-carbamoyl-2-fluoro-phenyl)-amide as a white solid (Yield 0.02 g, 24%)

MS (ES$^+$) m/z Calcd for $C_{30}H_{27}Cl_2F_3N_4O_3$+H [(M+H)$^+$]: 619, found: 619.

80

Example 80

Preparation of intermediate E/Z-6-chloro-3-(3-chloro-4-fluoro-benzylidene)-1,3-dihydro-indol-2-one

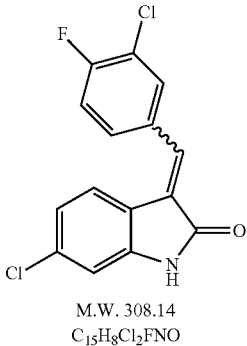

M.W. 308.14
$C_{15}H_8Cl_2FNO$

To the mixture of 6-chloro-2-oxindole (5.3 g, 32 mmol) (Crescent) and 3-chloro-4-fluorobenzaldehyde (5 g, 32 mmol) (Aldrich) in methanol (200 mL) was added piperidine (2.7 g, 32 mmol) (Aldrich) dropwise. The mixture was then heated at 50° C. for 3 h. After cooled to 4° C., the mixture was filtered and resulting precipitate was collected, dried to give E/Z-6-chloro-3-(3-chloro-4-fluoro-benzylidene)-1,3-dihydro-indol-2-one as a yellow solid (Yield 8 g, 82%).

Example 81

Preparation of intermediate rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid tert-butyl ester

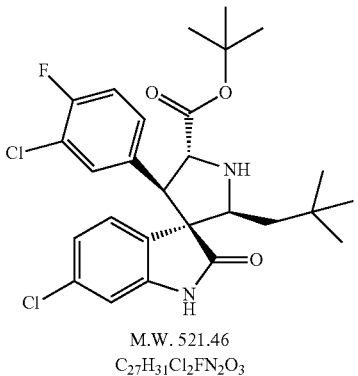

M.W. 521.46
$C_{27}H_{31}Cl_2FN_2O_3$

To a solution of [3,3-dimethyl-but-(E)-ylideneamino]-acetic acid tert-butyl ester (6 g, 28 mmol) prepared in Example 1 and E/Z-6-chloro-3-(3-chloro-4-fluoro-benzylidene)-1,3-dihydro-indol-2-one (5 g, 16 mmol) prepared in Example 80 in dichloromethane (100 mL) were added triethyl amine (15 mL, 109 mmol) and AgF (2.7 g, 218 mmol). The mixture was stirred at room temperature for 18 h. The mixture was concentrated, and the residue was partitioned between ethyl acetate and brine. The organic layer was separated, washed with water, dried over $MgSO_4$, and concentrated. The residue was dissolved into t-butanol (30 mL), and DBU (33 g, 130 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO₄, and concentrated. The residue was purified by chromatography (silica gel 120 g, 10-40% EtOAc in hexanes) to give as rac-(2'S,3'R,4'R,5'R)-6-chloro-4'-(3-chloro-4-fluoro-phenyl)-2'-(2,2-dimethyl-propyl)-2-oxo-1,2-dihydro-spiro [indole-3,3'-pyrrolidine]-5'-carboxylic acid tert-butyl ester as a off white solid (2.4 g, 28%)

Example 82

Preparation of intermediate rac-(2'S,3'R,4'S,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid trifluoroacetic acid

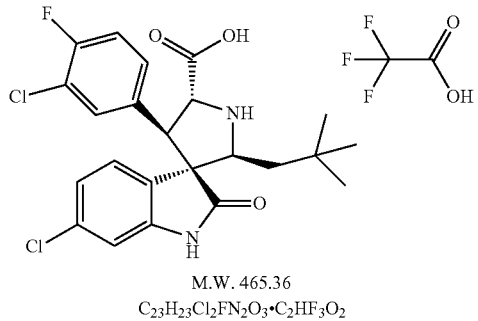

M.W. 465.36
$C_{23}H_{23}Cl_2FN_2O_3 \cdot C_2HF_3O_2$

A solution of rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid tert-butyl ester (1 g, 1.9 mmol) in dichloromethane (12 mL) was added trifluoroacetic acid (4 g). The reaction mixture was stirred at room temperature for 20 h, then concentrated. The residue was then triturated with ethyl ether hexanes, concentrated, dried in vacuo to give rac-(2'S,3'R,4'S,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid trifluoroacetic acid as a off white solid (1.1 g, 99%).

Example 83

Preparation of rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide

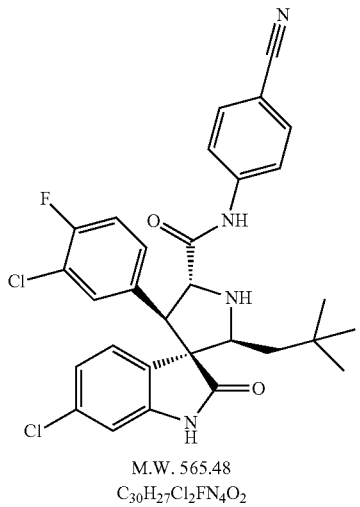

M.W. 565.48
$C_{30}H_{27}Cl_2FN_4O_2$

In a manner similar to the method described in Example 5, rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 82 (0.4 g, 0.71 mmol), was reacted with diisopropylethylamine (0.82 g, 6.4 mmol), diphenylphosphinic chloride (0.67 g, 2.8 mmol), then reacted with 4-aminobenzonitrile (Aldrich) (0.34 g, 2.8 mmol) to give rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a white foam (Yield, 0.18 g, 45%).

MS (ES⁺) m/z Calcd for $C_{30}H_{27}Cl_2FN_4O_2$+H [(M+H)⁺]: 565; found: 565.

Example 84

Preparation of rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

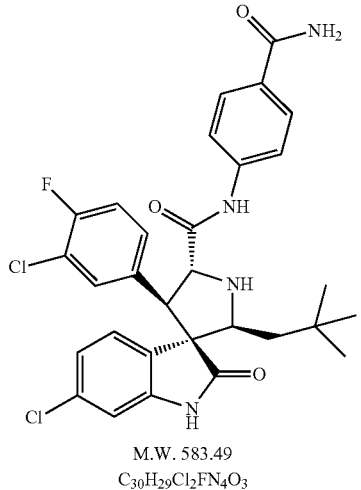

M.W. 583.49
$C_{30}H_{29}Cl_2FN_4O_3$

To the solution of rac-(2'S,3'R,4'R,5'R)-6-chloro-4'-(3-chloro-4-fluoro-phenyl)-2'-(2,2-dimethyl-propyl)-2-oxo-1, 2-dihydro-spiro[indole-3,3'-pyrrolidine]-5'-carboxylic acid (4-cyano-phenyl)-amide (0.17 g, 0.3 mmol) prepared in Example 83 in DMSO (1 mL) at 0° C. was added an aqueous solution (30% Aldrich) of H₂O₂ (0.5 g, 4.5 mmol), then aqueous solution (1N) of NaOH (1.5 mL, 1.5 mmol) was added dropwise. The reaction mixture was stirred at 10° C. for 1 h. The mixture was partitioned between ethyl acetate and saturated aqueous Na₂SO₃ solution.

The organic layer was separated, washed with water, brine, dried over MgSO₄, and concentrated to give rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (Yield 0.15 g, 86%)

MS (ES⁺) m/z Calcd for $C_{30}H_{29}Cl_2FN_4O_3$+H [(M+H)⁺]: 583, found: 583.

Example 85

Preparation of intermediate E/Z-6-chloro-3-(3-chloro-5-fluoro-benzylidene)-1,3-dihydro-indol-2-one

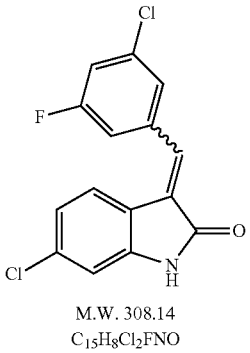

M.W. 308.14
C$_{15}$H$_8$Cl$_2$FNO

To the mixture of 6-chloro-2-oxindole (4.4 g, 26 mmol) (Crescent) and 3-chloro-5-fluorobenzaldehyde (4.2 g, 26 mmol) (Aldrich) in methanol (200 mL) was added piperidine (2.3 g, 26 mmol) (Aldrich) dropwise. The mixture was then heated at 80° C. for 2 h. After cooled to 4° C., the mixture was filtered and resulting precipitate was collected, dried to give E/Z-6-chloro-3-(3-chloro-5-fluoro-benzylidene)-1,3-dihydro-indol-2-one as a yellow solid (Yield 7.5 g, 92%).

Example 86

Preparation of intermediate rac-(2'S,3'R,4'S,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid tert-butyl ester

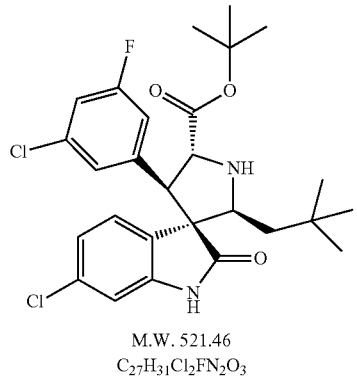

M.W. 521.46
C$_{27}$H$_{31}$Cl$_2$FN$_2$O$_3$

To a solution of [3,3-dimethyl-but-(E)-ylideneamino]-acetic acid tert-butyl ester (6 g, 28 mmol) prepared in Example 1 and E/Z-6-chloro-3-(3-chloro-5-fluoro-benzylidene)-1,3-dihydro-indol-2-one (5 g, 16 mmol) prepared in Example 85 in dichloromethane (200 mL) were added triethyl amine (15 mL, 109 mmol) and AgF (2.7 g, 218 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into t-butanol (30 mL), and DBU (33 g, 130 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (silica gel 120 g, 10-40% EtOAc in hexanes) to give as rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid tert-butyl ester a light yellow solid (1.5 g, 18%)

Example 87

Preparation of intermediate rac-(2'S,3'R,4'S,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid trifluoracetic acid

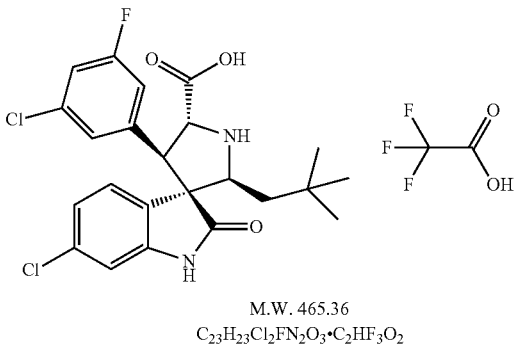

M.W. 465.36
C$_{23}$H$_{23}$Cl$_2$FN$_2$O$_3$·C$_2$HF$_3$O$_2$

A solution of rac-(2'S,3'R,4'S,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid tert-butyl ester (1.5 g, 2.9 mmol) in dichloromethane (18 mL) was added trifluoroacetic acid (7 g). The reaction mixture was stirred at room temperature for 20 h, then concentrated. The residue was then triturated with ethyl ether hexanes, concentrated, dried in vacuo to give rac-(2'S,3'R,4'S,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid trifluoroacetic acid as a white solid (1.6 g, 96%).

Example 88

Preparation of rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide

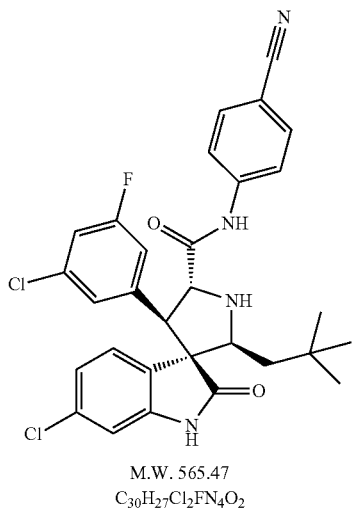

M.W. 565.47
C$_{30}$H$_{27}$Cl$_2$FN$_4$O$_2$

85

In a manner similar to the method described in Example 5, rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 87 (0.4 g, 0.71 mmol), was reacted with diisopropylethylamine (0.82 g, 6.4 mmol), diphenylphosphinic chloride (0.67 g, 2.8 mmol), then reacted with 4-aminobenzonitrile (Aldrich) (0.34 g, 2.8 mmol) to give rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a white solid (Yield, 0.14 g, 55%).

HRMS (ES$^+$) m/z Calcd for $C_{30}H_{27}Cl_2FN_4O_2$+H [(M+H)$^+$]: 565, found: 565.

Example 89

Preparation of rac-(2'S,3'R,4'S,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

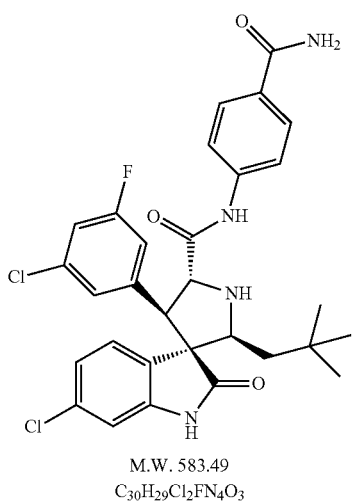

M.W. 583.49
$C_{30}H_{29}Cl_2FN_4O_3$

To the solution of rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide (0.12 g, 0.2 mmol) prepared in Example 88 in DMSO (1 mL) at 0° C. was added an aqueous solution (30% Aldrich) of $H_2O_2$ (0.36 g, 3.2 mmol), then aqueous solution (1N) of NaOH (1.1 mL, 1.1 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over MgSO$_4$, and concentrated to give rac-(2'S,3'R,4'S,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (Yield 66 mg, 53%)

MS (ES$^+$) m/z Calcd for $C_{30}H_{29}Cl_2FN_4O_3$+H [(M+H)$^{30}$]: 583, found: 583.

Example 90

Preparation of intermediate E/Z-6-bromo-3-(3-chloro-2-fluoro-benzylidene)-1,3-dihydro-indol-2-one

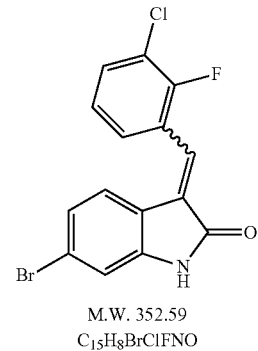

M.W. 352.59
$C_{15}H_8BrClFNO$

To the mixture of 6-bromo-2-oxindole (5 g, 24 mmol) (Combi-blocks) and 3-chloro-2-fluorobenzaldehyde (3.7 g, 24 mmol) (Oakwood) in methanol (200 mL) was added piperidine (2 g, 24 mmol) (Aldrich) dropwise. The mixture was then heated at 80° C. for 2 h. After cooled to 4° C., the mixture was filtered and resulting precipitate was collected, dried to give E/Z-6-bromo-3-(3-chloro-2-fluoro-benzylidene)-1,3-dihydro-indol-2-one as a yellow solid (Yield 7.8 g, 94%).

Example 91

Preparation of intermediate rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester

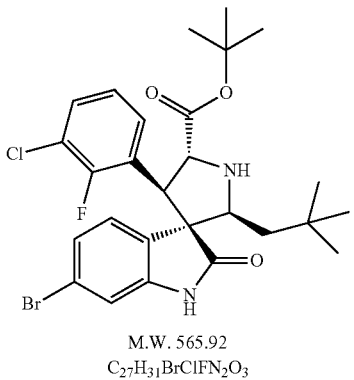

M.W. 565.92
$C_{27}H_{31}BrClFN_2O_3$

To a solution of [3,3-dimethyl-but-(E)-ylideneamino]-acetic acid tert-butyl ester (6 g, 28 mmol) prepared in Example 1 and E/Z-6-bromo-3-(3-chloro-2-fluoro-benzylidene)-1,3-dihydro-indol-2-one (6 g, 17 mmol) prepared in Example 90 in dichloromethane (200 mL) were added triethylamine (15 mL, 114 mmol) and AgF (2.8 g, 22 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into t-butanol (30 mL), and DBU (34 g, 138 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO₄, and concentrated. The residue was purified by chromatography (10-40% EtOAc in hexanes) to give as rac-(2'S, 3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester a light yellow solid (1.4 g, 15%)

Example 92

Preparation of intermediate rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoracetic acid

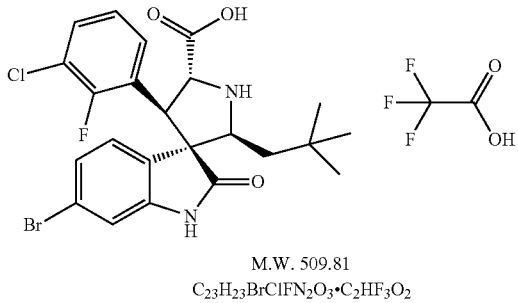

M.W. 509.81
$C_{23}H_{23}BrClFN_2O_3 \cdot C_2HF_3O_2$

A solution of rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester (1.4 g, 2.5 mmol) in dichloromethane (18 mL) was added trifluoroacetic acid (6 g). The reaction mixture was stirred at room temperature for 20 h, then concentrated. The residue was then triturated with ethyl ether hexanes, concentrated, dried in vacuo to give rac-(2'S,3'R,4'S,5'S)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid as a light yellow solid (1.5 g, 97%).

Example 93

Preparation of rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide

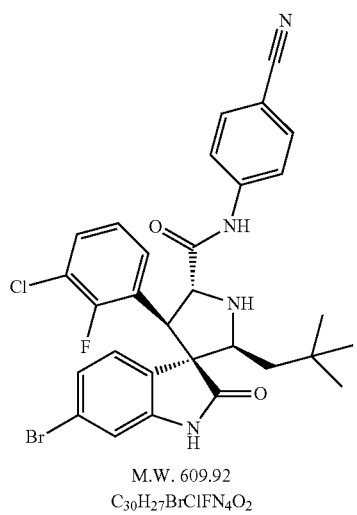

M.W. 609.92
$C_{30}H_{27}BrClFN_4O_2$

In a manner similar to the method described in Example 5, rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 92 (0.4 g, 0.66 mmol), was reacted with diisopropylethylamine (0.77 g, 5.9 mmol), diphenylphosphinic chloride (0.62 g, 2.6 mmol), then reacted with 4-aminobenzonitrile (Aldrich) (0.31 g, 2.6 mmol) to give rac-(2'S, 3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a off white foam (Yield 0.18 g, 45%).

MS (ES⁺) m/z Calcd for $C_{30}H_{27}BrClFN_4O_2+H$ [(M+H)⁺]: 609, found: 609.

Example 94

Preparation of rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide

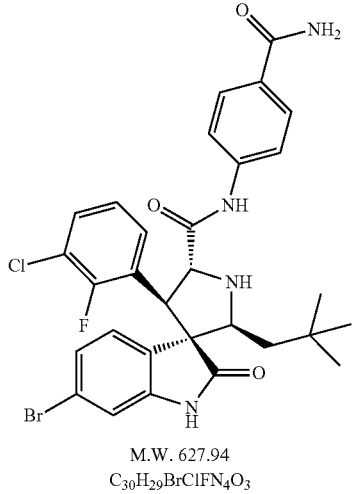

M.W. 627.94
$C_{30}H_{29}BrClFN_4O_3$

To the solution of rac-(2'S,3'R,4'S,5'R)-6-bromo-4'-(3-chloro-2-fluoro-phenyl)-2'-(2,2-dimethyl-propyl)-2-oxo-1, 2-dihydro-spiro[indole-3,3'-pyrrolidine]-5'-carboxylic acid (4-cyano-phenyl)-amide (0.16 g, 0.26 mmol) prepared in Example 93 in DMSO (1 mL) at 0° C. was added an aqueous solution (30% Aldrich) of $H_2O_2$ (0.45 g, 3.9 mmol), then aqueous solution (1N) of NaOH (1.3 mL, 1.3 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over MgSO₄, and concentrated. The residue was triturated with dichlormethane and hexanes to give rac-(2'S,3'R,4'S,5'R)-6-bromo-4'-(3-chloro-2-fluoro-phenyl)-2'-(2,2-dimethyl-propyl)-2-oxo-1, 2-dihydro-spiro[indole-3,3'-pyrrolidine]-5'-carboxylic acid (4-carbamoyl-phenyl)-amide as a white solid (Yield 0.13 g, 76%)

MS (ES⁺) m/z Calcd for $C_{30}H_{29}BrClFN_4O_3+H$ [(M+H)⁺]: 627, found: 627.

Example 95

Preparation of intermediate E/Z-3-(3-bromo-2-fluoro-benzylidene)-6-chloro-1,3-dihydro-indol-2-one

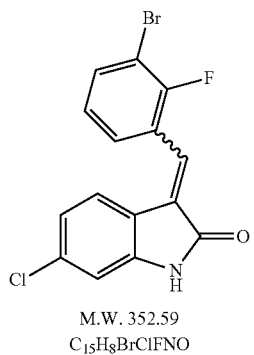

M.W. 352.59
C₁₅H₈BrClFNO

To the mixture of 6-chloro-2-oxindole (3.9 g, 23 mmol) (Alfa) and 3-bromoo-2-fluorobenzaldehyde (4.7 g, 23 mmol) (Oakwood) in methanol (200 mL) was added piperidine (2 g, 24 mmol) (Aldrich) dropwise. The mixture was then heated at 80° C. for 2 h. After cooled to 4° C., the mixture was filtered and resulting precipitate was collected, dried to give E/Z-3-(3-bromo-2-fluoro-benzylidene)-6-chloro-1,3-dihydro-indol-2-one as a yellow solid (Yield 7.5 g, 92%).

Example 96

Preparation of intermediate rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid tert-butyl ester

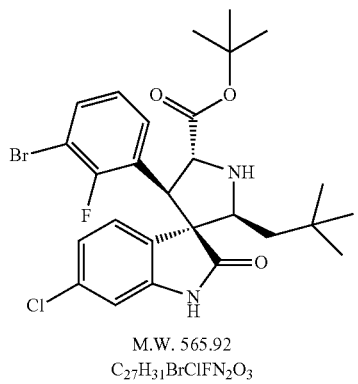

M.W. 565.92
C₂₇H₃₁BrClFN₂O₃

To a solution of [3,3-dimethyl-but-(E)-ylideneamino]-acetic acid tert-butyl ester (5.9 g, 28 mmol) prepared in Example 1 and E/Z-3-(3-bromo-2-fluoro-benzylidene)-6-chloro-1,3-dihydro-indol-2-one (5.3 g, 15 mmol) prepared in Example 95 in dichloromethane (200 mL) were added triethylamine (14 mL, 101 mmol) and AgF (2.5 g, 20 mmol). The mixture was stirred at room temperature for 18 h. The mixture was concentrated, and the residue was partitioned between ethyl acetate and brine. The organic layer was separated, washed with water, dried over MgSO₄, and concentrated. The residue was dissolved into t-butanol (30 mL), and DBU (30 g, 120 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO₄, and concentrated. The residue was purified by chromatography (10-40% EtOAc in hexanes) to give as rac-(2'S, 3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid tert-butyl ester a light yellow solid (1.2 g, 14%)

Example 97

Preparation of intermediate rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid trifluoroacetic acid

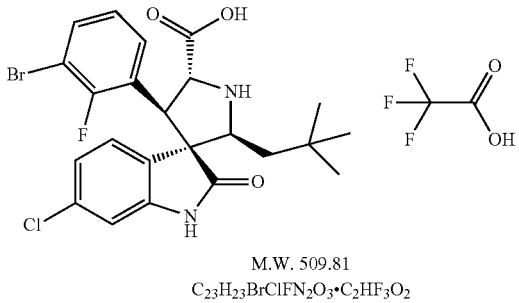

M.W. 509.81
C₂₃H₂₃BrClFN₂O₃·C₂HF₃O₂

A solution of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid tert-butyl ester (1.2 g, 2.1 mmol) in dichloromethane (15 mL) was added trifluoroacetic acid (5 g). The reaction mixture was stirred at room temperature for 20 h, then concentrated. The residue was then triturated with ethyl ether hexanes, concentrated, dried in vacuo to give rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid trifluoroacetic acid as a light yellow solid (1.3 g, 98%).

Example 98

Preparation of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-phenyl)-amide

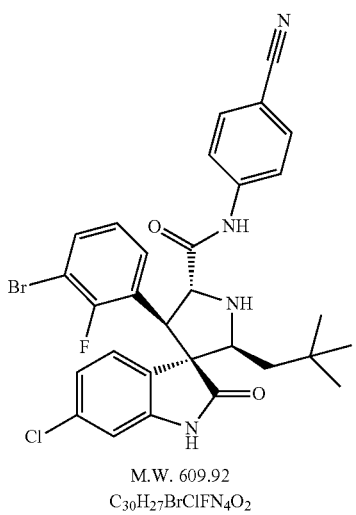

M.W. 609.92
C₃₀H₂₇BrClFN₄O₂

In a manner similar to the method described in Example 5, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid trifluoroacetic acid prepared in Example 97 (0.4 g, 0.66 mmol), was reacted with diisopropylethylamine (0.77 g, 5.9 mmol), diphenylphosphinic chloride (0.62 g, 2.6 mmol), then reacted with 4-aminobenzonitrile (Aldrich) (0.31 g, 2.6 mmol) to give rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-phenyl)-amide as a white foam (Yield 0.18 g, 45%).

MS (ES$^+$) m/z Calcd for $C_{30}H_{27}BrClFN_4O_2$+H [(M+H)$^+$]: 609, found: 609.

Example 99

Preparation of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-phenyl)-amide

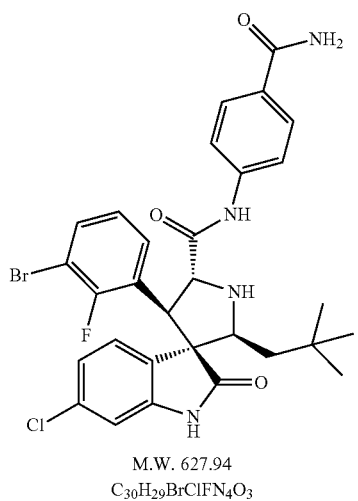

M.W. 627.94
$C_{30}H_{29}BrClFN_4O_3$

To the solution of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-phenyl)-amide (0.16 g, 0.26 mmol) prepared in Example 98 in DMSO (1 mL) at 0° C. was added an aqueous solution (30% Aldrich) of $H_2O_2$ (0.45 g, 3.9 mmol), then aqueous solution (1N) of NaOH (1.3 mL, 1.3 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over $MgSO_4$, and concentrated. The residue was triturated with dichlormethane and hexanes to give rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-phenyl)-amide as a white solid (Yield 0.14 g, 85%)

MS (ES$^+$) m/z Calcd for $C_{30}H_{29}BrClFN_4O_3$+H [(M+H)$^+$]: 627, found: 627.

Example 100

Preparation of intermediate [4-(tert-butyl-dimethyl-silanyloxy)-3,3-dimethyl-but-(E)-ylideneamino]-acetic acid tert-butyl ester

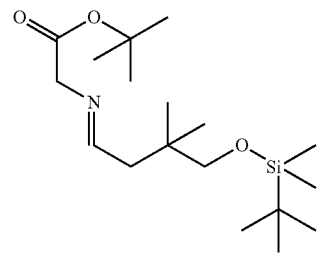

M.W. 343.59
$C_{18}H_{37}NO_3Si$

Step A
A mixture of 2,2-dimethyl-propane-1,3-diol (Aldrich) (10 g, 96 mmol) and imidazole (9.8 g, 140 mmol) in dichloromethane (200 mL) was added tert-butyldimethylchlorosilane (15.9 g, 10.6 mmol). The reaction mixture was stirred at room temperature for 0.5 h. Water was added. The organic layer was separated, the aqueous layer was then extracted with dichloromethane. The combined organic layers were washed with brine, dried over $MgSO_4$, concentrated to give 3-(tert-butyl-dimethyl-silanyloxy)-2,2-dimethyl-propan-1-ol as a colorless oil (20.4 g, 97%).

Step B
To the solution of 3-(tert-butyl-dimethyl-silanyloxy)-2,2-dimethyl-propan-1-ol (20.4 g, 93 mmol) and triethylamine (26 g, 186 mmol) in dichloromethane (200 mL) at 0° C. was added a dichlormethane solution (20 mL) of methanesulfonyl chloride (Aldrich) (8.69 mL, 112 mmol). The reaction mixture was stirred at 0° C. for 2 h. Water was added. Organic layer was separated, the aqueous layer was extracted with dichlormethane. The combined organic layers were washed with diluted aqueous HCl solution, saturated aqueous $NaHCO_3$ solution, brine, dried over $MgSO_4$, and concentrated to give methanesulfonic acid 3-(tert-butyl-dimethyl-silanyloxy)-2,2-dimethyl-propyl ester as a yellow oil (24 g, 87%).

Step C
To the solution of methanesulfonic acid 3-(tert-butyl-dimethyl-silanyloxy)-2,2-dimethyl-propyl ester (5 g, 16.8 mmol) in anhydrous dimethyl sulfoxide (50 mL) was added KCN (2.85 g, 44 mmol). The reaction mixture was heated at 120° C. for 16 h. The mixture was cooled, and water was added. The mixture was extracted with ethyl acetate twice. The combined organic layers were washed with saturated aqueous $NaHCO_3$ solution, brine, dried over $MgSO_4$, and concentrated. The residue was purified by chromatography (EtOAc:hexanes=1; 4) to give 4-(tert-butyl-dimethyl-silanyloxy)-3,3-dimethyl-butyronitrile as a yellow oil (2.2 g, 57%).

Step D
To a solution of 4-(tert-butyl-dimethyl-silanyloxy)-3,3-dimethyl-butyronitrile (2.2 g, 9.67 mmol) (Aldrich) in dichloromethane (20 mL) at −78° C. was added a toluene solution (1M) of DIBAL (10.6 mL, 10.6 mmol) dropwise. The reaction mixture was stirred at 0° C. for 3 h. The mixture was poured into aqueous saturated NH₄Cl solution. The organic layer was separated, and the aqueous layer was extracted with ethyl acetate. The organic layers were combined, washed with brine, dried over MgSO₄, and concentrated. The residue was purified by chromatography (EtOAc:hexanes=1:4) to give 4-(tert-butyl-dimethyl-silanyloxy)-3,3-dimethyl-butyraldehyde as a colorless oil (Yield: 0.84 g, 38%).

Step E

In a manner similar to the method described in Example 1, glycine tert-butyl ester (0.52 g, 3.64 mmol) was reacted with 4-(tert-butyl-dimethyl-silanyloxy)-3,3-dimethyl-butyraldehyde (0.84 g, 3.64 mmol) in CH₂Cl₂ at room temperature for 18 h to give [4-(tert-butyl-dimethyl-silanyloxy)-3,3-dimethyl-but-(E)-ylideneamino]-acetic acid tert-butyl ester as a colorless oil (1.25 g, 100%).

Example 101

Preparation of intermediate rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid tert-butyl ester

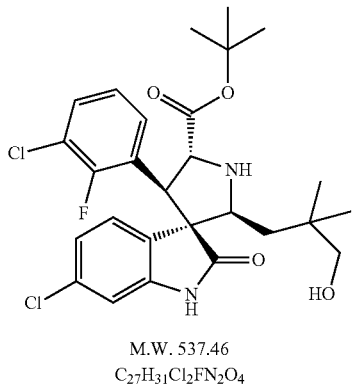

M.W. 537.46
C₂₇H₃₁Cl₂FN₂O₄

To a solution of [4-(tert-butyl-dimethyl-silanyloxy)-3,3-dimethyl-but-(E)-ylideneamino]-acetic acid-tert-butyl ester (3.1 g, 9.0 mmol) prepared in Example 100 and E/Z-6-chloro-3-(3-chloro-2-fluoro-benzylidene)-1,3-dihydro-indol-2-one (2.5 g, 8.1 mmol) prepared in Example 2 in dichloromethane (100 mL) were added triethylamine (7.5 mL, 54 mmol) and AgF (1.9 g, 15 mmol). The mixture was stirred at room temperature for 18 h. The mixture was concentrated, and the residue was partitioned between ethyl acetate and brine. The organic layer was separated, washed with water, dried over MgSO₄, and concentrated. The residue was dissolved into t-butanol (15 mL), and DBU (16 g, 65 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO₄, and concentrated. The residue was purified by chromatography (10-80% EtOAc in hexanes) to give as rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid tert-butyl ester a light yellow solid (1.0 g, 23%)

Example 102

Preparation of intermediate rac-(2'S,3'R,4'S,5'R)-2'-(3-acetoxy-2,2-dimethyl-propyl)-6-chloro-4'-(3-chloro-2-fluoro-phenyl)-2-oxo-1,2-dihydro-spiro[indole-3,3'-pyrrolidine]-5'-carboxylic acid tert-butyl ester

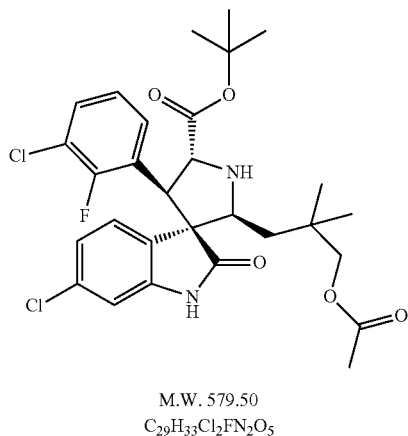

M.W. 579.50
C₂₉H₃₃Cl₂FN₂O₅

To a solution of rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid tert-butyl ester (0.3 g, 0.56 mmol) in tetrahydrofuran (2 mL) at 0° C. was added pyridine (44 mg, 0.56 mmol) and acetyl chloride (44 mg, 0.56 mmol). The mixture was stirred at room temperature for 1 h. The mixture was concentrated, and the residue was partitioned between ethyl acetate and water. The organic layer was separated, washed with water, saturated aqueous CuSO₄, brine, dried over MgSO₄, and concentrated to give as rac-(2'S,3'R,4'S,5'R)-2'-(3-acetoxy-2,2-dimethyl-propyl)-6-chloro-4'-(3-chloro-2-fluoro-phenyl)-2-oxo-1,2-dihydro-spiro[indole-3,3'-pyrrolidine]-5'-carboxylic acid tert-butyl ester as a yellow oil (0.24 g, 74%)

Example 103

Preparation of intermediate rac-(2'S,3'R,4'S,5'R)-2'-(3-acetoxy-2,2-dimethyl-propyl)-6-chloro-4'(3-chloro-2-fluoro-phenyl)-2-oxo-1,2-dihydro-spiro[indole-3,3'-pyrrolidine]-5'-carboxylic acid trifluoroacetic acid

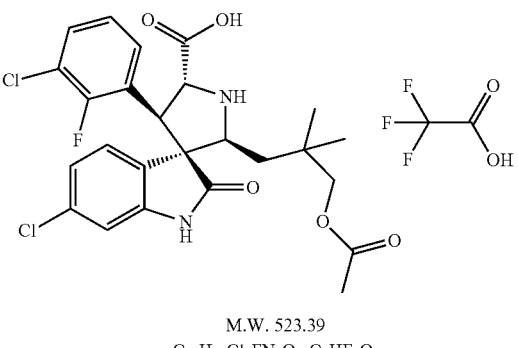

M.W. 523.39
C₂₅H₂₅Cl₂FN₂O₅·C₂HF₃O₂

A solution of rac-(2'S,3'R,4'S,5'R)-2'-(3-acetoxy-2,2-dimethyl-propyl)-6-chloro-4'-(3-chloro-2-fluoro-phenyl)-2-oxo-1,2-dihydro-spiro[indole-3,3'-pyrrolidine]-5'-carboxylic acid tert-butyl ester (0.24 g, 0.41 mmol) in dichloromethane (2 mL) was added trifluoroacetic acid (1 g). The reaction mixture was stirred at room temperature for 18 h, then concentrated. The residue was then triturated with ethyl ether hexanes, concentrated, dried in vacuo to give rac-(2'S,3'R,4'S,5'R)-2'-(3-acetoxy-2,2-dimethyl-propyl)-6-chloro-4'-(3-chloro-2-fluoro-phenyl)-2-oxo-1,2-dihydro-spiro[indole-3,3'-pyrrolidine]-5'-carboxylic acid trifluoroacetic acid as a yellow solid (0.25 g, 97%).

Example 104

Preparation of acetic acid rac-3-[(2'S,3'R,4'S,5'R)-6-chloro-4'-(3-chloro-2-fluoro-phenyl)-5'-(4-cyano-phenylcarbamoyl)-2-oxo-1,2-dihydro-spiro[indole-3,3'-pyrrolidin]-2'-yl]-2,2-dimethyl-propyl ester

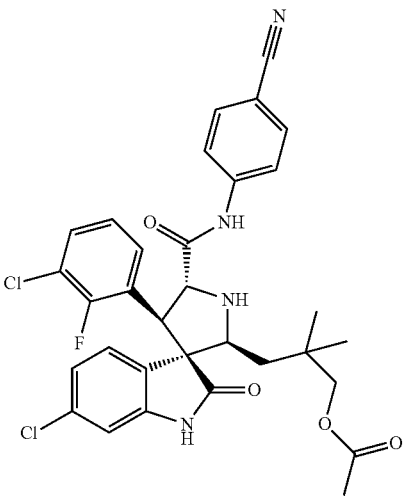

M.W. 623.51
$C_{32}H_{29}Cl_2FN_4O_4$

In a manner similar to the method described in Example 5, rac-(2'S,3'R,4'S,5'R)-2'-(3-acetoxy-2,2-dimethyl-propyl)-6-chloro-4'-(3-chloro-2-fluoro-phenyl)-2-oxo-1,2-dihydro-spiro[indole-3,3'-pyrrolidine]-5'-carboxylic acid trifluoroacetic acid prepared in Example 103 (0.25 g, 0.4 mmol), was reacted with diisopropylethylamine (0.47 g, 3.6 mmol), diphenylphosphinic chloride (0.38 g, 1.6 mmol), then reacted with 4-aminobenzonitrile (Aldrich) (0.19 g, 1.6 mmol) to give acetic acid rac-3-[(2'S,3'R,4'S,5'R)-6-chloro-4'-(3-chloro-2-fluoro-phenyl)-5'-(4-cyano-phenylcarbamoyl)-2-oxo-1,2-dihydro-spiro[indole-3,3'-pyrrolidin]-2'-yl]-2,2-dimethyl-propyl ester as a light yellow foam (Yield 0.1 g, 40%).

HRMS (ES+) m/z Calcd for $C_{32}H_{29}Cl_2FN_4O_4$+H [(M+H)+]: 623.1623, found: 623.1620.

Example 105

Preparation of rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid (4-cyano-phenyl)-amide

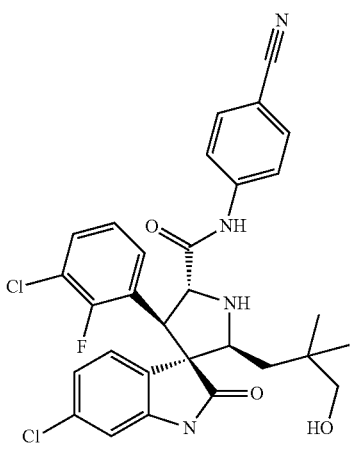

M.W. 581.47
$C_{30}H_{27}Cl_2FN_4O_3$

To a solution of acetic acid rac-3-[(2'S,3'R,4'S,5'R)-6-chloro-4'-(3-chloro-2-fluoro-phenyl)-5'-(4-cyano-phenylcarbamoyl)-2-oxo-1,2-dihydro-spiro[indole-3,3'-pyrrolidin]-2'-yl]-2,2-dimethyl-propyl ester (17 mg, 0.027 mmol) in tetrahydrofuran (2 mL) was added an aqueous solution (1N) of NaOH (0.5 mL, 0.5 mmol) and methanol (0.2 mL). The reaction mixture was stirred at room temperature for 18 h. The mixture was concentrated, and the residue was partitioned between ethyl acetate and water. The organic layer was separated, and the aqueous layer was extracted with ethyl acetate twice. The organic extracts were combined, washed with water, brine, dried over MgSO4, and concentrated to give rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid (4-cyano-phenyl)-amide as a off white solid (14 mg, 88%).

HRMS (ES+) m/z Calcd for $C_{30}H_{27}Cl_2FN_4O_3$+H [(M+H)+]: 581.1517, found: 581.1518.

Example 106

Preparation of rac-(2'S,3'R,4'S,5'R)-6-chloro-4'-(3-chloro-2-fluoro-phenyl)-2'43-hydroxy-2,2-dimethyl-propyl)-2-oxo-1,2-dihydro-spiro[indole-3,3'-pyrrolidine]-5'-carboxylic acid (4-carbamoyl-phenyl)-amide

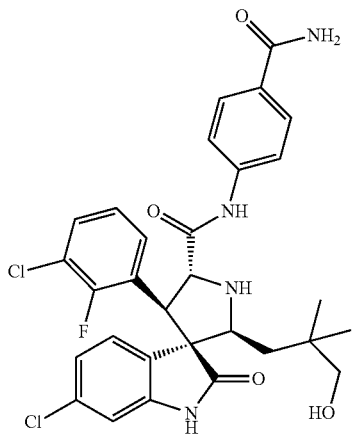

M.W. 599.49
C30H29Cl2FN4O4

To the solution of acetic acid rac-3-[(2'S,3'R,4'S,5'R)-6-chloro-4'-(3-chloro-2-fluoro-phenyl)-5'-(4-cyano-phenyl-carbamoyl)-2-oxo-1,2-dihydro-spiro[indole-3,3'-pyrrolidin]-2'-yl]-2,2-dimethyl-propyl ester prepared in Example 104 (80 mg, 0.13 mmol) in DMSO (0.5 mL) at 0° C. was added an aqueous solution (30% Aldrich) of $H_2O_2$ (0.22 g, 1.9 mmol), then aqueous solution (1N) of NaOH (0.64 mL, 0.64 mmol) was added dropwise. The reaction mixture was stirred at room temperature for 5 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50 to 100% EtOAc in $CH_2Cl_2$) to give rac-(2'S,3'R,4'S,5'R)-6-chloro-4'-(3-chloro-2-fluoro-phenyl)-2'43-hydroxy-2,2-dimethyl-propyl)-2-oxo-1,2-dihydro-spiro[indole-3,3'-pyrrolidine]-5'-carboxylic acid (4-carbamoyl-phenyl)-amide as a white solid (Yield 73 mg, 95%)

HRMS (ES+) m/z Calcd for $C_{30}H_{29}Cl_2FN_4O_4$+H [(M+H)+]: 599.1623, found: 599.1621.

Example 107

Preparation of rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester

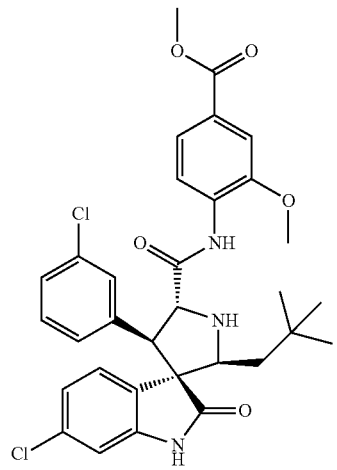

M.W. 610.54
C32H33Cl2N3O5

In a manner similar to the method described in Example 5, rac-(2'S,3'R,4'S,5'R)-6-chloro-4'-(3-chloro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 63 (0.28 g, 0.5 mmol), was reacted with diisopropylethylamine (0.38 mL, 2.25 mmol), diphenylphosphinic chloride (0.36 mL, 1.9 mmol), then reacted with methyl 4-amino-3-methoxy-benzoate (Ark Pharm) (0.09 g, 0.5 mmol) to give rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester as a white solid (Yield, 102 mg, 33%). MS (H+), 610.

Example 108

Preparation of rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]amino}-3-methoxy-benzoic acid

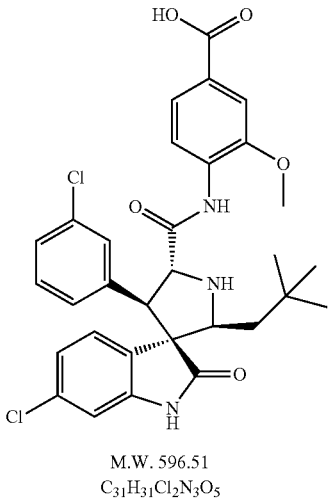

M.W. 596.51
$C_{31}H_{31}Cl_2N_3O_5$

To a stirred solution of rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester (100 mg, 0.16 mmol) in methanol (10 mL) was added an aqueous solution (2 mL) of NaOH (33 mg, 0.82 mmol). The reaction mixture was stirred at room temperature overnight. The "pH" of the mixture was adjusted to 4.5, and the solvent was reduced to about 3 ml. The mixture was filtered, and the precipitate was collected, dried to give a white solid, which was purified by chromatography (7%-10% methanol/methylene chloride) to give 20 mg desired product. MS (H+), 596.

Example 109

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester

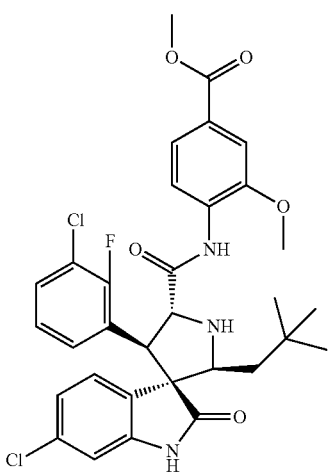

M.W. 628.53
$C_{32}H_{32}Cl_2FN_3O_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.5 g, 0.86 mmol), was reacted with diisopropylethylamine (0.45 g, 3.5 mmol), diphenylphosphinic chloride (0.45 g, 1.9 mmol), then reacted with methyl 4-amino-3-methoxy-benzoate (Ark Pharm) (0.16 g, 0.9 mmol) to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester as a white solid (Yield, 195 mg, 35%). MS (H+), 628.

Example 110

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid

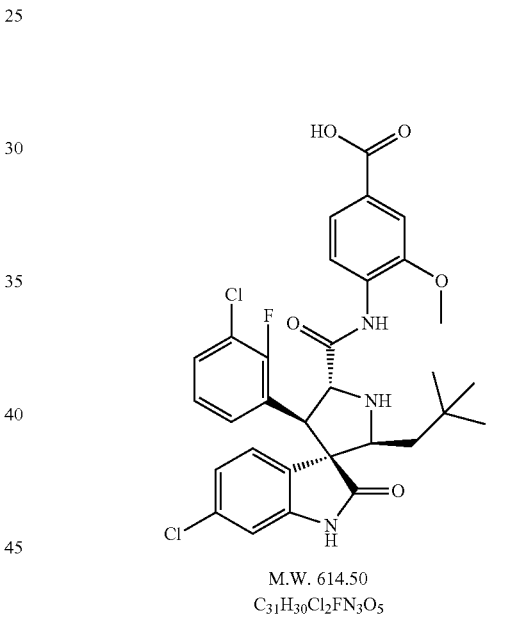

M.W. 614.50
$C_{31}H_{30}Cl_2FN_3O_5$

To a solution of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester (60 mg, 0.096 mmol) in MeOH (4 mL) and THF (6 mL) was added an aqueous solution (2 N) of NaOH (1.2 mL, 2.4 mmol). The reaction mixture was heated to 40° C. and stirred overnight. The crude mixture was diluted with water (5 mL), concentrated in vacuo to remove some organic solvent. The mixture was filtered, and the filtrate was acidified to "pH" 5-6. The suspension was filtered and the solid was collected, washed with water, and dried to give the desired product as a white powder (Yield, 41 mg, 66%). MS (H+), 614.

Example 111

Preparation of chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid

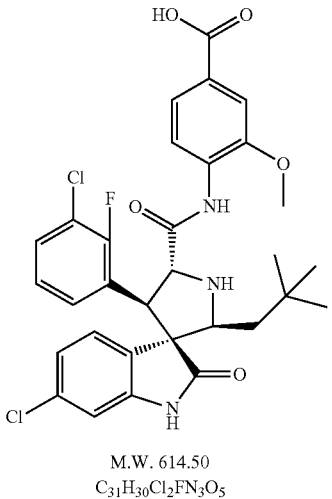

M.W. 614.50
C₃₁H₃₀Cl₂FN₃O₅

Rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid (0.16 g) was separated by chiral SFC chromatography to provide chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid as a white solid (57 mg, 37%) and chiral 4-{[(2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid as a white solid (55 mg, 36%).

Example 112

Preparation of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-2-methoxy-phenyl)-amide

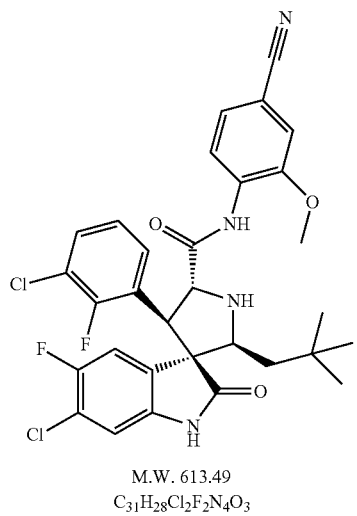

M.W. 613.49
C₃₁H₂₈Cl₂F₂N₄O₃

In a manner similar to the method described in Example 5, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid trifluoroacetic acid prepared in Example 47 (0.7 g, 1.2 mmol), was reacted with diisopropylethylamine (0.78 g, 6.0 mmol), diphenylphosphinic chloride (0.57 g, 2.4 mmol), then reacted with 4-amino-3-methoxy-benzonitrile prepared in Example 57 (0.54 g, 3.6 mmol) to give rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-2-methoxy-phenyl)-amide as a off white solid (Yield 0.24 g, 33%).

HRMS (ES⁺) m/z, Calcd for $C_{31}H_{28}Cl_2F_2N_4O_3$+H [(M+H)⁺]: 613.1580, found: 613.1579.

Example 113

Preparation of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-2-methoxy-phenyl)-amide

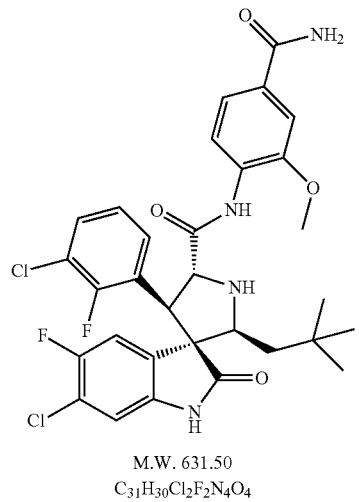

M.W. 631.50
C₃₁H₃₀Cl₂F₂N₄O₄

To the solution of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-2-methoxy-phenyl)-amide (0.23 g, 0.38 mmol) prepared in Example 112 in DMSO (2 mL) at 0° C. was added an aqueous solution (30% Aldrich) of H₂O₂ (0.64 g, 5.6 mmol), then aqueous solution (1N) of NaOH (1.9 mL, 1.9 mmol) was added dropwise. The reaction mixture was stirred at 10° C. for 1 h. The mixture was partitioned between ethyl acetate and saturated aqueous Na₂SO₃ solution. The organic layer was separated, washed with water, brine, dried over MgSO₄, and concentrated. The residue was triturated with dichloromethane and hexanes to give rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-2-methoxy-phenyl)-amide as a white solid (Yield 0.17 g, 72%)

HRMS (ES⁺) m/z Calcd for C₃₁H₃₀Cl₂F₂N₄O₄+H [(M+H)⁺]: 631.1685, found: 631.1686.

Example 114

Preparation of rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide

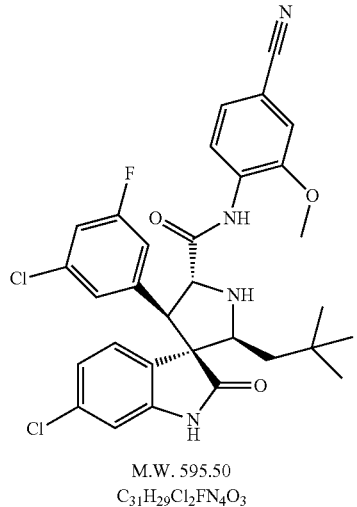

M.W. 595.50
C₃₁H₂₉Cl₂FN₄O₃

In a manner similar to the method described in Example 5, rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 87 (0.4 g, 0.71 mmol), was reacted with diisopropylethylamine (0.46 g, 3.6 mmol), diphenylphosphinic chloride (0.34 g, 1.4 mmol), then reacted with 4-amino-3-methoxy-benzonitrile prepared in Example 57 (0.32 g, 2.1 mmol) to give rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide as a white solid (Yield, 0.15 g, 36%).

HRMS (ES⁺) m/z Calcd for C₃₁H₂₉Cl₂FN₄O₃+H [(M+H)⁺]: 595.1674, found: 595.1673.

Example 115

Preparation of rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

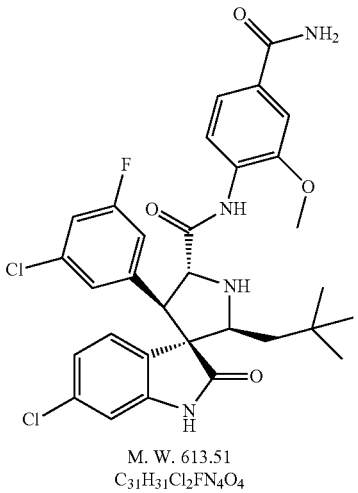

M. W. 613.51
C₃₁H₃₁Cl₂FN₄O₄

To the solution of rac-(2'S,3'R,4'R,5'R)-6-chloro-4'-(3-chloro-5-fluoro-phenyl)-2'-(2,2-dimethyl-propyl)-2-oxo-1,2-dihydro-Spiro[indole-3,3'-pyrrolidine]-5'-carboxylic acid (4-cyano-2-methoxy-phenyl)-amide (0.14 g, 0.2 mmol) prepared in Example 114 in DMSO (1 mL) at 0° C. was added an aqueous solution (30% Aldrich) of H₂O₂ (0.4 g, 3.5 mmol), then aqueous solution (1N) of NaOH (1.2 mL, 1.2 mmol) was added dropwise. The reaction mixture was stirred at 10° C. for 1 h. The mixture was partitioned between ethyl acetate and saturated aqueous Na₂SO₃ solution. The organic layer was separated, washed with water, brine, dried over MgSO₄, and concentrated to give rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (Yield 0.13 g, 87%)

HRMS (ES⁴) m/z Calcd for C₃₁H₃₁Cl₂FN₄O₄+H [(M+H)⁺]: 613.1779, found: 613.1778.

Example 116

Preparation of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-2-methoxy-phenyl)-amide

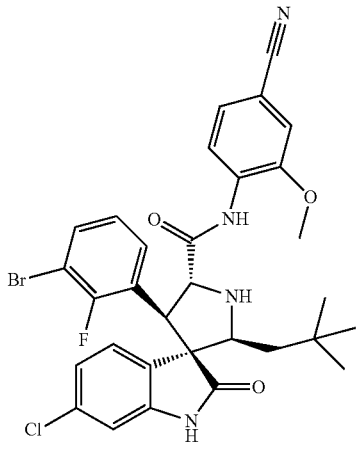

M. W. 639.95
$C_{31}H_{29}BrClFN_4O_3$

In a manner similar to the method described in Example 5, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid trifluoroacetic acid prepared in Example 97 (0.4 g, 0.66 mmol), was reacted with diisopropylethylamine (0.43 g, 3.3 mmol), diphenylphosphinic chloride (0.31 g, 1.3 mmol), then reacted with 4-amino-3-methoxy-benzonitrile prepared in Example 57 (0.29 g, 2.0 mmol) to give rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-2-methoxy-phenyl)-amide as a white foam (Yield 0.17 g, 40%).

HRMS (ES$^+$) m/z Calcd for $C_{31}H_{29}BrClFN_4O_3$+H [(M+H)$^+$]: 639.1169, found: 639.1169.

Example 117

Preparation of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

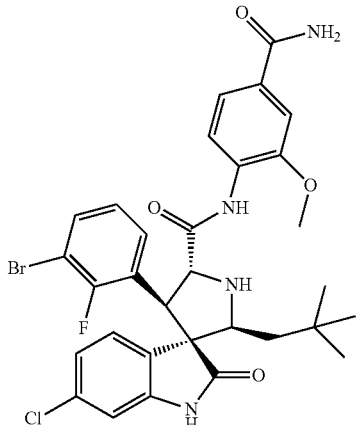

M. W. 657.97
$C_{31}H_{31}ClFN_4O_4$

To the solution of rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-2-methoxy-phenyl)-amide (0.16 g, 0.26 mmol) prepared in Example 116 in DMSO (1 mL) at 0° C. was added an aqueous solution (30% Aldrich) of $H_2O_2$ (0.43 g, 3.8 mmol), then aqueous solution (1N) of NaOH (1.3 mL, 1.3 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over $MgSO_4$, and concentrated. The residue was triturated with dichlormethane and hexanes to give rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (Yield 0.11 g, 67%)

HRMS (ES$^+$) m/z Calcd for $C_{31}H_{31}BrClFN_4O_4$+H [(M+H)$^+$]: 657.1274, found: 657.1272.

Example 118

Preparation of rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide

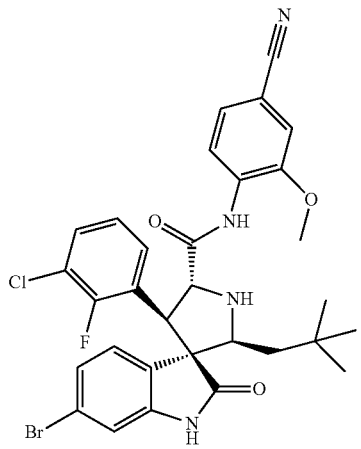

M. W. 639.95
$C_{31}H_{29}BrClFN_4O_3$

In a manner similar to the method described in Example 5, rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 92 (0.4 g, 0.66 mmol), was reacted with diisopropylethylamine (0.77 g, 5.9 mmol), diphenylphosphinic chloride (0.62 g, 2.6 mmol), then reacted with 4-amino-3-methoxy-benzonitrile prepared in Example 57 (0.29 g, 2.0 mmol) to give rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide as a off white solid (Yield 0.15 g, 36%).

HRMS (ES$^+$) m/z Calcd for $C_{31}H_{29}BrClFN_4O_3$+H [(M+H)$^+$]: 639.1169, found: 639.1172.

Example 119

Preparation of rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

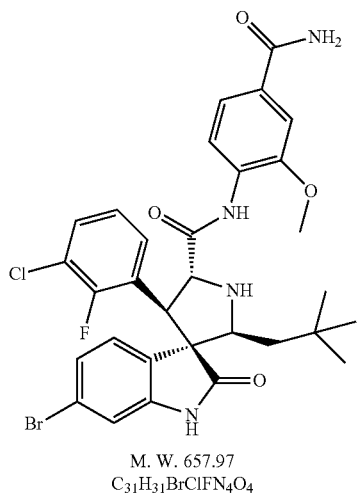

M. W. 657.97
$C_{31}H_{31}BrClFN_4O_4$

To the solution of rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide (0.14 g, 0.22 mmol) prepared in Example 118 in DMSO (1 mL) at 0° C. was added an aqueous solution (30% Aldrich) of $H_2O_2$ (0.37 g, 3.3 mmol), then aqueous solution (1N) of NaOH (1.1 mL, 1.1 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over $MgSO_4$, and concentrated. The residue was triturated with dichlormethane and hexanes to give rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (Yield 0.12 g, 83%)

HRMS (ES$^+$) m/z Calcd for $C_{31}H_{31}BrClFN_4O_4$+H [(M+H)$^+$]: 657.1274, found: 657.1276.

Example 120

Preparation of rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]amino}-3-methoxy-benzoic acid methyl ester

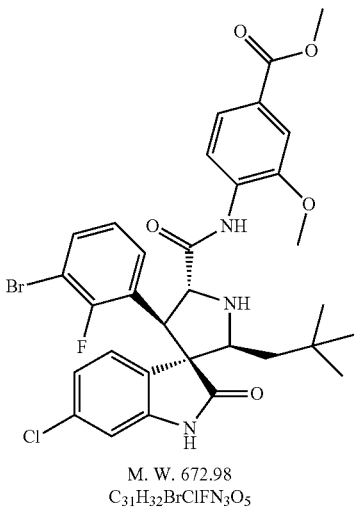

M. W. 672.98
$C_{31}H_{32}BrClFN_3O_5$

In a manner similar to the method described in Example 5, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid trifluoroacetic acid prepared in Example 97 (0.4 g, 0.64 mmol), was reacted with diisopropylethylamine (0.43 g, 3.3 mmol), diphenylphosphinic chloride (0.31 g, 1.3 mmol), then reacted with methyl 4-amino-3-methoxybenzoate (Ark Pharm) (0.18 g, 0.99 mmol) to give rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]amino}-3-methoxy-benzoic acid methyl ester as a white solid (Yield 0.22 g, 51%).

HRMS (ES$^+$) m/z Calcd for $C_{31}H_{32}BrClFN_3O_5$+H [(M+H).]: 672.1271, found: 672.1271.

Example 121

Preparation of rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]amino}-3-methoxy-benzoic acid

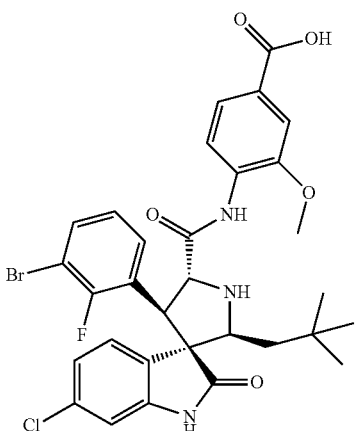

M. W. 658.95
$C_{31}H_{30}BrClFN_3O_5$

To a solution of rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]amino}-3-methoxy-benzoic acid methyl ester (0.2 g, 0.3 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water (5 mL), and acidified to "pH" 5-6 by dilute aqueous HCl solution. The mixture was then extracted with ethyl acetate three times. The combined organic extract was washed with water, brine, dried over MgSO$_4$, and concentrated. The residue was triturated with dichlormethane and hexanes to give rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]-amino}-3-methoxy-benzoic acid as a white powder (Yield, 0.16 g, 82%).

HRMS (ES$^+$) m/z Calcd for C$_{31}$H$_{30}$BrClFN$_3$O$_5$+H [(M+H)$^+$]: 658.1114, found: 658.1115.

Example 122

Preparation of rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester

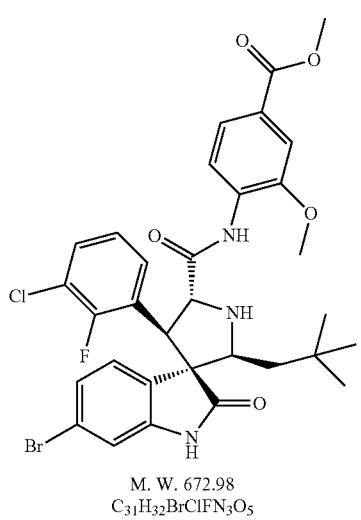

M. W. 672.98
C$_{31}$H$_{32}$BrClFN$_3$O$_5$

In a manner similar to the method described in Example 5, rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 92 (0.4 g, 0.66 mmol) was reacted with diisopropylethylamine (0.43 g, 3.3 mmol), diphenylphosphinic chloride (0.31 g, 1.3 mmol), then reacted with methyl 4-amino-3-methoxybenzoate (Ark Pharm) (0.18 g, 0.99 mmol) to give rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester as a white solid (Yield 0.21 g, 48%).

HRMS (ES$^+$) m/z Calcd for C$_{31}$H$_{32}$BrClFN$_3$O$_5$+H [(M+H)$^+$]: 672.1271, found: 672.1271.

Example 123

Preparation of rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid

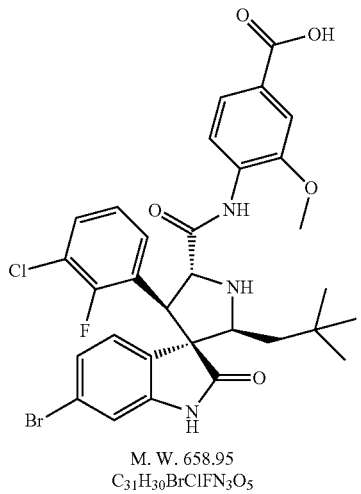

M. W. 658.95
C$_{31}$H$_{30}$BrClFN$_3$O$_5$

To a solution of rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester (0.19 g, 0.28 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water (5 mL), and acidified to "pH" 5-6 by dilute aqueous HCl solution. The mixture was then extracted with ethyl acetate three times. The combined organic extract was washed with water, brine, dried over MgSO$_4$, and concentrated. The residue was triturated with dichlormethane and hexanes to give rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid as a white powder (Yield, 0.15 g, 81%).

HRMS (ES$^+$) m/z Calcd for C$_{31}$H$_{30}$BrClFN$_3$O$_5$+H [(M+H)$^+$]: 658.1114, found: 658.1115.

Example 124

Preparation of rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester

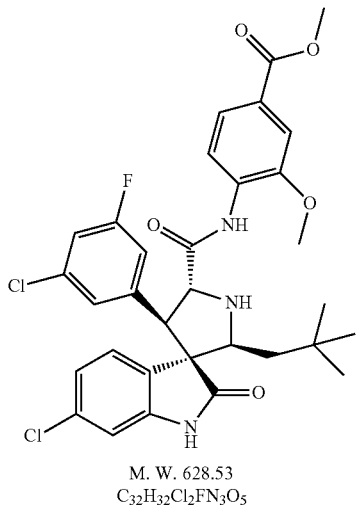

M. W. 628.53
$C_{32}H_{32}Cl_2FN_3O_5$

In a manner similar to the method described in Example 5, rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 87 (0.4 g, 0.69 mmol), was reacted with diisopropylethylamine (0.46 g, 3.6 mmol), diphenylphosphinic chloride (0.34 g, 1.4 mmol), then reacted with methyl 4-amino-3-methoxybenzoate (Ark Pharm) (0.19 g, 1.07 mmol) to give rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester as a white solid (Yield, 0.19 g, 44%).

HRMS (ES+) m/z Calcd for $C_{32}H_{32}Cl_2FN_3O_5$+H [(M+H)+]: 628.1776, found: 628.1781.

Example 125

Preparation of rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid

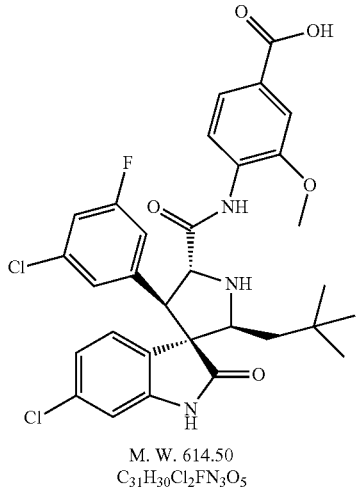

M. W. 614.50
$C_{31}H_{30}Cl_2FN_3O_5$

To a solution of rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester (0.17 g, 0.27 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water (5 mL), and acidified to "pH" 5-6 by dilute aqueous HCl solution. The mixture was then extracted with ethyl acetate three times. The combined organic extract was washed with water, brine, dried over MgSO4, and concentrated. The residue was triturated with dichlormethane and hexanes to give rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid as a white powder (Yield, 0.14 g, 84%).

HRMS (ES+) m/z Calcd for $C_{31}H_{30}Cl_2FN_3O_5$+H [(M+H)+]: 614.1620, found: 614.1618.

Example 126

Preparation of rac-4-{[(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester

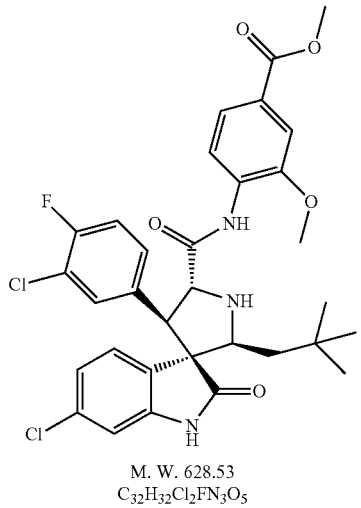

M. W. 628.53
$C_{32}H_{32}Cl_2FN_3O_5$

In a manner similar to the method described in Example 5, rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 82 (0.4 g, 0.69 mmol) was reacted with diisopropylethylamine (0.46 g, 3.6 mmol), diphenylphosphinic chloride (0.34 g, 1.4 mmol), then reacted with methyl 4-amino-3-methoxybenzoate (Ark Pharm) (0.19 g, 1.07 mmol) to give rac-4-{[(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester as a white solid (Yield, 0.22 g, 51%).

Example 127

Preparation of rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid

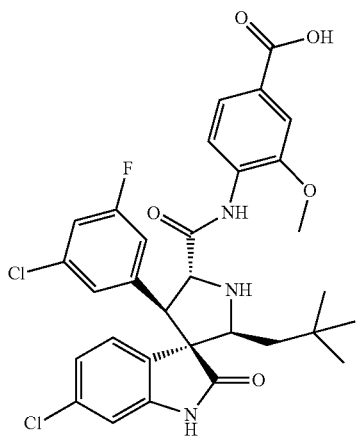

M. W. 614.50
$C_{31}H_{30}Cl_2FN_3O_5$

To a solution of rac-4-{[(2'S,3'R,4'R,5'S)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester (0.2 g, 0.32 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water (5 mL), and acidified to "pH" 5-6 by dilute aqueous HCl solution. The mixture was then extracted with ethyl acetate three times. The combined organic extract was washed with water, brine, dried over MgSO₄, and concentrated. The residue was triturated with dichlormethane and hexanes to give rac-4-{[(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid as a off white powder (Yield, 0.16 g, 82%).

HRMS (ES⁺) m/z Calcd for $C_{31}H_{30}Cl_2FN_3O_5+H$ [(M+H)⁺]: 614.1620, found: 614.1617.

Example 128

Preparation of intermediate
4-amino-3-ethoxy-benzoic acid methyl ester

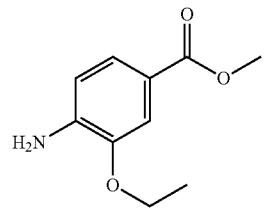

M. W. 195.22 $C_{10}H_{13}NO_3$

Step A To a solution of methyl 3-hydroxy-4-nitrobenzoate (Aldrich) (3 g, 15.2 mmol) in anhydrous DMF (25 mL) were added NaH (Aldrich, 60%) (0.91 g, 22.8 mmol) and iodoethane (2.61 g, 16.7 mmol) sequentially. The reaction mixture was stirred at room temperature for 2 h. Water was added. The mixture was extracted with ethyl acetate. The organic extract was washed with water, brine, dried over MgSO₄, and concentrated to give methyl 3-ethoxy-4-nitrobenzoate as a light yellow solid (1.0 g, 29%).

Step B A suspension of methyl 3-ethoxy-4-nitrobenzoate (1 g, 4.4 mmol) and Pd/C (Aldrich, 10%, 0.1 g) in ethyl acetate (25 mL) was vigorously shaken in a Parr under atmosphere of H₂ (50 psi) for 0.5 h. The mixture was filtered through a short pad of celite. The filtrate was concentrated to give 4-amino-3-ethoxy-benzoic acid methyl ester as a light yellow oil (0.8 g, 92%).

Example 129

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid methyl ester

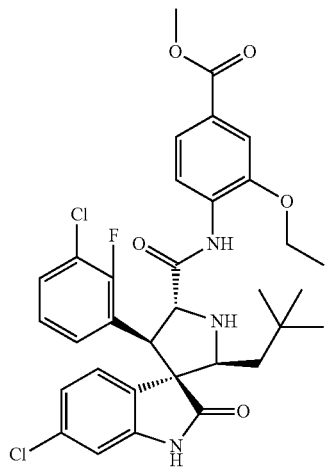

M. W. 642.55
$C_{33}H_{34}Cl_2FN_3O_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.4 g, 0.69 mmol), was reacted with diisopropylethylamine (0.46 g, 3.6 mmol), diphenylphosphinic chloride (0.34 g, 1.4 mmol), then reacted with 4-amino-3-ethoxy-benzoic acid methyl ester (0.21 g, 1.1 mmol) to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid methyl ester as a white solid (Yield, 0.13 g, 29%).

HRMS (ES$^+$) m/z Calcd for $C_{33}H_{34}Cl_2FN_3O_5$+H [(M+H)$^+$]: 642.1933, found: 642.1931.

Example 130

Preparation of rac-4-{[(2'S,3'R,4'S,512)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-ethoxy-benzoic acid

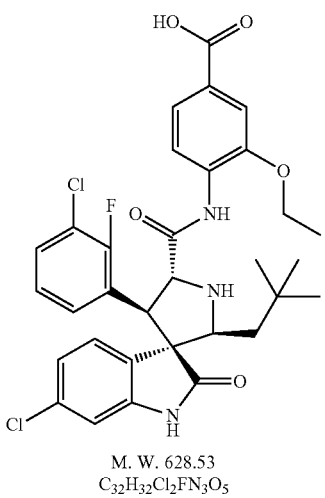

M. W. 628.53
$C_{32}H_{32}Cl_2FN_3O_5$

To a solution of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-ethoxy-benzoic acid methyl ester (0.12 g, 0.19 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water (5 mL), and acidified to "pH" 5-6 by dilute aqueous HCl solution. The mixture was then extracted with ethyl acetate three times. The combined organic extract was washed with water, brine, dried over MgSO$_4$, and concentrated. The residue was triturated with dichlormethane and hexanes to give rac-4-{[(2'S,3'R,4'S, 5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-ethoxy-benzoic acid as a off white powder (Yield, 0.1 g, 85%).

HRMS (ES$^+$) m/z Calcd for $C_{32}H_{32}Cl_2FN_3O_5$+H [(M+H)$^+$]: 628.1776, found: 628.1779.

Example 131

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-ethoxy-phenyl)-amide

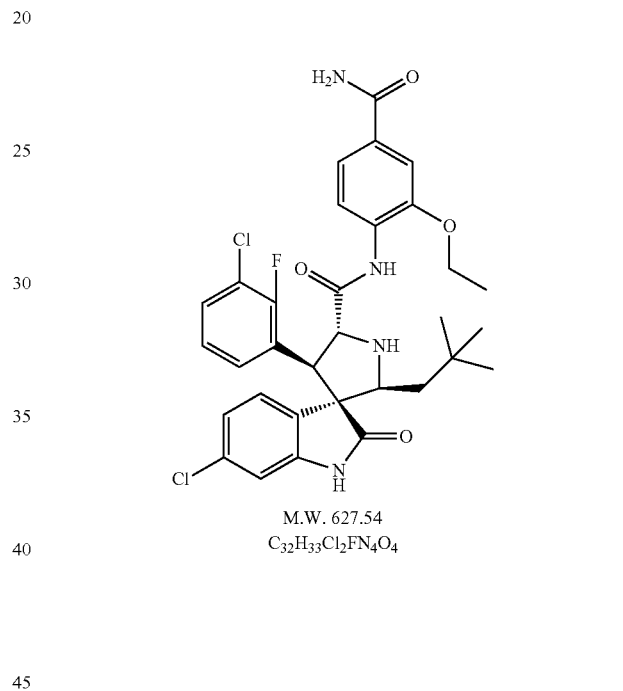

M.W. 627.54
$C_{32}H_{33}Cl_2FN_4O_4$

To a solution of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid (0.1 g, 0.17 mmol) prepared in Example 130 in anhydrous DMF (2 mL) were added EDCI (64 mg, 0.33 mmol), HOBt (45 mg, 0.33 mmol), NH$_4$Cl (89 mg, 1.67 mmol), and triethylamine (34 mg, 0.33 mmol) sequentially. The reaction mixture was heated at 80° C. for 1 h. The mixture was cooled to room temperature, then partitioned between ethyl acetate and water. The organic layer was separated, and aqueous layer was extracted with ethyl acetate twice. The combined organic extract was washed with water, brine, dried over MgSO$_4$, and concentrated. The residue was purified by chromatography (25-100% EtOAc in hexanes) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-ethoxy-phenyl)-amide as a off white solid (37 mg, 35%).

HRMS (ES+) m/z Calcd for $C_{32}H_{33}Cl_2FN_4O_4$+H [(M+H)+]: 627.1936, found: 627.1936.

Example 132

Preparation of intermediate 4-[2-(tert-butyl-dimethyl-silanyloxy)-ethoxy]-2-methoxy-phenylamine

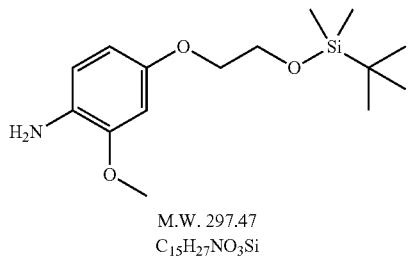

M.W. 297.47
$C_{15}H_{27}NO_3Si$

Step A To a solution of 4-fluoro-2-methoxy-1-nitrobenzene (Combi-blocks, 3.4 g, 19.9 mmol) in DMSO (40 mL) was added an aqueous solution (1N) of NaOH (40 mL, 40 mmol). The reaction mixture was heated at 80° C. for 20 h. The mixture was cooled to room temperature, and the "pH" of the solution was adjusted to 5 by aqueous HCl solution. The mixture was extracted with ethyl acetate three times. The combined organic extract was washed with water, brine, dried over MgSO$_4$, and concentrated to give 3-methoxy-4-nitrophenol as a light yellow solid (3.2 g, 95%).

Step B To a solution of 3-methoxy-4-nitrophenol (1 g, 5.9 mmol) in anhydrous DMF (25 mL) were added K$_2$CO$_3$ (2.45 g, 17.7 mmol) and (2-bromoethoxy)(tert-butyl)dimethylsilane (1.7 g, 7.1 mmol) sequentially. The reaction mixture was heated at 70° C. for 20 h. The mixture was cooled to room temperature, and diluted with water. The mixture was extracted with ethyl acetate three times. The combined organic extract was washed with water, brine, dried over MgSO$_4$, and concentrated. The residue was purified by chromatography (0-20% EtOAc in hexanes) to give tert-butyl-[2-(3-methoxy-4-nitro-phenoxy)-ethoxy]-dimethyl-silane as a light yellow oil (1.0 g, 52%).

Step C A suspension of tert-butyl-[2-(3-methoxy-4-nitro-phenoxy)-ethoxy]-dimethyl-silane (1 g, 3.05 mmol) and Pd/C (Aldrich, 10%, 0.1 g) in ethyl acetate (25 mL) was vigorously shaken in a Parr under atmosphere of H$_2$ (50 psi) for 0.5 h. The mixture was filtered through a short pad of celite. The filtrate was concentrated to give 4-[2-(tert-butyl-dimethyl-silanyloxy)-ethoxy]-2-methoxy-phenylamine as a light yellow oil (0.9 g, 99%).

Example 133

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide

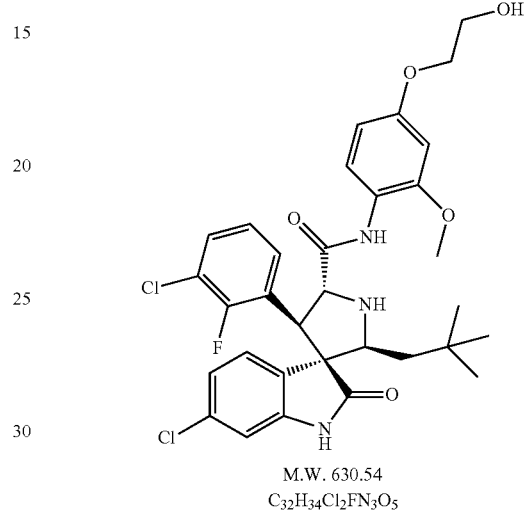

M.W. 630.54
$C_{32}H_{34}Cl_2FN_3O_5$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid (0.4 g, 0.69 mmol) prepared in Example 4 in dichloromethane (9 mL) was added diisopropylethylamine (0.46 g, 3.6 mmol), diphenylphosphinic chloride (Aldrich) (0.34 g, 1.42 mmol) respectively. The mixture was stirred at room temperature for 8 min, then 442-(tert-butyl-dimethyl-silanyloxy)-ethoxy]-2-methoxy-phenylamine (0.32 g, 1.1 mmol) was added. The reaction mixture was stirred at room temperature for 72 h. The mixture was concentrated. The residue was dissolved into tetrahydrofuran (9 mL), and an aqueous solution (1N) of HCl (1 mL) was added. The reaction mixture was stirred at room temperature for 2 h, then concentrated. The residue was partitioned between ethyl acetate and aqueous saturated NaHCO$_3$ solution. The organic layer was separated, and aqueous layer was extracted with ethyl acetate twice. The combined organic extract was washed with water, brine, dried over Na$_2$SO$_4$, then concentrated. The residue was purified by chromatography (0-50% of EtOAc in CH$_2$Cl$_2$) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide as a off white solid (0.18 g, 41%).

HRMS (ES+) m/z Calcd for $C_{32}H_{34}Cl_2FN_3O_5$+H [(M+H)+]: 630.1933, found: 630.1937.

Example 134

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide

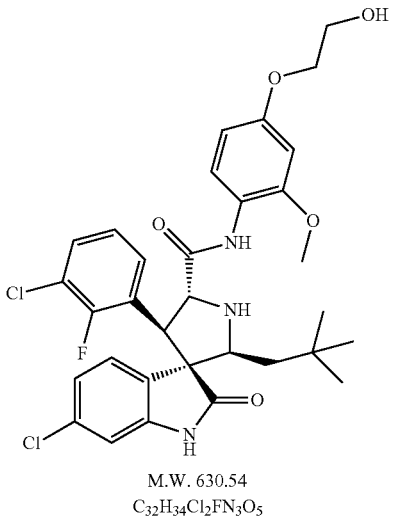

M.W. 630.54
$C_{32}H_{34}Cl_2FN_3O_5$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide (0.15 g) was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide as a off white solid (58 mg, 39%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide as a off white solid (64 mg, 43%).

HRMS (ES$^+$) m/z Calcd for $C_{32}H_{34}Cl_2FN_3O_5$+H [(M+H)$^+$]: 630.1933, found: 630.1934.

Example 135

Preparation of intermediate chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester

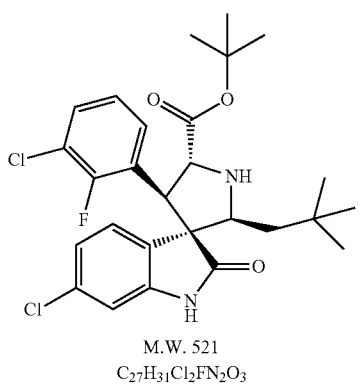

M.W. 521
$C_{27}H_{31}Cl_2FN_2O_3$

Rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester (6.43 g) prepared in Example 3 was separated by chiral SFC chromatography to provide chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester as a white solid (2.7 g, 43%) and chiral (2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester as a white solid (2.7 g, 43%).

Example 136

Preparation of intermediate chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid

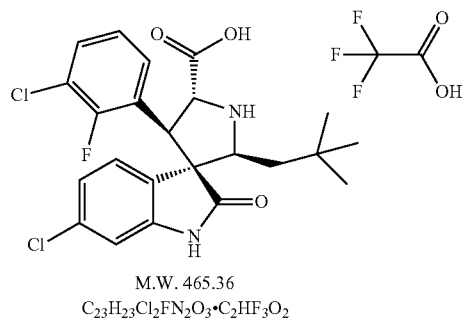

M.W. 465.36
$C_{23}H_{23}Cl_2FN_2O_3 \cdot C_2HF_3O_2$

A solution of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid tert-butyl ester (2.7 g, 5.2 mmol) in dichloromethane (15 mL) was added trifluoroacetic acid (15 mL). The reaction mixture was stirred at room temperature for 18 h, then concentrated. The residue was then triturated with ethyl ether hexanes, concentrated, dried in vacuo to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid as a off white solid (3 g, 100%).

Example 137

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide

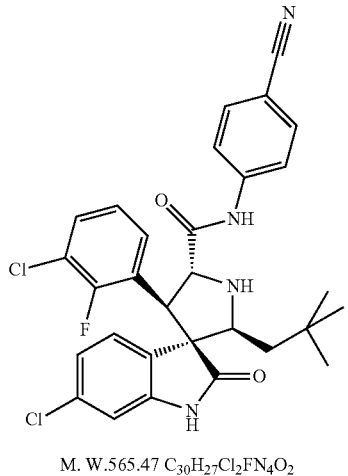

M. W. 565.47 C$_{30}$H$_{27}$Cl$_2$FN$_4$O$_2$

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.3 g, 0.52 mmol), was reacted with diisopropylethylamine (0.34 g, 2.7 mmol), diphenylphosphinic chloride (0.35 g, 1.1 mmol), then reacted with 4-aminobenzonitrile (Aldrich) (0.13 g, 1.1 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide as a off white foam (Yield 0.12 g, 41%).

MS (ES$^+$) m/z Calcd for C$_{30}$H$_{27}$Cl$_2$FN$_4$O$_2$+H [(M+H)$^{3o}$]: 565, found: 565.

Example 138

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide

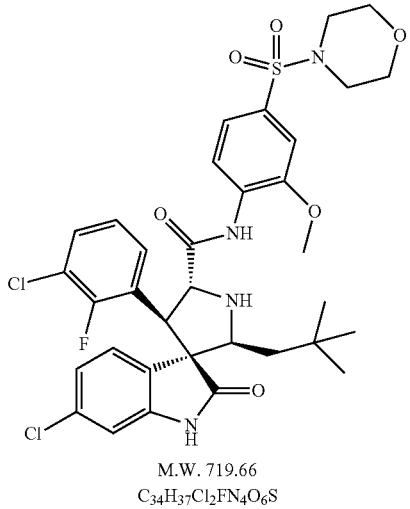

M.W. 719.66
C$_{34}$H$_{37}$Cl$_2$FN$_4$O$_6$S

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.4 g, 0.69 mmol), was reacted with diisopropylethylamine (0.46 g, 3.6 mmol), diphenylphosphinic chloride (0.34 g, 1.4 mmol), then reacted with 2-methoxy-4-(morpholinosulfonyl)aniline (Matrix) (0.29 g, 1.1 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide as a white solid (Yield 0.04 g, 8%).

HRMS (ES$^+$) m/z Calcd for C$_{34}$H$_{37}$Cl$_2$FN$_4$O$_6$S+H [(M+H)$^{3o}$]: 719.1868, found: 719.1871.

Example 139

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-nitro-phenyl)-amide

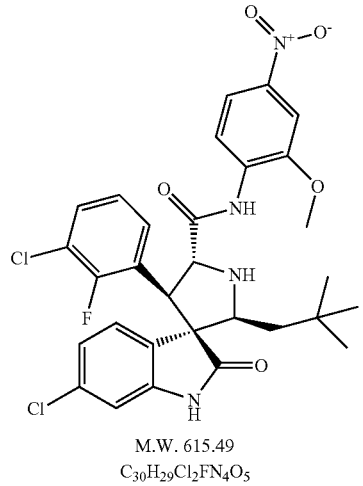

M.W. 615.49
C$_{30}$H$_{29}$Cl$_2$FN$_4$O$_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.4 g, 0.69 mmol), was reacted with diisopropylethylamine (0.46 g, 3.6 mmol), diphenylphosphinic chloride (0.34 g, 1.4 mmol), then reacted with 2-methoxy-4-nitroaniline (Aldrich) (0.18 g, 1.1 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-nitro-phenyl)-amide as a white solid (Yield 0.06 g, 14%).

HRMS (ES$^+$) m/z Calcd for C$_{30}$H$_{29}$Cl$_2$FN$_4$O$_5$+H [(M+H)$^{3o}$]: 615.1572, found: 615.1571.

Example 140

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-amino-2-methoxy-phenyl)-amide

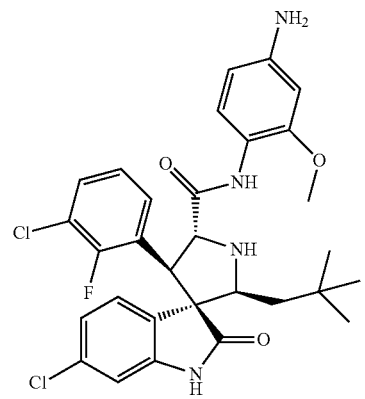

M.W. 585.50
$C_{30}H_{31}Cl_2FN_4O_3$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-nitro-phenyl)-amide (35 mg, 0.057 mmol) in methanol (3 mL) was added an aqueous solution (1.5 mL) of NH$_4$Cl (30 mg, 0.57 mmol), followed by activated Zinc (Aldrich, 37 mg, 0.57 mmol). The reaction mixture was stirred at room temperature for 0.5 h. The mixture was filtered through a short pad of celite. The mixture was concentrated. The residue was partitioned between ethyl acetate and water. The organic layer was separated, and aqueous layer was extracted with ethyl acetate. The combined organic extract was washed with water, brine, dried over MgSO$_4$, and concentrated. The residue was purified by chromatography (0-50% EtOAc in dichloromethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-amino-2-methoxy-phenyl)-amide as a off white solid (24 mg, 72%).

HRMS (ES$^+$) m/z Calcd for $C_{30}H_{31}Cl_2FN_4O_3$+H [(M+H)$^+$]: 585.1830, found: 585.1831.

Example 141

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetylamino-2-methoxy-phenyl)-amide

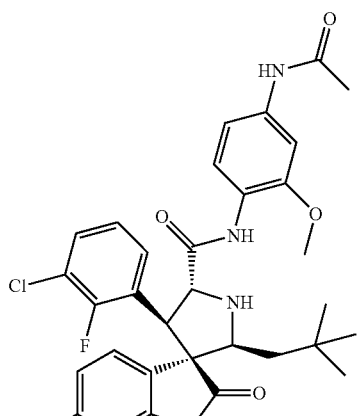

M.W. 627.54
$C_{32}H_{33}Cl_2FN_4O_4$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-amino-2-methoxy-phenyl)-amide (17 mg, 0.029 mmol) and triethylamine (4 mg, 0.044 mmol) in THF (2 mL) was acetyl chloride (2.3 mg, 0.029 mmol). The reaction mixture was stirred at room temperature for 1 h. The mixture was concentrated. The residue was partitioned between ethyl acetate and water. The organic layer, was separated, and aqueous layer was extracted with ethyl acetate. The combined organic extract was washed with water, brine, dried over MgSO$_4$, and concentrated to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetylamino-2-methoxy-phenyl)-amide as a off white solid (17 mg, 93%).

HRMS (ES$^+$) m/z Calcd for $C_{32}H_{33}Cl_2FN_4O_4$+H [(M+H)$^+$]: 627.1936, found: 627.1939.

Example 142

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-2-methoxy-phenyl-amide

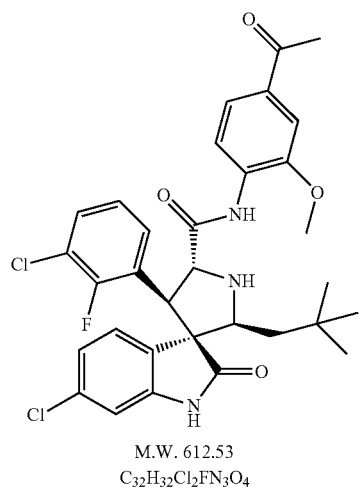

M.W. 612.53
$C_{32}H_{32}Cl_2FN_3O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.43 mmol), was reacted with diisopropylethylamine (0.29 g, 2.2 mmol), diphenylphosphinic chloride (0.21 g, 0.89 mmol), then reacted with 1-(4-amino-3-methoxyphenyl)ethanone (Bionet) (0.11 g, 0.67 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-2-methoxy-phenyl)-amide as a light yellow solid (Yield 0.098 g, 37%).

HRMS (ES⁺) m/z Calcd for $C_{32}H_{32}Cl_2FN_3O_4$+H [(M+H)⁺]: 612.1827 found: 612.1825.

Example 143

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-morpholin-4-yl-phenyl)-amide

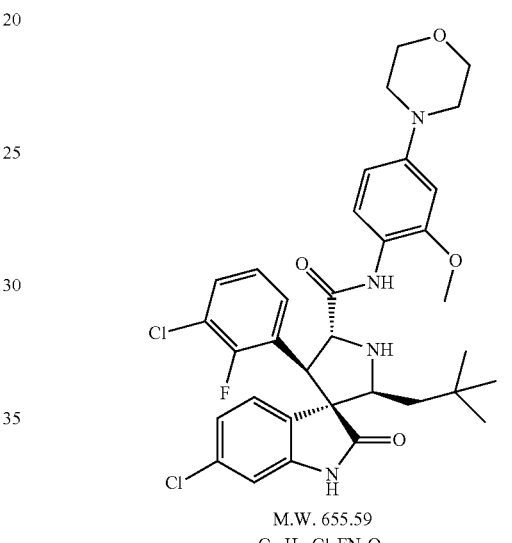

M.W. 655.59
$C_{34}H_{37}Cl_2FN_4O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.43 mmol), was reacted with diisopropylethylamine (0.29 g, 2.2 mmol), diphenylphosphinic chloride (0.21 g, 0.89 mmol), then reacted with 2-methoxy-4-morpholinoaniline (Bionet) (0.14 g, 0.67 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-morpholin-4-yl-phenyl)-amide as a light yellow solid (Yield 0.13 g, 46%).

HRMS (ES⁺) m/z Calcd for $C_{34}H_{37}Cl_2FN_4O_4$+H [(M+H)⁺]: 655.2249, found: 655.2252.

Example 144

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2,6-dimethyl-morpholin-4-yl)-2-methoxy-phenyl]-amide

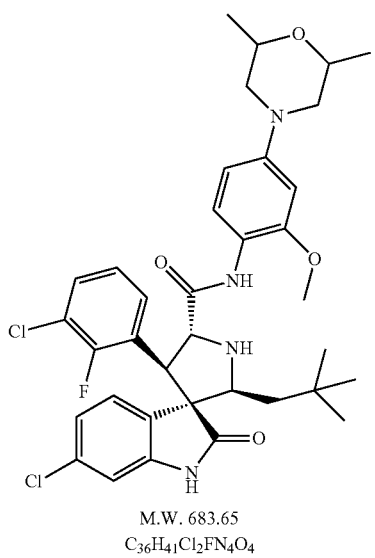

M.W. 683.65
C$_{36}$H$_{41}$Cl$_2$FN$_4$O$_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.43 mmol), was reacted with diisopropylethylamine (0.29 g, 2.2 mmol), diphenylphosphinic chloride (0.21 g, 0.89 mmol), then reacted with 4-(2,6-dimethylmorpholino)-2-methoxyaniline (Bionet) (0.11 g, 0.44 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2,6-dimethyl-morpholin-4-yl)-2-methoxy-phenyl]-amide as a white solid (Yield 0.11 g, 37%).

HRMS (ES$^+$) m/z Calcd for C$_{36}$H$_{41}$Cl$_2$FN$_4$O$_4$+H [(M+H)$^+$]: 683.2562, found: 683.2565.

Example 145

Preparation of intermediate rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-trifluoromethoxy-phenyl)-amide

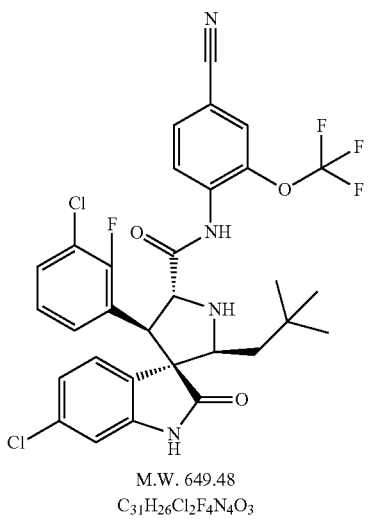

M.W. 649.48
C$_{31}$H$_{26}$Cl$_2$F$_4$N$_4$O$_3$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.4 g, 0.69 mmol), was reacted with diisopropylethylamine (0.46 g, 3.6 mmol), diphenylphosphinic chloride (0.34 g, 1.4 mmol), then reacted with 4-amino-3-(trifluoromethoxy)benzonitrile (Matrix) (0.14 g, 0.71 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-trifluoromethoxy-phenyl)-amide as a yellow solid (Yield, 40 mg, 9%).

Example 146

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-trifluoromethoxy-phenyl)-amide

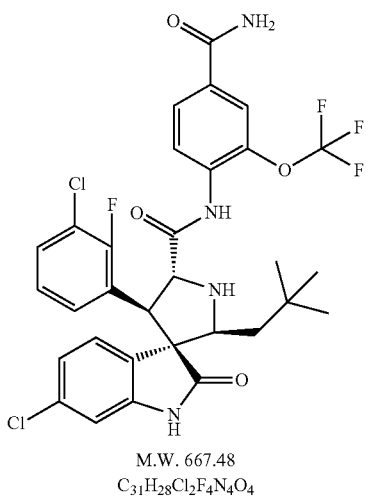

M.W. 667.48
C$_{31}$H$_{28}$Cl$_2$F$_4$N$_4$O$_4$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-trifluoromethoxy-phenyl)-amide (40 mg, 0.06 mmol) prepared in Example 145 in DMSO (1 mL) at 0° C. was added an aqueous solution (30% Aldrich) of $H_2O_2$ (0.1 g, 0.9 mmol), then aqueous solution (1N) of NaOH (0.3 mL, 0.3 mmol) was added dropwise. The reaction mixture was stirred at 10° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (0-100% EtOAc in dichlormethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-trifluoromethoxy-phenyl)-amide as a white solid (Yield 9 mg, 22%)

HRMS (ES$^+$) m/z Calcd for $C_{31}H_{28}Cl_2F_4N_4O_4$+H [(M+H)$^+$]: 667.1497, found: 667.1499.

Example 147

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid phenylamide

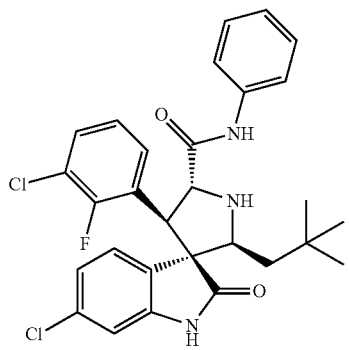

M. W. 540.46 $C_{29}H_{28}Cl_2FN_3O_2$

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.15 g, 0.26 mmol), was reacted with diisopropylethylamine (0.17 g, 1.3 mmol), diphenylphosphinic chloride (0.17 g, 0.53 mmol), then reacted with aniline (Aldrich) (0.05 g, 0.53 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid phenylamide as a white foam (Yield 0.033 g, 24%).

HRMS (ES$^+$) m/z Calcd for $C_{29}H_{28}Cl_2FN_3O_2$+H [(M+H)$^+$]: 540.1616, found: 540.1615.

Example 148

Preparation of chiral (2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide

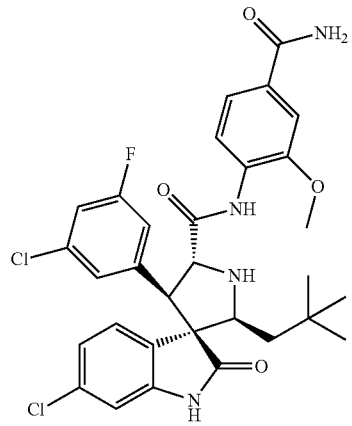

M. W. 613.51 $C_{31}H_{31}Cl_2FN_4O_4$

Rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide (0.11 g) prepared in Example 115 was separated by chiral SFC chromatography to provide chiral (2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (46 mg, 42%) and chiral (2'R,3'S,4'S,5'S)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide as a white solid (41 mg, 37%).

HRMS (ES$^+$) m/z Calcd for $C_{31}H_{31}Cl_2FN_4O_4$+H [(M+H)$^+$]: 613.1779, found: 613.1779.

Example 149

Preparation of intermediate 4-amino-3-butoxy-benzoic acid methyl ester

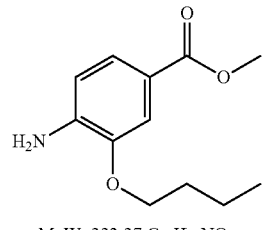

M. W. 223.27 $C_{12}H_{17}NO_3$

Step A. To a solution of 3-butoxy-4-nitrobenzoic acid (City Chemicals) (2.5 g, 10.5 mmol) in methanol (10 mL) were added concentrated $H_2SO_4$ (1 g, 10.5 mmol). The reaction mixture was heated at refluxing for 2 h. The mixture was concentrated. The residue was partitioned between ethyl acetate and water. The organic layer was separated, and aqueous layer was extracted with ethyl acetate twice. The combined organic extract was washed with water, aqueous saturated NaHCO₃ solution, brine, dried over MgSO₄, and concentrated to give methyl 3-butoxy-4-nitrobenzoate as a brown oil (2.5 g, 95%).

Step B. A solution of methyl 3-butoxy-4-nitrobenzoate (2.5 g, 9.9 mmol) in methanol (100 mL) was added an aqueous solution (50 mL) of NH₄Cl (5.3 g, 99 mmol), followed by activated zinc (Aldrich, 6.5 g, 99 mmol). The reaction mixture was stirred at room temperature for 1 h. The mixture was filtered through a short pad of celite. The mixture was concentrated. The residue was partitioned between ethyl acetate and water. The organic layer was separated, and aqueous layer was extracted with ethyl acetate. The combined organic extract was washed with water, brine, dried over MgSO₄, and concentrated to give 4-amino-3-butoxy-benzoic acid methyl ester as a yellow solid (1.8 g, 82%).

Example 150

Preparation of rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester

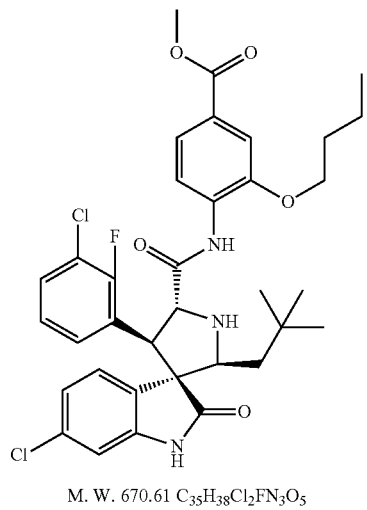

M. W. 670.61 C₃₅H₃₈Cl₂FN₃O₅

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.4 g, 0.69 mmol), was reacted with diisopropylethylamine (0.46 g, 3.6 mmol), diphenylphosphinic chloride (0.34 g, 1.4 mmol), then reacted with 4-amino-3-butoxy-benzoic acid methyl ester (0.24 g, 1.1 mmol) prepared in Example 149 to give rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid methyl ester as a light brown solid (Yield, 0.14 g, 30%).

HRMS (ES⁺) m/z Calcd for C₃₅H₃₈Cl₂FN₃O₅+H [(M+H)⁺]: 670.2246, found: 670.2246.

Example 151

Preparation of rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid

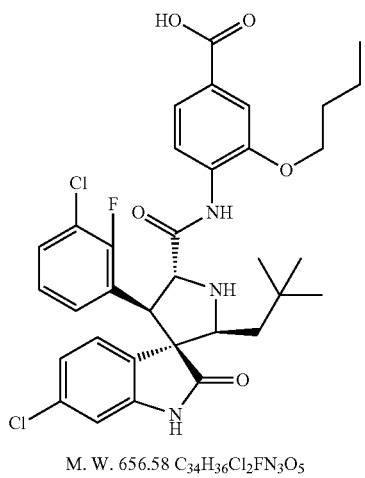

M. W. 656.58 C₃₄H₃₆Cl₂FN₃O₅

To a solution of rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester (0.13 g, 0.19 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water (5 mL), and acidified to "pH" 5-6 by dilute aqueous HCl solution. The mixture was then extracted with ethyl acetate three times. The combined organic extract was washed with water, brine, dried over MgSO₄, and concentrated. The residue was triturated with dichlormethane and hexanes to give rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid as a light brown solid (Yield, 0.12 g, 94%).

HRMS (ES+) m/z Calcd for $C_{34}H_{36}Cl_2FN_3O_5$+H [(M+H)+]: 656.2089, found: 656.2089.

Example 152

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-butoxy-4-carbamoyl-phenyl)-amide

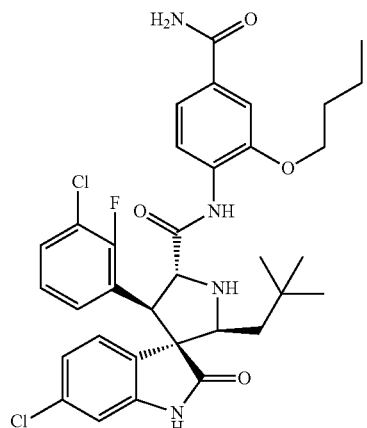

M. W. 655.59 $C_{34}H_{37}Cl_2FN_4O_4$

To a solution of rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid (0.1 g, 0.15 mmol) prepared in Example 151 in anhydrous DMF (2 mL) were added EDCI (59 mg, 0.31 mmol), HOBt (41 mg, 0.31 mmol), NH4Cl (81 mg, 1.5 mmol), and triethylamine (31 mg, 0.31 mmol) sequentially. The reaction mixture was heated at 80° C. for 1 h. The mixture was cooled to room temperature, then partitioned between ethyl acetate and water. The organic layer was separated, and aqueous layer was extracted with ethyl acetate twice. The combined organic extract was washed with water, brine, dried over MgSO4, and concentrated. The residue was purified by chromatography (25-100% EtOAc in hexanes) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-butoxy-4-carbamoyl-phenyl)-amide as a white solid (88 mg, 89%).

HRMS (ES+) m/z Calcd for $C_{34}H_{37}Cl_2FN_4O_4$+H [(M+H)30]: 655.2249, found: 655.2249.

Example 153

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-tetrazol-1-yl-phenyl)-amide

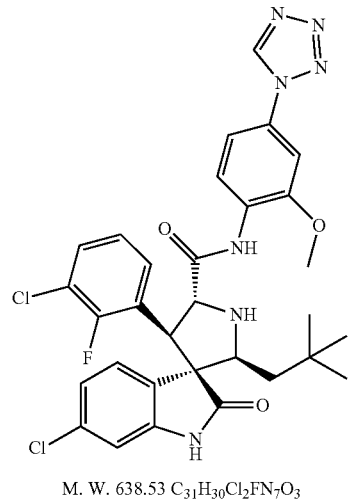

M. W. 638.53 $C_{31}H_{30}Cl_2FN_7O_3$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.25 g, 0.43 mmol), was reacted with diisopropylethylamine (0.29 g, 2.2 mmol), diphenylphosphinic chloride (0.21 g, 0.89 mmol), then reacted with 2-methoxy-4-(1H-tetrazol-1-yl)aniline (Bionet) (0.13 g, 0.66 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-tetrazol-1-yl-phenyl)-amide as a white solid (Yield 82 mg, 30%).

HRMS (ES+) m/z Calcd for $C_{31}H_{30}Cl_2FN_7O_3$+H [(M+H)+]: 638.1844, found: 638.1844.

Example 154

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide

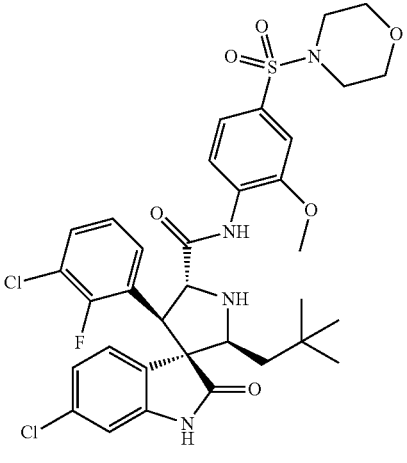

M. W. 719.66 $C_{34}H_{37}Cl_2FN_4O_6S$

Example 155

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonylamino-2-methoxy-phenyl)-amide

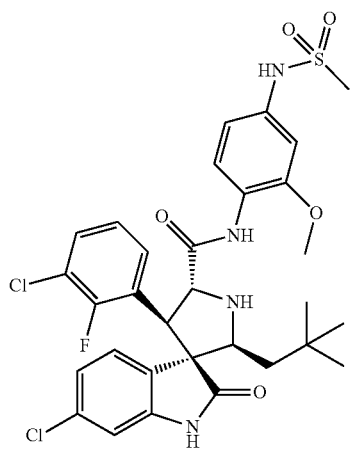

M. W. 663.60 C$_{31}$H$_{33}$Cl$_2$FN$_4$O$_5$S

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol), was reacted with diisopropylethylamine (0.34 g, 2.6 mmol), diphenylphosphinic chloride (0.38 g, 1.6 mmol), then reacted with N-(4-amino-3-methoxyphenyl)methanesulfonamide hydrochloride (Astatech) (0.2 g, 0.8 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonylamino-2-methoxy-phenyl)-amide as a yellow solid (Yield 0.16 g, 47%).

HRMS (ES$^+$) m/z Calcd for C$_{31}$H$_{33}$Cl$_2$FN$_4$O$_5$S+H [(M+H)$^+$]: 663.1606, found: 663.1606.

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.3 g, 0.52 mmol), was reacted with diisopropylethylamine (0.34 g, 2.6 mmol), diphenylphosphinic chloride (0.37 g, 1.6 mmol), then reacted with 2-methoxy-4-(morpholinosulfonyl)aniline (Matrix) (0.16 g, 0.59 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide as a white solid (Yield 0.06 g, 17%).

HRMS (ES$^+$) m/z Calcd for C$_{34}$H$_{37}$Cl$_2$FN$_4$O$_6$S+H [(M+H)$^{3o}$]: 719.1868, found: 719.1865.

Example 156

Preparation of intermediate 2-methoxy-4-(tetrahydro-pyran-4-yloxy)-phenylamine

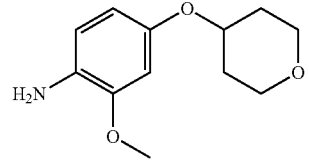

M. W. 223.27 C$_{12}$H$_{17}$NO$_3$

Step A To a solution of 4-hydroxytetrahydropyran (4.5 g, 44 mmol) (Aldrich) in dichloromethane (90 mL) at 0° C. was added triethylamine (5.4 g, 53 mmol), and methanesulfonyl chloride (3.73 mL, 48 mmol, Aldrich). The reaction mixture was stirred at 0° C. for 1 h, then at room temperature for 1.5 h. The mixture was poured into water, extracted with dichloromethane. The organic layer was separated, washed with water, brine, dried over MgSO$_4$, and concentrated to give crude methanesulfonic acid tetrahydropyran-4-yl ester as a white solid (Yield 8 g, 100%).

Step B To a solution of 3-methoxy-4-nitrophenol (0.5 g, 3 mmol) prepared in Example 132 Step A in anhydrous DMF (13 mL) were added Cs$_2$CO$_3$ (2.9 g, 8.9 mmol) and methanesulfonic acid tetrahydropyran-4-yl ester (0.64 g, 3.6 mmol) sequentially. The reaction mixture was heated at 120° C. for 3 h. The mixture was cooled to room temperature, and diluted with water. The mixture was extracted with ethyl acetate three times. The combined organic extract was washed with water, brine, dried over MgSO$_4$, and concentrated. The residue was purified by chromatography (40-60% EtOAc in hexanes) to give 4-(3-methoxy-4-nitrophenoxy)tetrahydro-2H-pyran as a yellow oil (0.4 g, 53%).

Step C A suspension of 4-(3-methoxy-4-nitrophenoxy)tetrahydro-2H-pyran (0.4 g, 1.6 mmol) and Pd/C (Aldrich, 10%, 0.1 g) in ethyl acetate (10 mL) was vigorously shaken in a Parr under atmosphere of H$_2$ (50 psi) for 0.5 h. The mixture was filtered through a short pad of celite. The filtrate was concentrated to give 2-methoxy-4-(tetrahydro-pyran-4-yloxy)-phenylamine as a light yellow oil (0.3 g, 85%).

Example 157

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(tetrahydro-pyran-4-yloxy)-phenyl]-amide

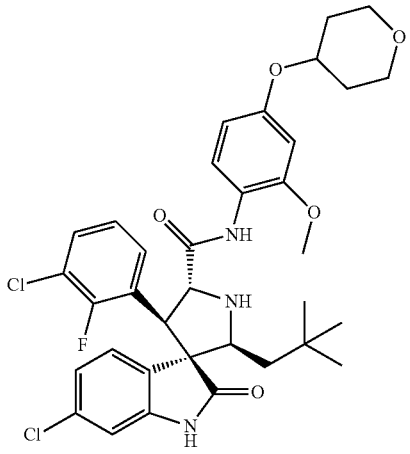

M. W. 670.61 C$_{35}$H$_{38}$Cl$_2$FN$_3$O$_5$

137

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.2 g, 0.35 mmol), was reacted with diisopropylethylamine (0.22 g, 1.7 mmol), diphenylphosphinic chloride (0.16 g, 0.69 mmol), then reacted with 2-methoxy-4-(tetrahydro-pyran-4-yloxy)-phenylamine prepared in Example 156 (0.1 g, 0.52 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(tetrahydro-pyran-4-yloxy)-phenyl]amide as a off white solid (Yield 0.08 g, 35%).

HRMS (ES$^+$) m/z Calcd for $C_{35}H_{38}Cl_2FN_3O_5$+H [(M+H)$^+$]: 670.2246, found: 670.2242.

Example 158

Preparation of intermediate (4-amino-3-methoxy-phenyl)-acetic acid tert-butyl ester

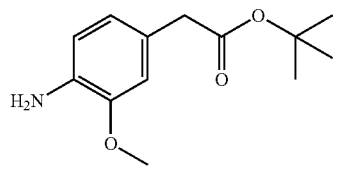

M. W. 227.30 $C_{13}H_{19}NO_3$

Step A To a solution of 3-methoxy-4-nitrobenzoic acid (Alfa) (10 g, 51 mmol) in toluene (75 mL) was added $SOCl_2$ (11.5 g, 97 mmol), and a catalytic amount of DMF. The mixture was heated at refluxing for 3 h, then cooled to room temperature. The mixture was concentrated. The residue was dissolved into tetrahydrofuran (125 mL) and triethylamine (8.4 g, 83 mmol), and the temperature of the mixture was lowered to 0° C. A hexane solution (Alfa, 2 M) of (trimethylsilyl)diazomethane (41 mL, 83 mmol) was added. The reaction mixture was stirred at room temperature for 18 h. The mixture was poured into an aqueous saturated $NaHCO_3$ solution, extracted with ethyl acetate three times. The combined organic extract was washed with brine, dried over $MgSO_4$, and concentrated to give crude 2-diazo-1-(3-methoxy-4-nitro-phenyl)-ethanone as a brown oil (Yield 5 g, 45%).

Step B To a refluxing solution of triethylamine (10.5 mL, 22.5 mmol) and silver benzoate (3.78 g, 22.5 mmol) in tert-butanol (100 mL) and toluene (100 mL) at 120° C. was added a tert-butanol solution (80 mL) of 2-diazo-1-(3-methoxy-4-nitro-phenyl)-ethanone (5 g, 22.5 mmol). The reaction mixture was heated at 120° C. for 1 h. The mixture was cooled to room temperature, and filtered through a short pad of celite. The filtrated was diluted with ethyl acetate, and washed with brine, dried over $MgSO_4$, and concentrated. The residue was purified by chromatography (0-25% EtOAc in hexanes) to give (3-methoxy-4-nitro-phenyl)-acetic acid tert-butyl ester as a brown oil (3.2 g, 53%).

138

Step C A suspension of (3-methoxy-4-nitro-phenyl)-acetic acid tert-butyl ester (3 g, 11.2 mmol) in methanol (100 mL) was added an aqueous solution (50 mL) of $NH_4Cl$ (6 g, 112 mmol), followed by activated zinc (Aldrich, 7.3 g, 112 mmol). The reaction mixture was stirred at room temperature for 0.5 h. The mixture was filtered through a short pad of celite. The mixture was concentrated. The residue was partitioned between ethyl acetate and water. The organic layer was separated, and aqueous layer was extracted with ethyl acetate. The combined organic extract was washed with water, brine, dried over $MgSO_4$, and concentrated to give (4-amino-3-methoxy-phenyl)-acetic acid tert-butyl ester as a brown oil (2.5 g, 94%).

Example 159

Preparation of chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-phenyl)-acetic acid tert-butyl ester

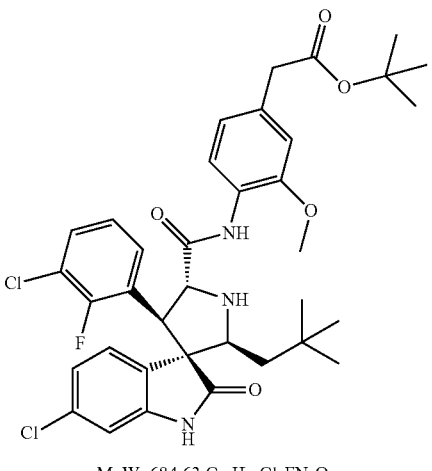

M. W. 684.63 $C_{36}H_{40}Cl_2FN_3O_5$

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.4 g, 0.69 mmol), was reacted with diisopropylethylamine (0.45 g, 3.5 mmol), diphenylphosphinic chloride (0.49 g, 2.1 mmol), then reacted with (4-amino-3-methoxy-phenyl)-acetic acid tert-butyl ester prepared in Example 158 (0.25 g, 1 mmol) to give chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-phenyl)-acetic acid tert-butyl ester as a off white solid (Yield 0.18 g, 38%).

HRMS (ES$^+$) m/z Calcd for $C_{36}H_{40}Cl_2FN_3O_5$+H [(M+H)$^+$]: 684.2402, found: 684.2404.

Example 160

Preparation of chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-phenyl)-acetic acid

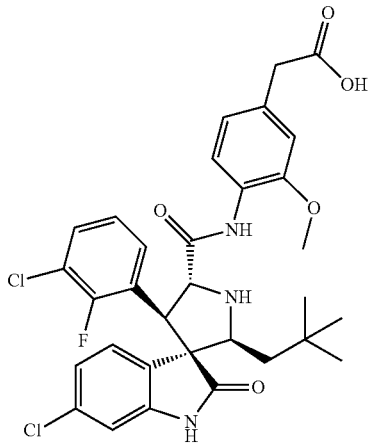

M. W. 628.53 $C_{32}H_{32}Cl_2FN_3O_5$

A solution of chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-phenyl)-acetic acid tert-butyl ester (0.16 g, 0.23 mmol) in dichloromethane (5 mL) was added trifluoroacetic acid (0.5 g). The reaction mixture was stirred at room temperature for 20 h, then concentrated. The "pH" of the residue was adjusted to 7 by aqueous saturated NaHCO$_3$ solution. The mixture was extracted with ethyl acetate three times. The combined organic extract was washed with brine, dried over MgSO$_4$, and concentrated, dried in vacuo to give chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-phenyl)-acetic acid as a light yellow solid (0.14 g, 95%).

HRMS (ES$^+$) m/z Calcd for $C_{32}H_{32}Cl_2FN_3O_5$+H [(M+H)$^+$]: 628.1776, found: 628.1775.

Example 161

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethyl-2-methoxy-phenyl)-amide

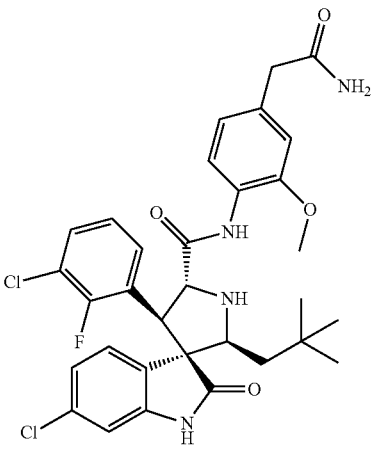

M. W. 627.54 $C_{32}H_{33}Cl_2FN_4O_4$

To a solution of chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methoxy-phenyl)-acetic acid (0.1 g, 0.17 mmol) prepared in Example 160 in anhydrous DMF (2 mL) were added EDCI (64 mg, 0.33 mmol), HOBt (45 mg, 0.33 mmol), NH$_4$Cl (89 mg, 1.67 mmol), and triethylamine (34 mg, 0.33 mmol) sequentially. The reaction mixture was heated at 80° C. for 3 h. The mixture was cooled to room temperature, then partitioned between ethyl acetate and water. The organic layer was separated, and aqueous layer was extracted with ethyl acetate twice. The combined organic extract was washed with water, brine, dried over MgSO$_4$, and concentrated. The residue was purified by chromatography (50-100% EtOAc in hexanes) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethyl-2-methoxy-phenyl)-amide as a off white solid (81 mg, 77%).

HRMS (ES$^+$) m/z Calcd for $C_{32}H_{33}Cl_2FN_4O_4$+H [(M+H)$^+$]: 627.1936, found: 627.1938.

Example 162

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-methoxy-pyridin-4-yl)-amide

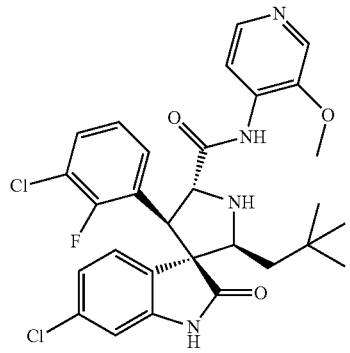

M. W. 571.48 $C_{29}H_{29}Cl_2FN_4O_3$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.26 g, 0.45 mmol), was reacted with diisopropylethylamine (0.29 g, 2.2 mmol), diphenylphosphinic chloride (0.21 g, 0.9 mmol), then reacted with 4-amino-3-methoxypyridine (Tyger) (0.08 g, 0.67 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-methoxy-pyridin-4-yl)-amide as a light yellow solid (Yield 0.11 g, 41%).

HRMS (ES$^+$) m/z Calcd for $C_{29}H_{29}Cl_2FN_4O_3$+H [(M+H)$^+$]: 571.1674, found: 571.1673.

Example 163

Preparation of intermediate
2-methoxy-N,N-dimethyl-benzene-1,4-diamine

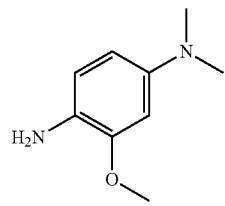

M. W. 166.22 C$_9$H$_{14}$N$_2$O

A suspension of 3-methoxy-N,N-dimethyl-4-nitroaniline (Bionet) (0.5 g, 2.6 mmol) and Pd/C (Aldrich, 10%, 0.1 g) in ethyl acetate (10 mL) was vigorously shaken in a Parr under atmosphere of H$_2$ (50 psi) for 0.5 h. The mixture was filtered through a short pad of celite. The filtrate was concentrated to give 2-methoxy-N,N-dimethyl-benzene-1,4-diamine as a dark brown oil (0.4 g, 94%).

Example 164

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylamino-2-methoxy-phenyl)-amide

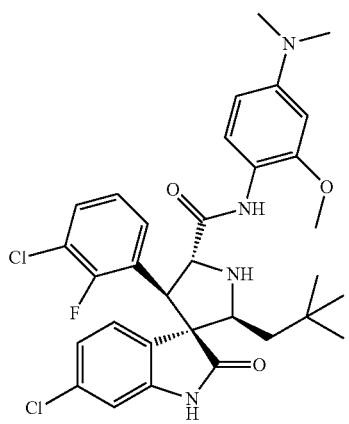

M. W. 613.56 C$_{32}$H$_{35}$Cl$_2$FN$_4$O$_3$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.2 g, 0.35 mmol), was reacted with diisopropylethylamine (0.22 g, 1.7 mmol), diphenylphosphinic chloride (0.16 g, 0.7 mmol), then reacted with 2-methoxy-N,N-dimethyl-benzene-1,4-diamine prepared in Example 163 (0.07 g, 0.45 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylamino-2-methoxy-phenyl)-amide as a light yellow solid (Yield 0.12 g, 57%).

HRMS (ES$^+$) m/z Calcd for C$_{32}$H$_{35}$Cl$_2$FN$_4$O$_3$+H [(M+H)$^+$]: 613.2143, found: 613.2142.

Example 165

Preparation of intermediate
4-amino-3-methylamino-benzoic acid methyl ester

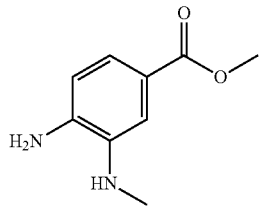

M. W. 180.21 C$_9$H$_{12}$N$_2$O$_2$

A suspension of methyl 3-(methylamino)-4-nitrobenzoate (Bionet) (0.5 g, 2.4 mmol) and Pd/C (Aldrich, 10%, 0.1 g) in ethyl acetate (7 mL) was vigorously shaken in a Parr under atmosphere of H$_2$ (50 psi) for 0.5 h. The mixture was filtered through a short pad of celite. The filtrate was concentrated to give 4-amino-3-methylamino-benzoic acid methyl ester as a dark brown foam (0.4 g, 93%).

Example 166

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methylamino-benzoic acid methyl ester

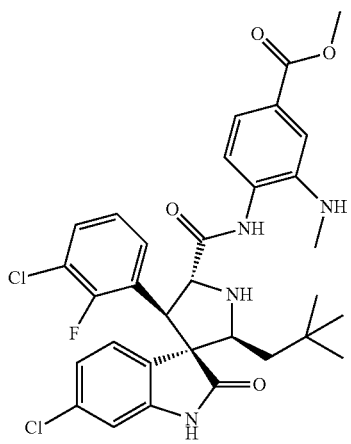

M. W. 624.54 C$_{32}$H$_{33}$Cl$_2$FN$_4$O$_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.5 g, 0.86 mmol), was reacted with diisopropylethylamine (0.56 g, 4.3 mmol), diphenylphosphinic chloride (0.41 g, 1.7 mmol), then reacted with 4-amino-3-methylamino-benzoic acid methyl ester prepared in Example 165 (0.19 g, 1 mmol) to give rac-4-{[(2'S,3'R,4'S, 5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methylamino-benzoic acid methyl ester as a light yellow solid (Yield 0.24 g, 44%).

HRMS (ES+) m/z Calcd for $C_{32}H_{33}Cl_2FN_4O_4$+H [(M+H)+]: [627.1936, found: 627.1938.

Example 167

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methylamino-benzoic acid

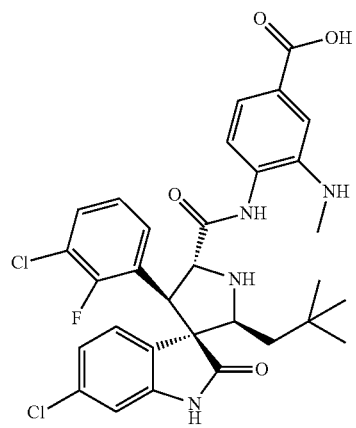

M. W. 613.51 $C_{31}H_{31}Cl_2FN_4O_4$

To a solution of rac-4-{[(2'S,3'R,4'S,5'R)-6-chloro-4'-(3-chloro-2-fluoro-phenyl)-2'-(2,2-dimethyl-propyl)-2-oxo-1, 2-dihydro-spiro[indole-3,3'-pyrrolidine]-5'-carbonyl] amino}-3-methylamino-benzoic acid methyl ester (0.22 g, 0.35 mmol) in MeOH (4 mL) and THF (12 mL) was added an aqueous solution (1N) of NaOH (7.5 mL, 7.5 mmol). The reaction mixture was stirred at room temperature for 18 h. The crude mixture was diluted with water, and acidified to "pH" 5-6 by dilute aqueous HCl solution. The mixture was then extracted with ethyl acetate three times. The combined organic extract was washed with water, brine, dried over MgSO₄, and concentrated. The residue was triturated with dichlormethane and hexanes to give rac-4-{[(2'S,3'R,4'S, 5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-3-methylamino-benzoic acid as a off white solid (Yield, 18 mg, 8%).

HRMS (ES+) m/z Calcd for $C_{31}H_{31}Cl_2FN_4O_4$+H [(M+H)+]: 613.1779, found: 613.1778.

Example 168

Preparation of intermediate 2-methoxy-4-(2-methylsulfanyl-ethoxy)-phenylamine

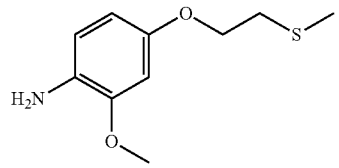

M. W. 213.30 $C_{10}H_{15}NO_2S$

Step A To a solution of 3-methoxy-4-nitrophenol (0.5 g, 3 mmol) prepared in Example 132 Step A in anhydrous DMF (13 mL) were added $K_2CO_3$ (0.8 g, 5.9 mmol) and 1-Chloro-2-methylsulfanyl-ethane (Aldrich)(0.65 g, 5.9 mmol) sequentially. The reaction mixture was heated at 70° C. for 2 h. The mixture was cooled to room temperature, and diluted with water. The mixture was extracted with ethyl acetate three times. The combined organic extract was washed with water, brine, dried over MgSO₄, and concentrated. The residue was purified by chromatography (0-40% EtOAc in hexanes) to give 2-methoxy-4-(2-methylsulfanyl-ethoxy)-1-nitro-benzene as a white solid (0.25 g, 35%).

Step B A suspension of 2-methoxy-4-(2-methylsulfanyl-ethoxy)-1-nitro-benzene (0.25 g, 1.0 mmol) in methanol (8 mL) was added an aqueous solution (4 mL) of $NH_4Cl$ (0.55 g, 10 mmol), followed by activated Zinc (Aldrich, 0.67 g, 10 mmol). The reaction mixture was stirred at room temperature for 0.5 h. The mixture was filtered through a short pad of celite. The mixture was concentrated. The residue was partitioned between ethyl acetate and water. The organic layer was separated, and aqueous layer was extracted with ethyl acetate. The combined organic extract was washed with water, brine, dried over MgSO₄, and concentrated to give 2-methoxy-4-(2-methylsulfanyl-ethoxy)-phenylamine as a brown oil (0.2 g, 91%).

Example 169

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(2-methylsulfanyl-ethoxy)-phenyl]-amide

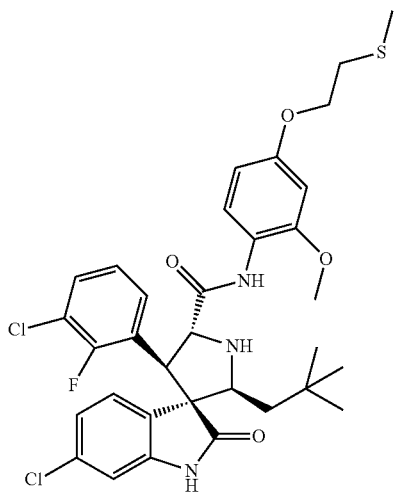

M. W. 660.63 $C_{33}H_{36}Cl_2FN_3O_4S$

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.4 g, 0.69 mmol), was reacted with diisopropylethylamine (0.45 g, 3.5 mmol), diphenylphosphinic chloride (0.33 g, 1.4 mmol), then reacted with 2-methoxy-4-(2-methylsulfanyl-ethoxy)-phenylamine prepared in Example 168 (0.2 g, 0.9 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(2-methylsulfanyl-ethoxy)-phenyl]-amide as a off white solid (Yield 0.2 g, 44%).

HRMS (ES$^+$) m/z Calcd for $C_{33}H_{36}Cl_2FN_3O_4S$+H [(M+H)$^+$]: 660.1861, found: 660.1858.

Example 170

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfonyl-ethoxy)-2-methoxy-phenyl]-amide

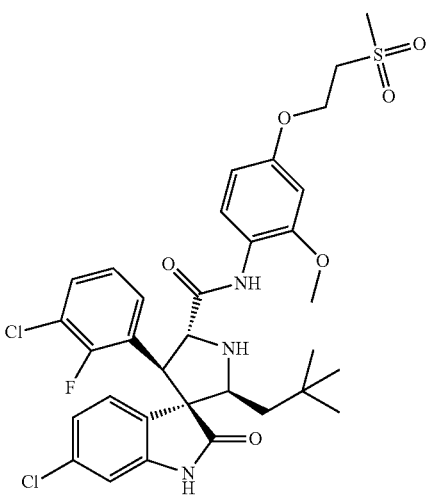

M. W. 692.63 $C_{33}H_{36}Cl_2FN_3O_6S$

To a solution of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(2-methylsulfanyl-ethoxy)-phenyl]-amide (0.17 g, 0.26 mmol) prepared in Example 169 in dichloromethane (5 mL) was added 3-chloroperoxybenzoic acid (MCPBA, Aldrich, 77%) (0.11 g mL, 0.52 mmol). The reaction mixture was stirred at room temperature for 2 h. The crude mixture was diluted with water, and extracted with dichloremethane three times. The combined organic extract was washed with aqueous saturated $Na_2S_2O_3$ solution, brine, dried over $MgSO_4$, and concentrated. TLC analysis indicated the complete consumption of starting material and the formation of two major products. The residue was purified by chromatography (0-50% EtOAc in dichlormethane) to give the first product chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfonyl-ethoxy)-2-methoxy-phenyl]-amide as a light red solid (Yield, 98 mg, 55%).

HRMS (ES$^+$) Calcd for $C_{33}H_{36}Cl_2FN_3O_6S$+H [(M+H)$^+$]: 692.1759, found: 692.1759.

Example 171

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfinyl-ethoxy)-2-methoxy-phenyl]-amide

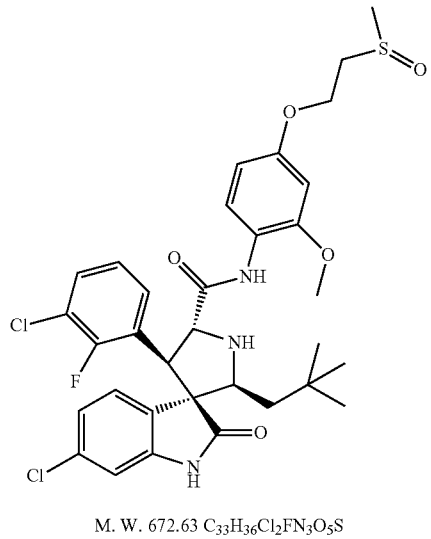

M. W. 672.63 $C_{33}H_{36}Cl_2FN_3O_5S$

In the preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfonyl-ethoxy)-2-methoxy-phenyl]-amide in Example 170, the second product chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfinyl-ethoxy)-2-methoxy-phenyl]-amide was obtained by chromatography (10% MeOH in EtOAc) as a yellow solid (Yield 63 mg, 36%).

HRMS (ES$^+$) m/z Calcd for $C_{33}H_{36}Cl_2FN_3O_5S$+H [(M+H)$^+$]: 676.1810, found: 676.1811.

Example 172

Preparation of intermediate E/Z-6-chloro-3-(3-chloro-2-fluoro-benzylidene)-7-fluoro-1,3-dihydro-indol-2-one

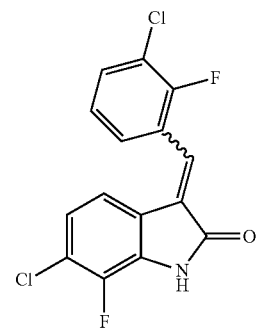

M. W. 308.14 $C_{15}H_8Cl_2FNO$

To the mixture of 6-chloro-7-fluoroindolin-2-one (1.1 g, 5.9 mmol) (Natrochem) and 3-chloro-2-fluorobenzaldehyde (1.4 g, 8.9 mmol) (Aldrich) in methanol (50 mL) was added piperidine (1.5 g, 17.8 mmol) (Aldrich) dropwise. The mixture was then heated at 50° C. for 3 h. After cooled to room temperature, the mixture was concentrated. The residue was partitioned between ethyl acetate and water. The organic layer was separated, and aqueous layer was extracted with ethyl acetate. The organic layers were combined, washed with brine, dried over MgSO$_4$, and concentrated to half its volume. The'mixture was filtered and resulting precipitate was collected, dried to give the first batch of desired product (1.4 g). The filtrate was concentrated, and residue was purified by chromatography (20-40% EtOAc in hexanes) to give the second batch of desired product (0.44 g). The two batches were combined to give E/Z-6-chloro-3-(3-chloro-2-fluoro-benzylidene)-7-fluoro-1,3-dihydro-indol-2-one as a yellow solid (Yield 1.84 g, 89%).

Example 173

Preparation of intermediate rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid tert-butyl ester

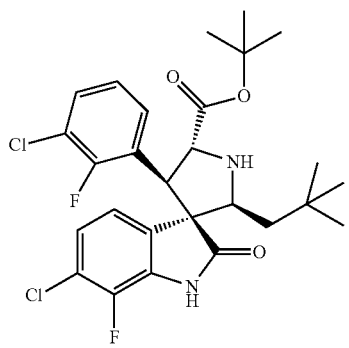

M. W. 539.45 C$_{27}$H$_{30}$Cl$_2$F$_2$N$_2$O$_3$

To a solution of [3,3-dimethyl-but-(E)-ylideneamino]-acetic acid tert-butyl ester (2 g, 9.4 mmol) prepared in Example 1 and E/Z-6-chloro-3-(3-chloro-2-fluoro-benzylidene)-7-fluoro-1,3-dihydro-indol-2-one (1.1 g, 3.4 mmol) prepared in Example 172 in dichloromethane (60 mL) were added triethylamine (1.4 mL, 10 mmol) and AgF (0.43 g, 3.4 mmol). The mixture was stirred at room temperature for 18 h. The mixture was concentrated, and the residue was partitioned between ethyl acetate and brine. The organic layer was separated, washed with water, dried over MgSO$_4$, and concentrated. The residue was dissolved into tert-butanol (20 mL), and DBU (1.5 g, 10 mmol) was added. The reaction mixture was heated at 120° C. for 2 h. The mixture was then cooled to room temperature and concentrated. The residue was partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (20-40% EtOAc in hexanes) to give as rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid tert-butyl ester a white solid (0.91 g, 50%)

Example 174

Preparation of intermediate rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid trifluoroacetic acid

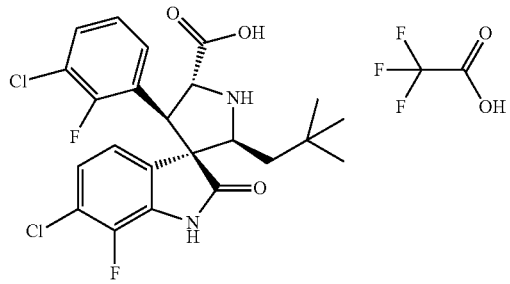

M. W. 483.35 C$_{23}$H$_{22}$Cl$_2$F$_2$N$_2$O$_3$·C$_2$HF$_3$O$_2$

A solution of rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid tert-butyl ester (0.91 g, 1.7 mmol) in dichloromethane (10 mL) was added trifluoroacetic acid (5 mL). The reaction mixture was stirred at room temperature for 20 h, then concentrated. The residue was then triturated with ethyl ether hexanes, concentrated, dried in vacuo to give rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid trifluoroacetic acid as a off white solid (0.95 g, 94%).

Example 175

Preparation of rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-phenyl)-amide

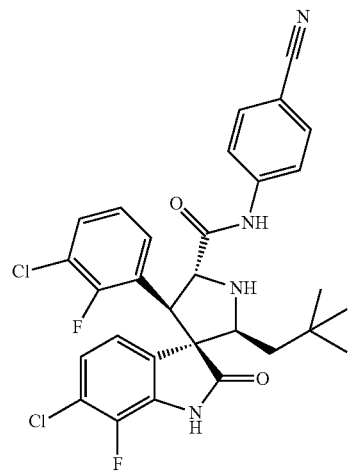

M. W. 583.46 C$_{30}$H$_{26}$Cl$_2$F$_2$N$_4$O$_2$

In a manner similar to the method described in Example 5, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid trifluoroacetic acid prepared in Example 174 (0.4 g, 0.67 mmol), was reacted with diisopropylethylamine (0.43 g, 3.4 mmol), diphenylphosphinic chloride (0.32 g, 1.3 mmol) at room temperature, then reacted with 4-aminobenzonitrile (Aldrich) (0.12 g, 1 mmol) to give rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-phenyl)-amide as a yellow solid (Yield 0.13 g, 33%).

HRMS (ES$^+$) m/z Calcd for $C_{30}H_{26}Cl_2F_2N_4O_2$+H [(M+H)$^+$]: 583.1474, found: 583.1472.

Example 176

Preparation of rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-phenyl)-amide

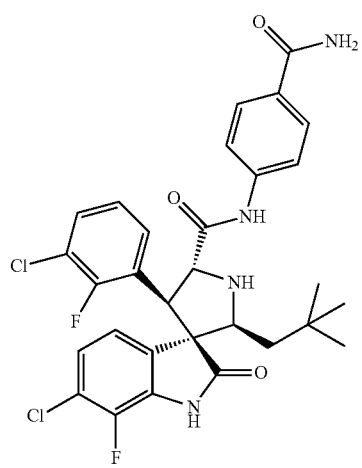

M. W. 601.48  $C_{30}H_{28}Cl_2F_2N_4O_3$

To the solution of rac-(2'S,3'S,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-phenyl)-amide (0.12 g, 0.2 mmol) prepared in Example 175 in DMSO (2 mL) at 0° C. was added an aqueous solution (30% Aldrich) of $H_2O_2$ (0.34 g, 3 mmol), then aqueous solution (1N) of NaOH (1 mL, 1 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated to give rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-phenyl)-amide as a light yellow solid (Yield 0.11 g, 93%)

HRMS (ES$^+$) m/z Calcd for $C_{30}H_{28}Cl_2F_2N_4O_3$+H [(M+H)$^+$]: 601.1580, found: 601.1578.

Example 177

Preparation of rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-2-methoxy-phenyl)-amide

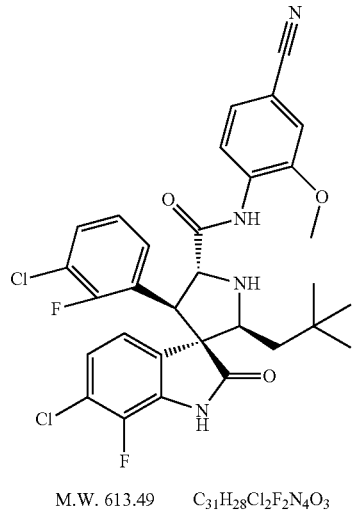

M.W. 613.49  $C_{31}H_{28}Cl_2F_2N_4O_3$

In a manner similar to the method described in Example 5, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid trifluoroacetic acid prepared in Example 174 (0.3 g, 0.5 mmol), was reacted with diisopropylethylamine (0.33 g, 2.5 mmol), diphenylphosphinic chloride (0.24 g, 1 mmol), then reacted with 4-amino-3-methoxy benzonitrile prepared in Example 57 (0.11 g, 0.8 mmol) to give rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-2-methoxy-phenyl)-amide as a off white solid (Yield 0.13 g, 33%).

HRMS (ES$^+$) m/z Calcd for $C_{31}H_{28}Cl_2F_2N_4O_3$+H [(M+H)$^+$]: 613.1580, found: 613.1578.

Example 178

Preparation of rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-2-methoxy-phenyl)-amide

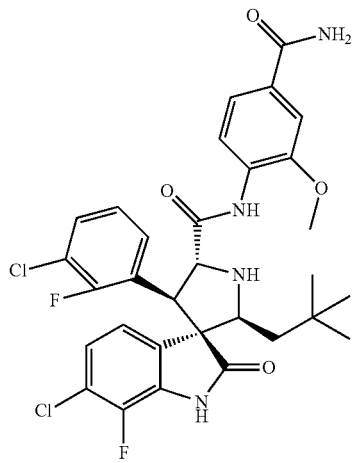

M.W. 631.50  $C_{31}H_{30}Cl_2F_2N_4O_4$

To the solution of rac-(2'S,3'R,4'S,5'R)-6-chloro-4'-(3-chloro-2-fluoro-phenyl)-2'-(2,2-dimethyl-propyl)-4-fluoro-2-oxo-1,2-dihydro-spiro[indole-3,3'-pyrrolidine]-5'-carboxylic acid (4-cyano-2-methoxy-phenyl)-amide (87 mg, 0.14 mmol) prepared in Example 177 in DMSO (2 mL) at 0° C. was added an aqueous solution (30% Aldrich) of $H_2O_2$ (0.24 g, 2 mmol), then aqueous solution (1N) of NaOH (0.7 mL, 0.7 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated to give rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-2-methoxy-phenyl)-amide as a light yellow solid (Yield 82 mg, 92%)

HRMS (ES+) m/z Calcd for $C_{31}H_{30}Cl_2F_2N_4O_4{}^4+1$ [(M+H)$^{30}$]: 631.1685, found: 631.1686.

Example 179

Preparation of rac-(2'S,3'R,4'S,512)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid [4-(2-hydroxy-ethoxy)-2-methoxy-phenyl]-amide

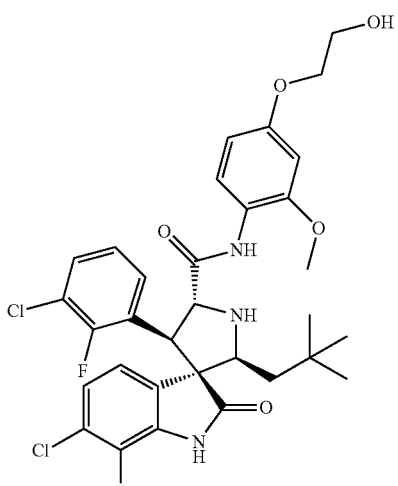

M.W. 648.53    $C_{32}H_{33}Cl_2F_2N_3O_5$

To a solution of rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid trifluoroacetic acid prepared in Example 174 (0.2 g, 0.3 mmol) in dichloromethane (3 mL) was added diisopropylethylamine (0.2 g, 1.7 mmol), diphenylphosphinic chloride (Aldrich) (0.16 g, 0.67 mmol) respectively. The mixture was stirred at room temperature for 8 min, then 4-[2-(tert-butyl-dimethyl-silanyloxy)-ethoxy]-2-methoxy-phenylamine prepared in Example 132 (0.15 g, 0.5 mmol) was added. The reaction mixture was stirred at room temperature for 2 h. The mixture was concentrated. The residue was dissolved into tetrahydrofuran (3 mL), and an aqueous solution (1N) of HCl (1 mL) was added. The reaction mixture was stirred at room temperature for 1 h, then concentrated. The residue was partitioned between ethyl acetate and aqueous saturated NaHCO$_3$ solution. The organic layer was separated, and aqueous layer was extracted with ethyl acetate twice. The combined organic extract was washed with water, brine, dried over Na$_2$SO$_4$, then concentrated. The residue was purified by chromatography (0-50% of EtOAc in CH$_2$Cl$_2$) to give rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid [4-(2-hydroxy-ethoxy)-2-methoxy-phenyl]-amide as a yellow solid (85 mg, 39%).

HRMS (ES+) m/z Calcd for $C_{32}H_{33}Cl_2F_2N_3O_5$+H [(M+H)+]: 648.1838, found: 648.1837.

Example 180

Preparation of intermediate 4-(3-methanesulfonyl-propoxy)-2-methoxy-phenylamine

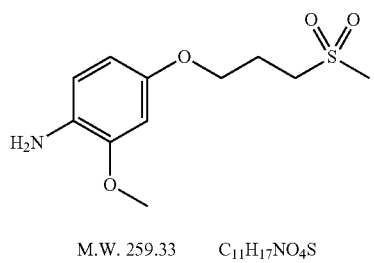

M.W. 259.33    $C_{11}H_{17}NO_4S$

Step A To a solution of 3-methanesulfonyl-propan-1-ol (Cambridge) (0.5 g, 3.6 mmol) in dichloromethane (3 mL) at 0° C. was added triethylamine (0.5 g, 5 mmol), and methanesulfonyl chloride (0.3 mL, 4 mmol, Aldrich). The reaction mixture was stirred at 0° C. for 2 h. The mixture was poured into water, extracted with dichloromethane. The organic layer was separated, washed with water, brine, dried over MgSO$_4$, and concentrated to give crude methanesulfonic acid 3-methanesulfonyl-propyl ester as a yellow oil (Yield 0.7 g, 90%).

Step B To a solution of 3-methoxy-4-nitrophenol (0.5 g, 3 mmol) prepared in Example 132 Step A in anhydrous DMF (25 mL) were added K$_2$CO$_3$ (0.8 g, 5.9 mmol) and methanesulfonic acid 3-methanesulfonyl-propyl ester (0.7 g, 3.2 mmol) sequentially. The reaction mixture was heated at 70° C. for 4 h. The mixture was cooled to room temperature, and diluted with water. The mixture was extracted with ethyl acetate three times. The combined organic extract was washed with water, brine, dried over MgSO$_4$, and concentrated to give 2-methoxy-4-(3-(methylsulfonyl)propoxy)-1-nitrobenzene as a off white solid (0.58 g, 68%).

Step C A suspension of 2-methoxy-4-(3-(methylsulfonyl)propoxy)-1-nitrobenzene (0.4 g, 1.6 mmol) and Pd/C (Aldrich, 10%, 0.1 g) in methanol (15 mL) was vigorously shaken in a Parr under atmosphere of H$_2$ (50 psi) for 0.5 h. The mixture was filtered through a short pad of celite. The filtrate was concentrated to give 4-(3-methanesulfonyl-propoxy)-2-methoxy-phenylamine as a black oil (0.48 g, 92%).

Example 181

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(3-methanesulfonyl-propoxy)-2-methoxy-phenyl]-amide

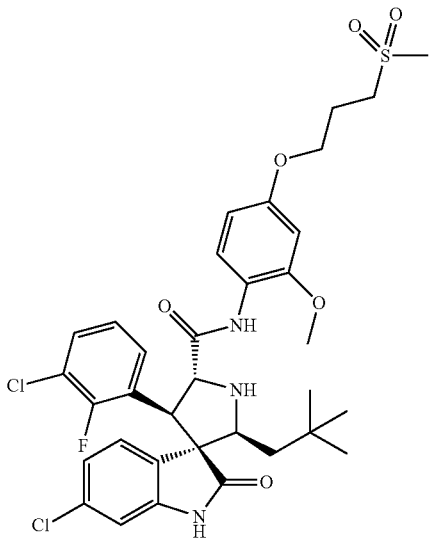

M.W. 706.66    $C_{34}H_{38}Cl_2FN_3O_6S$

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.2 g, 0.35 mmol), was reacted with diisopropylethylamine (0.22 g, 1.7 mmol), diphenylphosphinic chloride (0.16 g, 0.7 mmol), then reacted with 4-(3-methanesulfonyl-propoxy)-2-methoxy-phenylamine prepared in Example 180 (0.13 g, 0.5 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(3-methanesulfonyl-propoxy)-2-methoxy-phenyl]amide as a yellow solid (Yield 0.13 g, 51%).

HRMS (ES+) m/z Calcd for $C_{34}H_{38}Cl_2FN_3O_6S+H$ [(M+H)+]: 706.1915, found: 706.1912.

Example 182

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-cyano-pyridin-3-yl)-amide

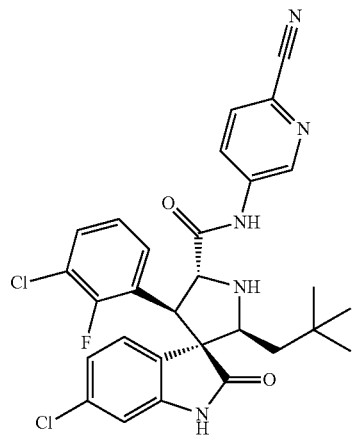

M.W. 566.46    $C_{29}H_{26}Cl_2FN_5O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.33 g, 0.57 mmol), was reacted with diisopropylethylamine (0.37 g, 2.9 mmol), diphenylphosphinic chloride (0.27 g, 1.1 mmol), then reacted with 3-amino-6-cyanopyridine (Aldrich) (0.1 g, 0.9 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-cyano-pyridin-3-yl)-amide as a yellow solid (Yield 0.12 g, 38%).

HRMS (ES+) m/z Calcd for $C_{29}H_{26}Cl_2FN_5O_2+H$ [(M+H)+]: 566.1521, found: 566.1521.

Example 183

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-carbamoyl-pyridin-3-yl)-amide

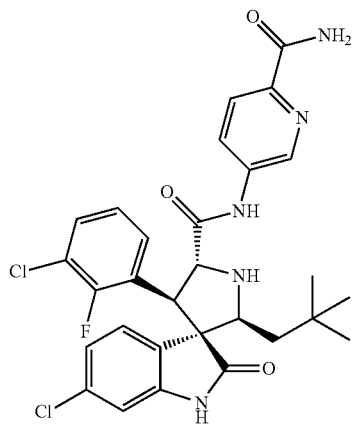

M.W. 584.48    $C_{29}H_{28}Cl_2FN_5O_3$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-cyano-pyridin-3-yl)-amide (0.12 g, 0.2 mmol) prepared in Example 182 in DMSO (2 mL) at 0° C. was added an aqueous solution (30% Aldrich) of $H_2O_2$ (0.36 g, 3 mmol), then aqueous solution (1N) of NaOH (1 mL, 1 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-carbamoyl-pyridin-3-yl)-amide as a white solid (Yield 80 mg, 65%)

HRMS (ES$^+$) m/z Calcd for $C_{29}H_{28}Cl_2FN_5O_3$+H [(M+H)$^{3o}$]: 584.1626, found: 584.1625.

Example 184

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-cyano-pyrimidin-5-yl)-amide

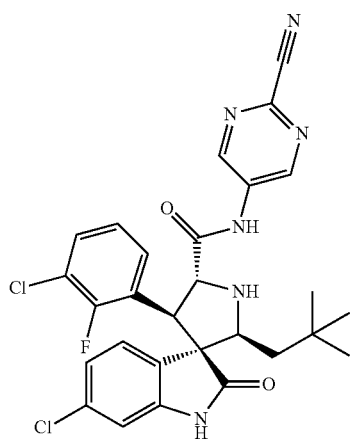

M.W. 567.45   $C_{28}H_{25}Cl_2FN_6O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.33 g, 0.57 mmol), was reacted with diisopropylethylamine (0.37 g, 2.9 mmol), diphenylphosphinic chloride (0.27 g, 1.1 mmol), then reacted with 5-aminopyrimidine-2-carbonitrile (Accelachem) (0.1 g, 0.9 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-cyano-pyrimidin-5-yl)-amide as a yellow solid (Yield 30 mg, 9%).

Example 185

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-carbamoyl-pyrimidin-5-yl)-amide

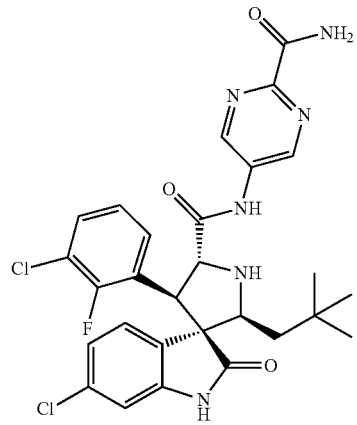

M.W. 585.46   $C_{28}H_{27}Cl_2FN_6O_3$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-cyano-pyrimidin-5-yl)-amide (30 mg, 0.05 mmol) prepared in Example 184 in DMSO (0.2 mL) at 0° C. was added an aqueous solution (30% Aldrich) of $H_2O_2$ (0.09 g, 0.8 mmol), then aqueous solution (1N) of NaOH (0.3 mL, 0.3 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-carbamoyl-pyrimidin-5-yl)-amide as a white solid (Yield 8 mg, 26%)

HRMS (ES$^+$) m/z Calcd for $C_{28}H_{27}Cl_2FN_6O_3$+H [(M+H)$^+$]: 585.1579, found: 585.1582.

Example 186

Preparation of intermediate 5-amino-thiophene-2-carbonitrile

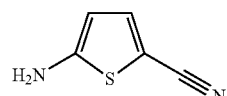

M.W. 124.17   $C_5H_4N_2S$

A suspension of 5-nitrothiophene-2-carbonitrile (Lancaster) (1 g, 6.5 mmol) in methanol (30 mL) was added an aqueous solution (30 mL) of $NH_4Cl$ (4.5 g, 65 mmol), followed by activated Zinc (Aldrich, 4.2 g, 65 mmol). The reaction mixture was stirred at room temperature for 0.5 h. The mixture was filtered through a short pad of celite. The mixture was concentrated. The residue was partitioned between ethyl acetate and water. The organic layer was separated, and aqueous layer was extracted with ethyl acetate. The combined organic extract was washed with water, brine, dried over MgSO$_4$, and concentrated to give 5-amino-thiophene-2-carbonitrile as a yellow solid (0.7 g, 87%).

Example 187

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide

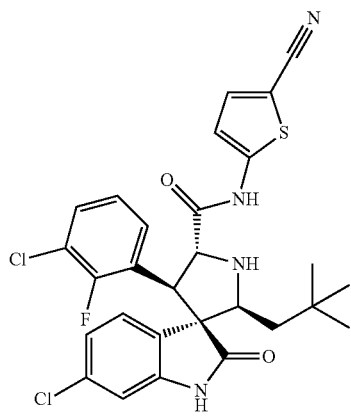

M.W. 571.50    C$_{28}$H$_{25}$Cl$_2$FN$_4$O$_2$S

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol), was reacted with diisopropylethylamine (0.34 g, 2.6 mmol), diphenylphosphinic chloride (0.37 g, 1.6 mmol), then reacted with 5-amino-thiophene-2-carbonitrile prepared in Example 186 (0.11 g, 0.85 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide as a white solid (Yield 0.12 g, 37%).

HRMS (ES$^+$) m/z Calcd for C$_{28}$H$_{25}$Cl$_2$FN$_4$O$_2$S+H [(M+H)$^+$]: 571.1132, found: 571.1131.

Example 188

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide

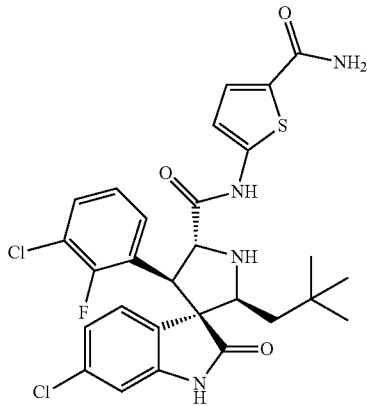

M.W. 589.52    C$_{28}$H$_{27}$Cl$_2$FN$_4$O$_3$S

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide (0.1 g, 0.18 mmol) prepared in Example 187 in DMSO (2 mL) at 0° C. was added an aqueous solution (30% Aldrich) of H$_2$O$_2$ (0.3 g, 2.6 mmol), then aqueous solution (1N) of NaOH (0.9 mL, 0.9 mmol) was added dropwise. The reaction mixture was stirred at 0° C. for 1 h. The mixture was partitioned between ethyl acetate and saturated aqueous Na$_2$SO$_3$ solution. The organic layer was separated, washed with water, brine, dried over MgSO$_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide as a white solid (Yield 40 mg, 39%)

MS (ES$^+$) m/z Calcd for C$_{28}$H$_{27}$Cl$_2$FN$_4$O$_3$S+H [(M+H)$^{3o}$]: 589.1238, found: 589.1238.

Example 189

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide

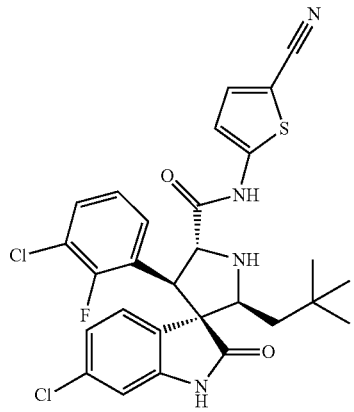

M.W. 571.50    C$_{28}$H$_{25}$Cl$_2$FN$_4$O$_2$S

In a manner similar to the method described in Example 5, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.46 g, 0.79 mmol), was reacted with diisopropylethylamine (0.51 g, 4 mmol), diphenylphosphinic chloride (0.38 g, 1.6 mmol), then reacted with 5-amino-thiophene-2-carbonitrile prepared in Example 186 (0.15 g, 1.2 mmol) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide as a yellow solid (Yield 0.12 g, 26%).

HRMS (ES$^+$) m/z Calcd for $C_{28}H_{25}Cl_2FN_4O_2S+H$ [(M+H)$^+$]: 571.1132, found: 571.1131.

Example 190

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide

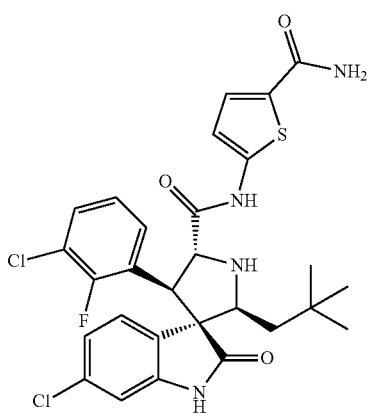

M.W. 589.52   $C_{28}H_{27}Cl_2FN_4O_3S$

To the solution of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide (0.11 g, 0.19 mmol) prepared in Example 189 in DMSO (2 mL) at 0° C. was added an aqueous solution (30% Aldrich) of $H_2O_2$ (0.33 g, 2.9 mmol), then aqueous solution (1N) of NaOH (0.96 mL, 0.96 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over $MgSO_4$, and concentrated. The residue was purified by chromatography (50-100% EtOAc in dichloromethane) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-f-yl)-amide as a off white solid (Yield 40 mg, 35%)

MS (ES$^+$) m/z Calcd for $C_{28}H_{27}Cl_2FN_4O_3S+H$ [(M+H)$^+$]: 589.1238, found: 589.1239.

Example 191

Preparation of intermediate 6-[2-(tert-butyl-dimethyl-silanyloxy)-ethoxy]-4-methoxy-pyridin-3-ylamine

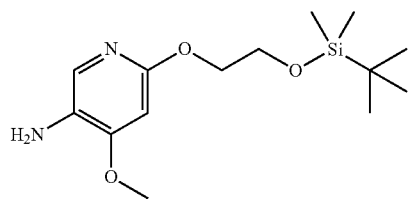

M.W. 298.46   $C_{14}H_{26}N_2O_3Si$

Step A To a solution of 4-methoxy-5-nitropyridin-2-ol (0.5 g, 2.9 mmol) in anhydrous DMF (12 mL) were added $K_2CO_3$ (0.82 g, 5.9 mmol) and (2-bromoethoxy)(tert-butyl)dimethylsilane (0.7 g, 2.9 mmol) sequentially. The reaction mixture was heated at 70° C. for 2 h. The mixture was cooled to room temperature, and diluted with water. The mixture was extracted with ethyl acetate three times. The combined organic extract was washed with water, brine, dried over $MgSO_4$, and concentrated to give 2-(2-(tert-butyldimethylsilyloxy)ethoxy)-4-methoxy-5-nitropyridine as a white solid (0.9 g, 93%).

Step B A suspension of 2-(2-(tert-butyldimethylsilyloxy)ethoxy)-4-methoxy-5-nitropyridine (0.9 g, 2.7 mmol) and Pd/C (Aldrich, 10%, 0.15 g) in ethyl acetate (10 mL) was vigorously shaken in a Parr under atmosphere of $H_2$ (50 psi) for 45 min. The mixture was filtered through a short pad of celite. The filtrate was concentrated to give 6-[2-(tert-butyl-dimethyl-silanyloxy)-ethoxy]-4-methoxy-pyridin-3-ylamine as a off white gum (0.6 g, 73%).

Example 192

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [6-(2-hydroxy-ethoxy)-4-methoxy-pyridin-3-yl]-amide

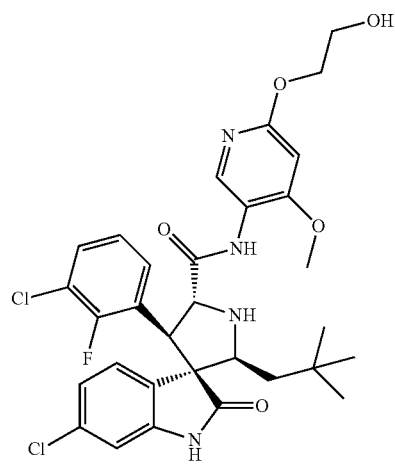

M.W. 631.53
$C_{31}H_{33}Cl_2FN_4O_5$

To a solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol) in dichloromethane (9 mL) was added diisopropylethylamine (0.34 g, 2.6 mmol), diphenylphosphinic chloride (Aldrich) (0.24 g, 1 mmol) respectively. The mixture was stirred at room temperature for 8 min, then 6-[2-(tert-butyl-dimethyl-silanyloxy)-ethoxy]-4-methoxy-pyridin-3-ylamine prepared in Example 191 (0.23 g, 0.78 mmol) was added. The reaction mixture was stirred at room temperature for 48 h. The mixture was concentrated. The residue was dissolved into tetrahydrofuran (3 mL), and an aqueous solution (1N) of HCl (1 mL) was added. The reaction mixture was stirred at room temperature for 1 h, then concentrated. The residue was partitioned between ethyl acetate and aqueous saturated NaHCO₃ solution. The organic layer was separated, and aqueous layer was extracted with ethyl acetate twice. The combined organic extract was washed with water, brine, dried over Na₂SO₄, then concentrated. The residue was purified by chromatography (0-15% MeOH in CH₂Cl₂) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [6-(2-hydroxy-ethoxy)-4-methoxy-pyridin-3-yl]-amide as a white solid (0.15 g, 46%).

HRMS (ES⁺) m/z Calcd for $C_{31}H_{33}Cl_2FN_4O_5$+H [(M+H)⁺]: 631.1885, found: 631.1881.

Example 193

Preparation of intermediate
5-amino-1-methyl-1H-pyrrole-2-carboxylic acid tert-butyl ester

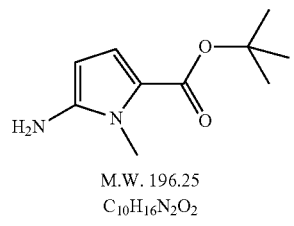

M.W. 196.25
$C_{10}H_{16}N_2O_2$

A suspension of tert-butyl 1-methyl-4-nitro-1H-pyrrole-2-carboxylate (Oakwood) (1.5 g, 6.6 mmol) and Pd/C (Aldrich, 10%, 0.15 g) in methanol (15 mL) was vigorously shaken in a Parr under atmosphere of H₂ (50 psi) for 45 min. The mixture was filtered through a short pad of celite. The filtrate was concentrated to give 5-amino-1-methyl-1H-pyrrole-2-carboxylic acid tert-butyl ester as a yellow foam (1.2 g, 92%).

Example 194

Preparation of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-1-methyl-1H-pyrrole-2-carboxylic acid tert-butyl ester

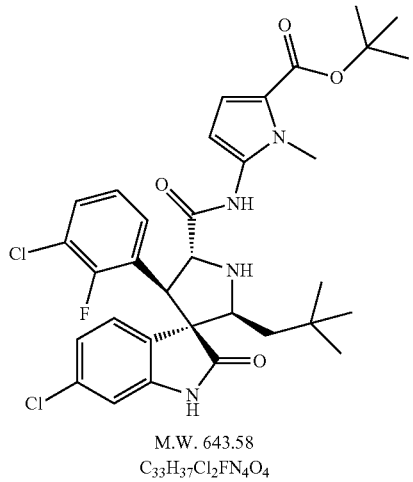

M.W. 643.58
$C_{33}H_{37}Cl_2FN_4O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol), was reacted with diisopropylethylamine (0.34 g, 2.6 mmol), diphenylphosphinic chloride (0.25 g, 1 mmol), then reacted with 5-amino-1-methyl-1H-pyrrole-2-carboxylic acid tert-butyl ester prepared in Example 193 (0.15 g, 0.78 mmol) to give rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-1-methyl-1H-pyrrole-2-carboxylic acid tert-butyl ester as a yellow solid (Yield 0.12 g, 36%).

HRMS (ES⁺) m/z Calcd for $C_{33}H_{37}Cl_2FN_4O_4$+H [(M+H)⁺]: 643.2249, found: 643.2247.

Example 195

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-1H-pyrrol-2-yl)-amide

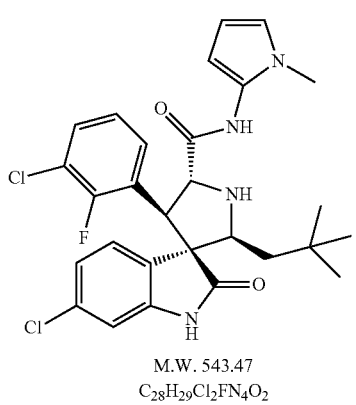

M.W. 543.47
$C_{28}H_{29}Cl_2FN_4O_2$

A solution of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-1-methyl-1H-pyrrole-2-carboxylic acid tert-butyl ester (0.1 g, 0.16 mmol) in dichloromethane (2 mL) was added trifluoroacetic acid (2 mL). The reaction mixture was stirred at room temperature for 20 h, then concentrated. To the residue was added aqueous saturated NaHCO$_3$ solution until "pH" became 7-8, and the mixture was extracted with ethyl acetate several times. The combined organic extract was washed with water, brine, dried over MgSO$_4$, and concentrated to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-1H-pyrrol-2-yl)-amide as a light brown solid (95 mg, 93%).

HRMS (ES$^+$) m/z Calcd for $C_{28}H_{29}Cl_2FN_4O_2$+H [(M+H)$^+$]: 543.1725, found: 543.1723.

Example 196

Preparation of rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid ethyl ester

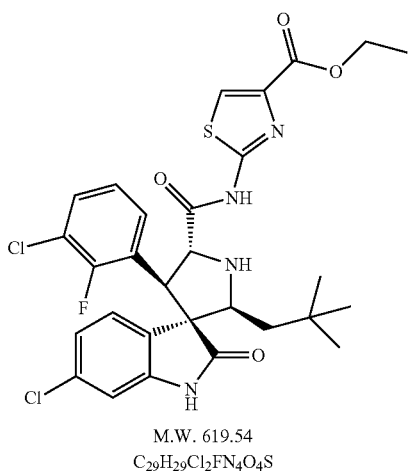

M.W. 619.54
$C_{29}H_{29}Cl_2FN_4O_4S$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol), was reacted with diisopropylethylamine (0.34 g, 2.6 mmol), diphenylphosphinic chloride (0.25 g, 1 mmol), then reacted with ethyl 2-aminothiazole-4-carboxylate (Oakwood) (0.13 g, 0.78 mmol) to give rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-thiazole-4-carboxylic acid ethyl ester as a off white solid (Yield 0.1 g, 31%).

HRMS (ES$^+$) m/z Calcd for $C_{29}H_{29}Cl_2FN_4O_4S$+H [(M+H)$^+$]: 619.1344, found: 619.1345.

Example 197

Preparation of rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-thiazole-4-carboxylic acid

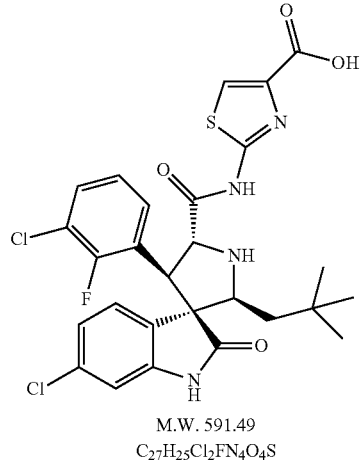

M.W. 591.49
$C_{27}H_{25}Cl_2FN_4O_4S$

To a solution of rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid ethyl ester (80 mg, 0.13 mmol) in MeOH (3 mL) and THF (9 mL) was added an aqueous solution (1N) of NaOH (6 mL, 6 mmol). The reaction mixture was stirred at room temperature for 18 h. The crude mixture was diluted with water, and acidified to "pH" 5-6 by dilute aqueous HCl solution. The mixture was then extracted with ethyl acetate three times.

The combined organic extract was washed with water, brine, dried over MgSO$_4$, and concentrated to give rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid as a off white solid (Yield, 55 mg, 72%).

HRMS (ES$^+$) m/z Calcd for $C_{27}H_{25}Cl_2FN_4O_4S$+H [(M+H)$^+$]: 591.1031, found: 591.1031.

Example 198

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-thiazol-2-yl)-amide

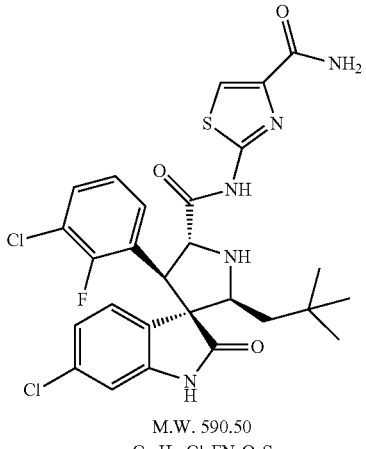

M.W. 590.50
$C_{27}H_{26}Cl_2FN_5O_3S$

To a solution of rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid (40 mg, 0.07 mmol) prepared in Example 197 in anhydrous DMF (2 mL) were added EDCI (26 mg, 0.13 mmol), HOBt (18 mg, 0.13 mmol), NH$_4$Cl (36 mg, 0.67 mmol), and triethylamine (14 mg, 0.13 mmol) sequentially. The reaction mixture was heated at 80° C. for 1 h. The mixture was cooled to room temperature, then partitioned between ethyl acetate and water. The organic layer was separated, and aqueous layer was extracted with ethyl acetate twice. The combined organic extract was washed with water, brine, dried over MgSO$_4$, and concentrated. The residue was purified by chromatography (25-100% EtOAc in dichloromethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-thiazol-2-yl)-amide as a off white solid (12 mg, 30%).

HRMS (ES$^+$) m/z Calcd for $C_{27}H_{26}Cl_2FN_5O_3S$+H [(M+H)$^+$]: 590.1190, found: 590.1190.

Example 199

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-pyridin-2-yl)-amide

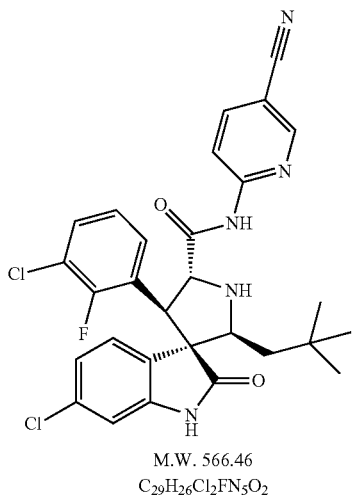

M.W. 566.46
$C_{29}H_{26}Cl_2FN_5O_2$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol), was reacted with diisopropylethylamine (0.34 g, 2.6 mmol), diphenylphosphinic chloride (0.24 g, 1 mmol), then reacted with 6-aminonicotinonitrile (Oakwood) (0.09 g, 0.8 mmol) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-pyridin-2-yl)-amide as a yellow solid (Yield 12 mg, 4%).

MS (ES$^+$) m/z Calcd for $C_{29}H_{26}Cl_2FN_5O_2$+H [(M+H)$^+$]: 566, found: 566.

Example 200

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-pyridin-2-yl)-amide

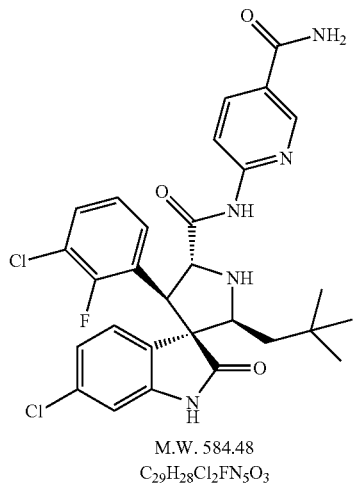

M.W. 584.48
$C_{29}H_{28}Cl_2FN_5O_3$

To the solution of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-pyridin-2-yl)-amide (12 mg, 0.02 mmol) prepared in Example 199 in DMSO (0.2 mL) at 0° C. was added an aqueous solution (30% Aldrich) of $H_2O_2$ (0.04 g, 0.3 mmol), then aqueous solution (1N) of NaOH (0.1 mL, 0.1 mmol) was added dropwise. The reaction mixture was stirred at 0° C. for 1 h. The mixture was partitioned between ethyl acetate and saturated aqueous $Na_2SO_3$ solution. The organic layer was separated, washed with water, brine, dried over MgSO$_4$, and concentrated. The residue was purified by chromatography (50-100% EtOAc in dichloromethane) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-pyridin-2-yl)-amide as a light yellow solid (Yield 5 mg, 40%)

HRMS (ES$^+$) m/z Calcd for $C_{29}H_{28}Cl_2FN_5O_3$+H [(M+H)$^+$]: 584.1626, found: 584.1624.

Example 201

Preparation of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-furan-2-carboxylic acid methyl ester

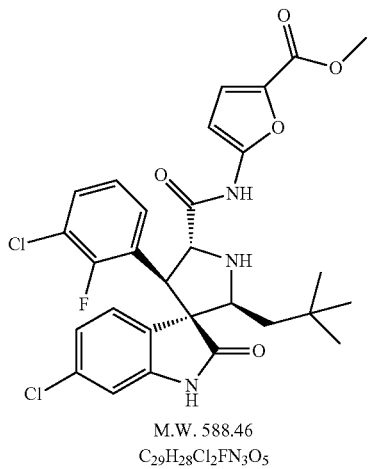

M.W. 588.46
$C_{29}H_{28}Cl_2FN_3O_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (0.3 g, 0.52 mmol), was reacted with diisopropylethylamine (0.34 g, 2.6 mmol), diphenylphosphinic chloride (0.25 g, 1 mmol), then reacted with methyl 5-aminofuran-2-carboxylate (Lancaster) (0.11 g, 0.78 mmol) to give rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-furan-2-carboxylic acid methyl ester as a yellow solid (Yield 5 mg, 2%).

HRMS (ES$^+$) m/z Calcd for $C_{29}H_{28}Cl_2FN_3O_5$+H [(M+H)$^+$]: 588.1463, found: 588.1464.

Example 202

Preparation of intermediate acetic acid 2-(4-amino-2-methoxy-phenoxy)-ethyl ester

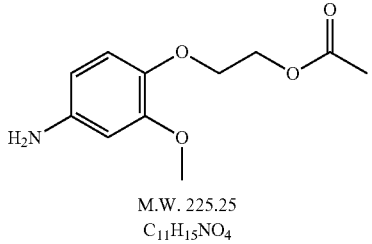

M.W. 225.25
$C_{11}H_{15}NO_4$

Step A. To a solution of 2-methoxy-4-nitrophenol (5 g, 30 mmol) in anhydrous DMF (50 mL) were added $K_2CO_3$ (6.6 g, 47 mmol) and (2-bromoethoxy)(tert-butyl)dimethylsilane (8.5 g, 36 mmol) sequentially. The reaction mixture was heated at 70° C. for 20 h. The mixture was cooled to room temperature, and diluted with water. The mixture was extracted with ethyl acetate three times. The combined organic extract was washed with water, brine, dried over $MgSO_4$, and concentrated to give tert-butyl-[2-(2-methoxy-4-nitro-phenoxy)-ethoxy]-dimahyl-silane as a brown oil (9 g, 93%).

Step B. To a solution of tert-butyl-[2-(2-methoxy-4-nitro-phenoxy)-ethoxy]-dimethyl-silane (9 g, 27.5 mmol) in THF (10 mL) was added an aqueous HCl solution (2 N, 10 mL, 20 mmol). The reaction mixture was stirred at room temperature for 2 h. The mixture was concentrated. The residue was partitioned between ethyl acetate and saturated aqueous $NaHCO_3$ solution. The organic layer was separated, and aqueous layer was extracted with ethyl acetate. The combined organic extract was washed with water, brine, dried over $MgSO_4$, and concentrated to give 2-(2-methoxy-4-nitrophenoxy)ethanol as a off white solid (5.5 g, 94%).

Step C. To a solution of 2-(2-methoxy-4-nitrophenoxy)ethanol (5.5 g, 26 mmol) and pyridine (2.35 g, 30 mmol) in THF (140 mL) at 0° C. was acetyl chloride (2.33 g, 30 mmol). The reaction mixture was warmed to room temperature and stirred for 1 h. The mixture was concentrated. The residue was partitioned between ethyl acetate and water. The organic layer was separated, and aqueous layer was extracted with ethyl acetate. The combined organic extract was washed with water, saturated aqueous $CuSO_4$ solution, brine, dried over $MgSO_4$, and concentrated to give 2-(2-methoxy-4-nitrophenoxy)ethyl acetate as a yellow solid (6 g, 91%).

Step D. A suspension of 2-(2-methoxy-4-nitrophenoxy) ethyl acetate (1.5 g, 5.9 mmol) and Pd/C (Aldrich, 10%, 0.2 g) in ethyl acetate (19 mL) was vigorously shaken in a Parr under atmosphere of $H_2$ (50 psi) for 2 h. The mixture was filtered through a short pad of celite. The filtrate was concentrated to give acetic acid 2-(4-amino-2-methoxy-phenoxy)-ethyl ester as a light brown oil (1.32 g, 91%).

Example 203

Preparation of acetic acid chiral 2-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-phenoxy)-ethyl ester

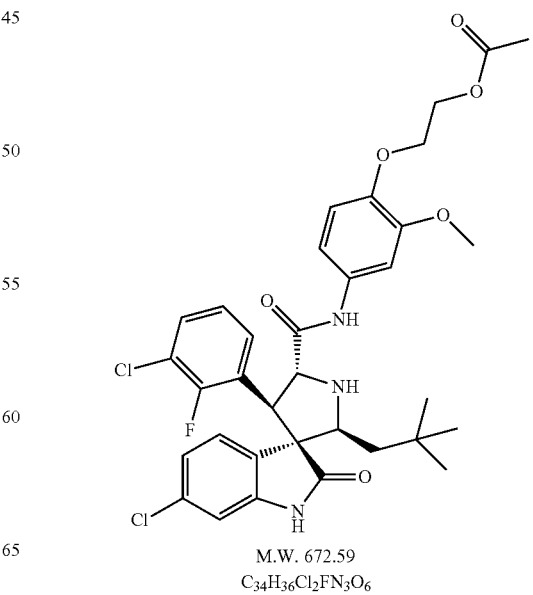

M.W. 672.59
$C_{34}H_{36}Cl_2FN_3O_6$

To a solution of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (0.4 g, 0.7 mmol) in dichloromethane (3 mL) was added diisopropylethylamine (0.45 g, 3.5 mmol), diphenylphosphinic chloride (Aldrich) (0.33 g: 1.4 mmol) respectively. The mixture was stirred at room temperature for 8 min, then acetic acid 2-(4-amino-2-methoxy-phenoxy)-ethyl ester (0.23 g, 1 mmol) was added. The reaction mixture was stirred at room temperature for 20 h. The mixture was concentrated. The residue was partitioned between ethyl acetate and water. The organic layer was separated, washed with water, brine, dried over $Na_2SO_4$, then concentrated. The residue was purified by chromatography (0-15% of EtOAc in $CH_2Cl_2$) to give acetic acid chiral 2-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-phenoxy)-ethyl ester as a off white solid (0.28 g, 60%).

HRMS (ES$^+$) m/z Calcd for $C_{34}H_{36}Cl_2FN_3O_6$+H [(M+H)$^+$]: 672.2038, found: 672.2039.

Example 204

Preparation of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-3-methoxy-phenyl]-amide

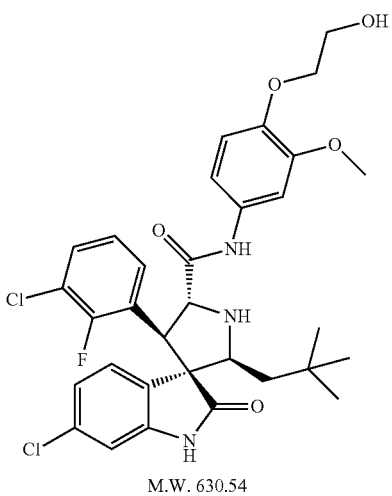

M.W. 630.54
$C_{32}H_{34}Cl_2FN_4O_5$

To a solution of acetic acid chiral 2-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-methoxy-phenoxy)-ethyl ester (25 mg, 0.04 mmol) in THF (1 mL) was added an aqueous solution (1N) of NaOH (1 mL, 1 mmol). The reaction mixture was stirred at room temperature for 3 h. The mixture was concentrated. The residue was diluted with water, and the mixture was then extracted with ethyl acetate three times. The combined organic extract was washed with water, brine, dried over $MgSO_4$, and concentrated. The residue was purified by chromatography (0-100% EtOAc in dichloromethane) to give chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-3-methoxy-phenyl]-amide as a off white solid (Yield, 10 mg, 43%).

HRMS MS (ES$^+$) m/z Calcd for $C_{32}H_{34}Cl_2FN_3O_5$+H [(M+H)$^+$]: 630.1933, found: 630.1934.

Example 205

Preparation of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid methyl ester

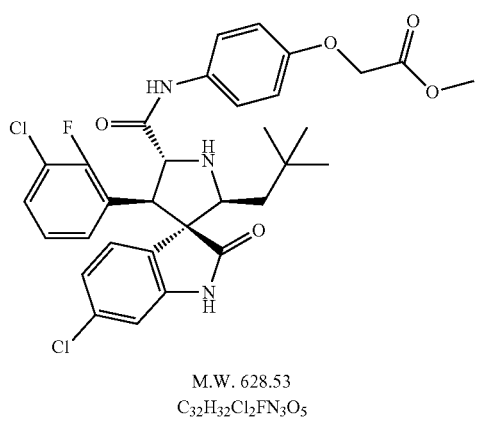

M.W. 628.53
$C_{32}H_{32}Cl_2FN_3O_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (80 mg, 0.138 mmol), was reacted with diisopropylethylamine (89 mg, 0.69 mmol), diphenylphosphinic chloride (80 mg, 0.34 mmol), then reacted with methyl 2-(4-aminophenoxy)acetate (Aldrich, 27 mg, 0.153 mmol) to give rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid methyl ester (51 mg, 59%). MS (ES$^+$) m/z [(M+H)$^{3o}$]: 628

Example 206

Preparation of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenoxy)-acetic acid

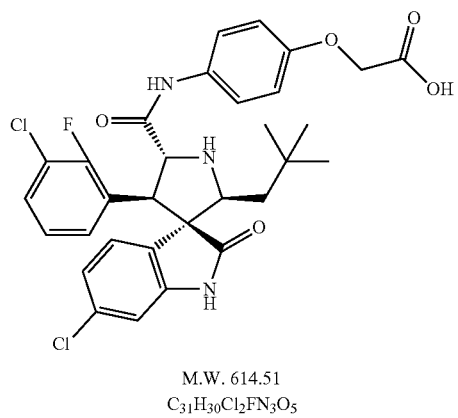

M.W. 614.51
$C_{31}H_{30}Cl_2FN_3O_5$

To a solution of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid methyl ester (45 mg, 0.071 mmol) in THF (3 mL) was added LiOH monohydrate (13 mg, 0.30 mmol) in water (2 mL) and the reaction mixture was allowed to stir at rt overnight. The mixture was then treated with 1N HCl to slightly acidic, diluted with ethyl acetate (80 mL), washed with water (2×15 mL), dried with Na$_2$SO$_4$ and concentrated to give rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid as a white solid (36 mg, 80%). MS (ES$^+$) m/z [(M+H)$^+$]: 614

Example 207

Preparation of intermediate methyl 3-(4-aminophenyl)propanoate

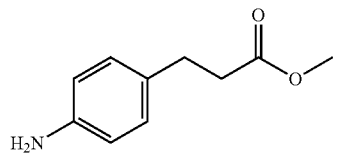

M. W. 179.22
C$_{10}$H$_{13}$NO$_2$

Thionyl chloride (Aldrich, 4.08 g, 2.5 ml, 34.3 mmol) was added dropwise to anhydrous MeOH (10mL) in ice-water-salt bath. After 20 min, 3-(4-aminophenyl)propionic acid (Trans World Chemicals, 1.7 g, 10.3 mmol) was added and the reaction mixture was allowed to stir at rt overnight. The resulting reaction mixture was concentrated in vacuo and the residue was diluted with EtOAc, washed with sat. aqueous NaHCO$_3$, water, and brine. The organic layer was dried over Na$_2$SO$_4$ and concentrated in vacuo to give methyl 3-(4-aminophenyl)propanoate (1.80 g, 98%).

Example 208

Preparation of rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid methyl ester

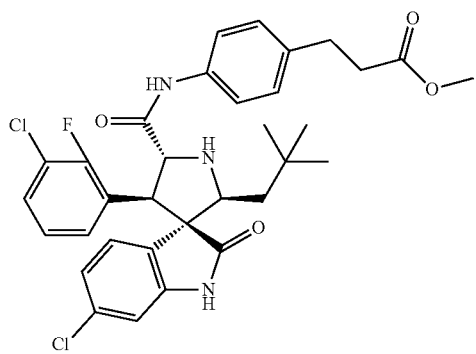

M. W. 626.56
C$_{33}$H$_{34}$Cl$_2$FN$_3$O$_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (100 mg, 0.173 mmol), was reacted with diisopropylethylamine (112 mg, 0.863 mmol), diphenylphosphinic chloride (106 mg, 0.446 mmol), then reacted with methyl 3-(4-aminophenyl)propanoate (31 mg, 0.173 mmol) to give rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid methyl ester (108 mg, 56%). MS (ES$^+$) m/z [(M+H)$^+$]: 626

Example 209

Preparation of rac-3-(4-{[(2'S,3'R,4'S,5'12)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid

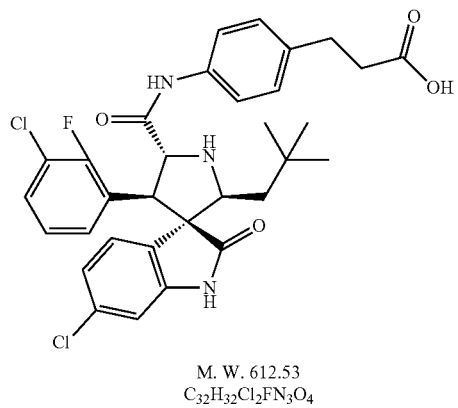

M. W. 612.53
C$_{32}$H$_{32}$Cl$_2$FN$_3$O$_4$

To a solution of rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid methyl ester (49 mg, 0.078 mmol) in THF (3 mL) was added LiOH monohydrate (14 mg, 0.326 mmol) in water (2 mL) and the reaction mixture was allowed to stir at rt overnight. The mixture was then treated with 1N HCl to slightly acidic, diluted with ethyl acetate (80 mL), washed with water (2×15 mL), dried with Na$_2$SO$_4$ and concentrated to give rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid as a white solid (35 mg, 73%). MS (ES$^+$) m/z [(M+H)$^+$]: 612

Example 210

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethoxy-phenyl)-amide

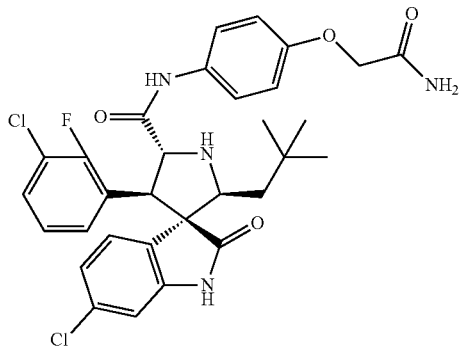

M. W. 613.51
$C_{31}H_{31}Cl_2FN_4O_4$

A mixture of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenoxy)-acetic acid prepared in Example 206 (23 mg, 0.037 mmol), N,N-diisopropylethylamine (33 mg, 0.258 mmol) and O-(7-azabenzotriazol-1-yl)-N,N,N',N'-tetramethyluronium hexafluorophosphate (HATU) (Chem-Impex, 24 mg, 0.062 mmol) in DMF (4 mL) was stirred for 20 min before NH₄Cl (6 mg, 0.099 mmol) was added. The mixture was stirred for 0.5 h and diluted with EtOAc (70 mL), washed with water (10 mL), brine (15 mL) and concentrated. The crude product was purified by flash chromatography (EtOAc/hexane, 25/75 to 95/5) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethoxy-phenyl)-amide as a white solid (9 mg, 40%). MS (ES⁺) m/z [(M+H)⁺]: 613

Example 211

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-carbamoyl-ethyl)-phenyl]-amide

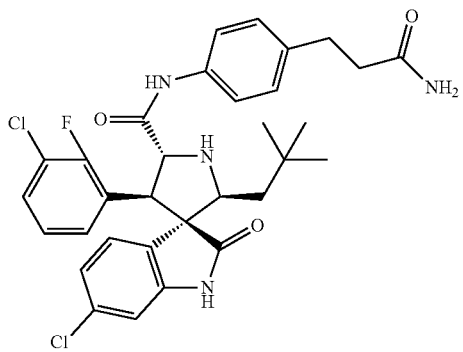

M. W. 611.53
$C_{32}H_{33}Cl_2FN_4O_3$

A mixture of rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-propionic acid prepared in Example 209 (31 mg, 0.051 mmol), N,N-diisopropylethylamine (45 mg, 0.344 mmol) and O-(7-azabenzotriazol-1-yl)-N,N,N',N'-tetramethyluronium hexafluorophosphate (HATU) (Chem-Impex, 32 mg, 0.084 mmol) in DMF (4 mL) was stirred for 20 min before NH₄Cl (9.5 mg, 0.176 mmol) was added. The mixture was stirred for 0.5 h and diluted with EtOAc (70 mL), washed with water (10 mL), brine (15 mL) and concentrated. The crude product was purified by flash chromatography (EtOAc/hexane, 25/75 to 100/0) to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-carbamoyl-ethyl)-phenyl]-amide as a white solid (9 mg, 40%). MS (ES⁺) m/z [(M+H)⁺]: 611

Example 212

Preparation of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzo[b]thiophene-2-carboxylic acid methyl ester

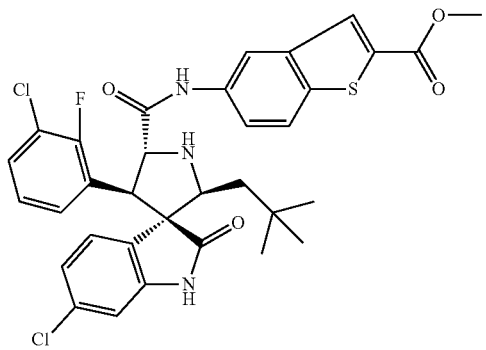

M. W. 654.58
$C_{33}H_{30}Cl_2FN_3O_4S$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (100 mg, 0.173 mmol), was reacted with diisopropylethylamine (111 mg, 0.86 mmol), diphenylphosphinic chloride (106 mg, 0.446 mmol), then reacted with 5-Amino-benzo[b]thiophene-2-carboxylic acid methyl ester (Maybridge, 41 mg, 0.190 mmol) to give rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzo[b]thiophene-2-carboxylic acid methyl ester (49 mg, 43%). MS (ES⁺) m/z [(M+H)⁺]: 654

Example 213

Preparation of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzo[b]thiophene-2-carboxylic acid

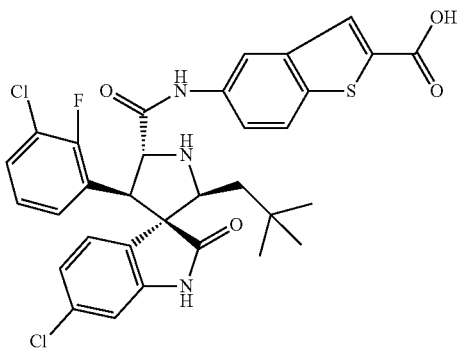

M. W. 640.57
$C_{32}H_{28}Cl_2FN_3O_4S$

To a solution of rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzo[b]thiophene-2-carboxylic acid methyl ester (42 mg, 0.065 mmol) in THF (3 mL) was added LiOH monohydrate (11 mg, 0.26 mmol) in water (2 mL) and the reaction mixture was allowed to stir at rt overnight. The mixture was then treated with 1N HCl to slightly acidic, diluted with ethyl acetate (80 mL), washed with water (2×15 mL), dried with $Na_2SO_4$ and concentrated to give rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzo[b]thiophene-2-carboxylic acid as a white solid (41 mg, 100%). MS (ES+) m/z [(M+H)+]: 640

Example 214

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-fluoro-5-methoxy-benzoic acid methyl ester

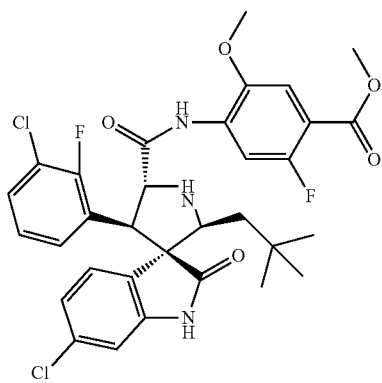

M. W. 646.51
$C_{32}H_{31}Cl_2F_2N_3O_5$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (150 mg, 0.259 mmol), was reacted with diisopropylethylamine (171 mg, 1.32 mmol), diphenylphosphinic chloride (155 mg, 0.656 mmol), then reacted with methyl 4-amino-2-fluoro-5-methoxybenzoate (Aldrich, 55 mg, 0.274 mmol,) to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid methyl ester (40 mg, 24%). MS (ES+) m/z [(M+H)+]: 646

Example 215

Preparation of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid

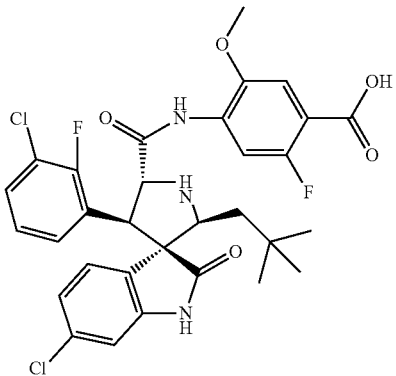

M. W. 632.48
$C_{31}H_{29}Cl_2F_2N_3O_5$

To a solution of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-fluoro-5-methoxy-benzoic acid methyl ester (36 mg, 0.056 mmol) in THF (3 mL) was added LiOH monohydrate (11 mg, 0.26 mmol) in water (2 ml) and the reaction mixture was allowed to stir at rt overnight. The mixture was then treated with 1N HCl to slightly acidic, diluted with ethyl acetate (80 mL), washed with water (2×15 mL), dried with $Na_2SO_4$ and concentrated to give rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-fluoro-5-methoxy-benzoic acid as a white solid (33 mg, 92%). MS (ES+) m/z [(M+H)+]: 632

Example 216

Preparation of intermediate methyl 3-(4-aminophenyl)propanoate

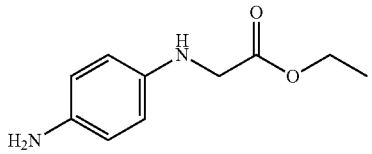

M. W. 194.24
$C_{10}H_{14}N_2O_2$

Step A To a solution of N-Boc-1,4-phenylene diamine (Aldrich, 1.00 g, 4.82 mmol) in $CH_2Cl_2$ (12 ml) were added N,N-diisopropylethylamine (1.26 g, 9.76 mmol) and ethyl bromoacetate (Aldrich, 813 mg, 4.87 mmol). The mixture was allowed to stir at rt overnight and then taken up in EtOAc (300 ml) and washed with sat. aqueous $Na_2CO_3$, water and brine. The organic layer was dried over $Na_2SO_4$ and concentrated in vacuo to give ethyl 2-(4-(tert-butoxycarbonylamino)phenylamino)acetate as a light brown oil (1.33 g, 94%).

Step B A solution of ethyl 2-(4-(tert-butoxycarbonylamino)phenylamino)acetate (772 mg, 2.62 mmol) in dichloromethane (14 mL) was treated with TFA (7 mL)) and the reaction mixture was stirred at 0° C. for 1.5 h. The resulting mixture was concentrated in vacuo and the residue was treated with EtOAc (200 ml) and washed with sat. aqueous $Na_2CO_3$, brine, dried over $Na_2SO_4$ and concentrated in vacuo to give ethyl 2-(4-aminophenylamino)acetate as a brown oil (483 mg, 94%).

Example 217

Preparation of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenylamino)-acetic acid ethyl ester

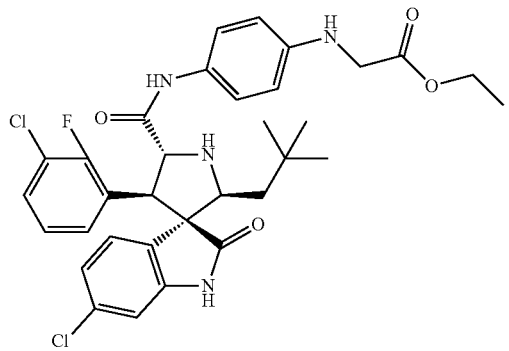

M. W. 641.58
$C_{33}H_{35}Cl_2FN_4O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (100 mg, 0.173 mmol), was reacted with diisopropylethylamine (89 mg, 0.690 mmol), diphenylphosphinic chloride (Alfa Aesar, 106 mg, 0.446 mmol), then reacted with ethyl 2-(4-aminophenylamino)acetate (35 mg, 0.181 mmol) to give rac-(4-{[(2'S,3'R,4'S,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenylamino)-acetic acid ethyl ester (33 mg, 29%). MS (ES$^+$) m/z [(M+H)$^+$]: 641

Example 218

Preparation of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenylamino)-acetic acid

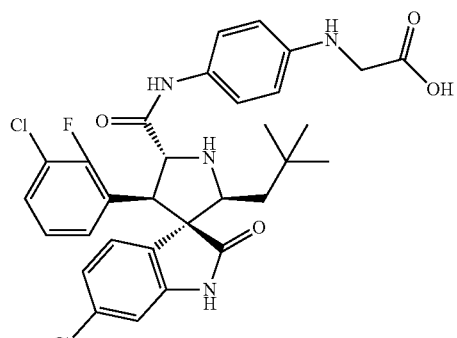

M. W. 613.51
$C_{31}H_{31}Cl_2FN_4O_4$

To a solution of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenylamino)-acetic acid ethyl ester (28 mg, 0.043 mmol) in THF (3 mL) was added LiOH monohydrate (9 mg, 0.199 mmol) in water (1.5 mL) and the reaction mixture was allowed to stir at rt overnight. The mixture was then treated with 1N HCl to slightly acidic, diluted with ethyl acetate (80 mL), washed with water (2×15 mL), dried with $Na_2SO_4$ and concentrated to give rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenylamino)-acetic acid as a white solid (25 mg, 97%). MS (ES$^+$) m/z [(M+H)$^+$]: 613

Example 219

Preparation of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-acetic acid ethyl ester

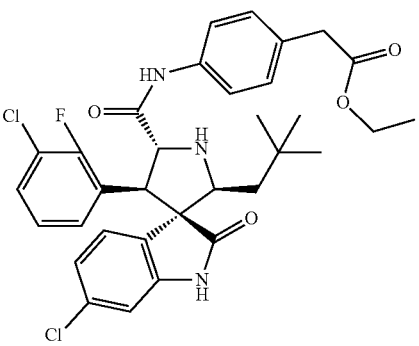

M. W. 626.56
$C_{33}H_{34}Cl_2FN_3O_4$

In a manner similar to the method described in Example 5, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 4 (120 mg, 0.257 mmol), was reacted with diisopropylethylamine (207 mg, 1.60 mmol), diphenylphosphinic chloride (146 mg, 0.618 mmol), then reacted with ethyl 2-(4-aminophenyl)acetate (56 mg, 0.315 mmol) to give rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-acetic acid ethyl ester (57 mg, 47%). MS (ES+) m/z [(M+H)+]: 626

Example 220

Preparation of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-acetic acid

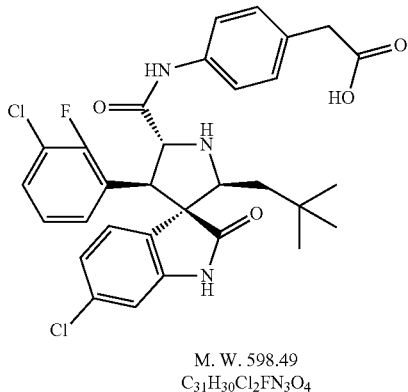

M. W. 598.49
C31H30Cl2FN3O4

To a solution of rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-acetic acid ethyl ester (52 mg, 0.083 mmol) in THF (3 mL) was added LiOH monohydrate (15 mg, 0.35 mmol) in water (1.5 mL) and the reaction mixture was allowed to stir at rt overnight. The mixture was then treated with 1N HCl to slightly acidic, diluted with ethyl acetate (80 mL), washed with water (2×15 mL), dried with Na2SO4 and concentrated to give rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-phenyl)-acetic acid as a white solid (47 mg, 95%). MS (ES+) m/z [(M+H)+]: 598.

Example 221

Preparation of chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-2-fluoro-5-methoxy-benzoic acid

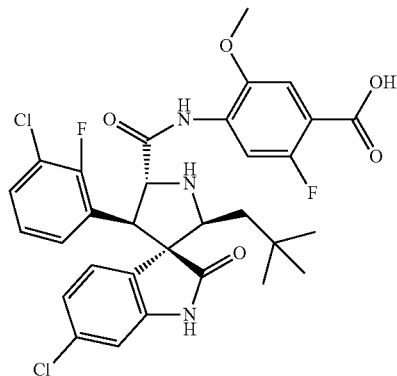

M. W. 632.48
C31H29Cl2F2N3O5

Rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid prepared in Example 215 was separated by SFC Chromatography (Waters/Thar Multi-Gram II, Kromasil 5-CelluCoat OD 3×25 cm., 35° C. at 100 bar, eluting with 40% methanol in carbon dioxide) to give chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid, MS (ES+) m/z [(M+H)+]: 632, and chiral 4-{[(2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid. MS (ES+) m/z [(M+H)+]: 632

Example 222

Preparation of chiral 3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid

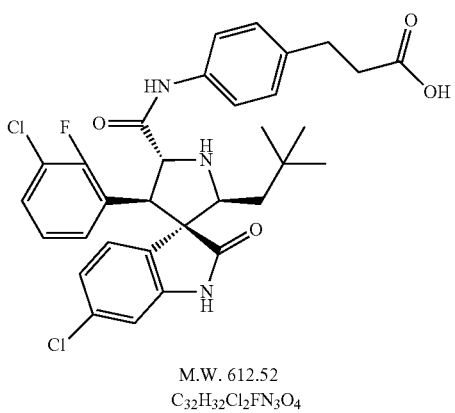

M.W. 612.52
C32H32Cl2FN3O4

Rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid was separated by SFC Chromatography (Waters/Thar Multi-Gram II, Kromasil 5-CelluCoat OD 3×25 cm., 35° C. at 100 bar, eluting with 40% methanol in carbon dioxide) to give chiral 3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid, MS (ES+) m/z [(M+H)+]: 612, and chiral 3-(4-{[(2'R,3'S,4'R,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid. MS (ES+) m/z [(M+H)+]: 612

Example 223

Preparation of chiral (2'S,3'R,4'S,5'R)-6-chloro-4'-(3-chloro-2-fluorophenyl)-N-(4-(cyanocarbamoyl)-2-methoxyphenyl)-2'-(2,2-dimethyl-propyl)-2-oxospiro[indoline-3,3'-pyrrolidine]-5'-carboxamide

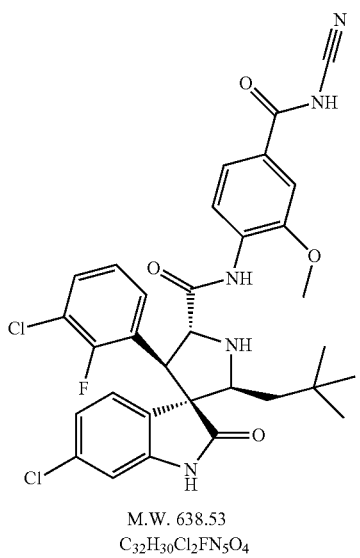

M.W. 638.53
$C_{32}H_{30}Cl_2FN_5O_4$

To a stirred solution of chiral (2'S,3'R,4'S,5'S)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid trifluoroacetic acid prepared in Example 136 (130 mg, 0.212 mmol) in DCM (4 ml), HATU (89 mg, 0.233 mmol) and DIPEA (30 mg, 0.233 mmol) were added successively and the mixture was stirred for 5 min. at rt. Then the cyamide (Aldrich, 60 mg) was added and the mixture was stirred at rt overnight. The mixture was loaded onto a silica gel column and eluted with 5% MeOH/$CH_2Cl_2$ to give a white solid. 46 mg. 42%. LCMS (ES+) m/z Calcd for $C_{32}H_{30}Cl_2FN_5O_4$ [(M+H)+]: 638, found: 638.

Example 224

Preparation of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide

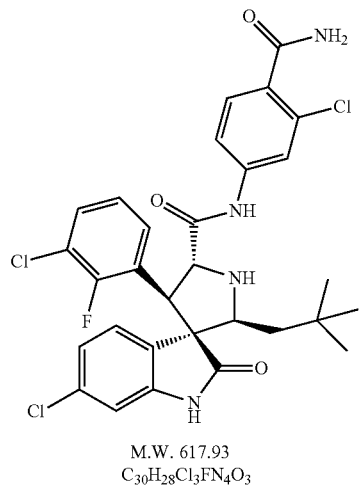

M.W. 617.93
$C_{30}H_{28}Cl_3FN_4O_3$

In a manner similar to the methods described in Example 16 and Example 22, rac-2-chloro-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester prepared in Example 24 (78 mg, 0.12 mmol) was hydrolyzed with aqueous NaOH in methanol and tetrahydrofuran at 78° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (50 mg, 66%), then rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (30 mg, 0.049 mmol) was reacted with EDCI (19 mg, 0.097 mmol), HOBt (13 mg, 0.097 mmol), triethylamine (9.8 mg, 0.097 mmol), and $NH_4Cl$ (26 mg, 0.49 mmol) at 80° C. to give rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide as a off white solid (Yield, 35 mg, 64%).

HRMS (ES+) m/z Calcd for $C_{30}H_{28}Cl_3FN_4O_3$+H [(M+H)+]: 617.1284, found: 617.1281.

Example 225

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53. Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

Activity data for some of the Example compounds expressed as $IC_{50}$:bsa:0.02% are as follows:

| Example Number | $IC_{50}$: bsa:0.02% |
|---|---|
| 5 | 0.016 |
| 6 | 0.011 |
| 7 | 0.014 |
| 8 | 0.007 |
| 9 | 0.004 |
| 10 | 0.013 |
| 11 | 0.013 |
| 12 | 0.006 |
| 13 | 0.019 |
| 14 | 0.022 |
| 15 | 0.013 |
| 16 | 0.01 |
| 17 | 0.004 |
| 20 | 0.007 |
| 21 | 0.019 |
| 22 | 0.011 |
| 23 | 0.005 |
| 25 | 0.02 |
| 26 | 0.006 |
| 27 | 0.017 |
| 30 | 0.014 |
| 31 | 0.017 |
| 32 | 0.017 |
| 33 | 0.013 |
| 34 | 0.018 |
| 35 | 0.005 |
| 36 | 0.018 |
| 37 | >10 |
| 42 | 0.014 |
| 44 | 0.01 |
| 48 | 0.016 |
| 49 | 0.013 |
| 50 | 0.006 |
| 51 | 0.02 |
| 52 | 0.012 |
| 53 | 0.011 |
| 54 | 0.007 |
| 55 | 0.013 |
| 56 | 0.019 |
| 58 | 0.023 |
| 59 | 0.014 |
| 60 | 0.005 |
| 64 | 0.034 |
| 65A | 0.009 |
| 65B | 0.006 |
| 66 | 0.014 |
| 67 | 0.01 |
| 72 | 0.022 |
| 73 | 0.011 |
| 74 | 0.006 |
| 75 | 0.02 |
| 76 | 0.011 |
| 77 | 0.005 |
| 79 | 0.013 |
| 83 | 0.034 |
| 84 | 0.015 |
| 88 | 0.013 |
| 89 | 0.013 |
| 94 | 0.012 |
| 98 | 0.018 |
| 99 | 0.018 |
| 104 | 0.012 |
| 105 | 0.013 |
| 106 | 0.009 |
| 107 | 0.017 |
| 108 | 0.009 |
| 109 | 0.011 |
| 110 | 0.011 |
| 111 | 0.005 |
| 112 | 0.015 |
| 113 | 0.009 |
| 114 | 0.012 |
| 115 | 0.006 |
| 116 | 0.015 |
| 117 | 0.007 |
| 118 | 0.011 |
| 119 | 0.007 |
| 122 | 0.013 |
| 123 | 0.006 |
| 124 | 0.015 |
| 125 | 0.007 |
| 126 | 0.029 |
| 127 | 0.012 |
| 129 | 0.01 |
| 130 | 0.011 |
| 131 | 0.014 |
| 134 | 0.005 |
| 137 | 0.005 |
| 138 | 0.013 |
| 143 | 0.015 |
| 144 | 0.019 |
| 146 | 0.014 |
| 147 | 0.011 |
| 148 | 0.005 |
| 150 | 0.015 |
| 151 | 0.013 |
| 152 | 0.011 |
| 153 | 0.008 |
| 154 | 0.004 |
| 155 | 0.013 |
| 157 | 0.01 |
| 159 | 0.014 |
| 160 | 0.005 |
| 161 | 0.004 |
| 162 | 0.019 |
| 164 | 0.018 |
| 166 | 0.025 |
| 167 | 0.01 |
| 169 | 0.011 |
| 170 | 0.007 |
| 171 | 0.006 |
| 175 | 0.04 |
| 176 | 0.018 |
| 177 | 0.021 |
| 178 | 0.015 |
| 179 | 0.039 |
| 181 | 0.006 |
| 182 | 0.017 |
| 183 | 0.007 |
| 185 | 0.016 |
| 187 | 0.015 |
| 188 | 0.008 |
| 192 | 0.007 |
| 194 | 0.055 |
| 195 | 0.015 |
| 196 | 0.05 |
| 197 | 0.051 |
| 198 | 0.012 |

-continued

| Example Number | IC$_{50}$: bsa:0.02% |
|---|---|
| 206 | 0.006 |
| 209 | 0.004 |
| 210 | 0.015 |
| 211 | 0.015 |
| 212 | 0.018 |
| 213 | 0.014 |
| 214 | 0.02 |
| 215 | 0.011 |
| 217 | 0.013 |
| 218 | 0.016 |
| 219 | 0.013 |
| 220 | 0.015 |
| 221 | 0.005 |
| 222 | 0.005 |
| 223 | 0.007 |

What is claimed:

1. A compound of the formula

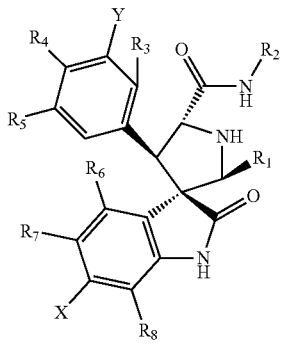

I wherein
X is selected from the group consisting of F, Cl, and Br,
Y is selected from the group consisting of F, Cl, and Br
$R_1$ is a substituted lower alkyl selected from:

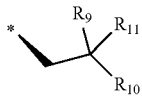

where $R_9$, $R_{10}$ are both methyl, or linked to form a cyclopropyl, cyclobutyl, cyclopentyl or cyclohexyl group, $R_{11}$ is $(CH_2)_q$—$R_{12}$ and $R_{12}$ is selected from hydrogen, hydroxyl, lower alkyl, lower alkoxy, lower cycloalkenyl, substituted cycloalkenyl, lower cycloalkyl, substituted cycloalkyl, aryl, substituted aryl, hetereoaryl, substituted heteroaryl, hetereocycle or substituted heterocycle, q is 0, 1 or 2, $R_2$ is selected from the group consisting of aryl, substituted aryl, heteroaryl and substituted heteroaryl, $R_3$, $R_4$, $R_5$ is selected from H or F with the proviso that at least two of $R_3$, $R_4$, $R_5$ are hydrogen $R_6$, $R_7$, $R_8$ is selected from H or F with the proviso that at least two of $R_6$, $R_7$, $R_8$ are hydrogen or a pharmaceutically acceptable salt or enantiomer thereof.

2. A compound of the formula

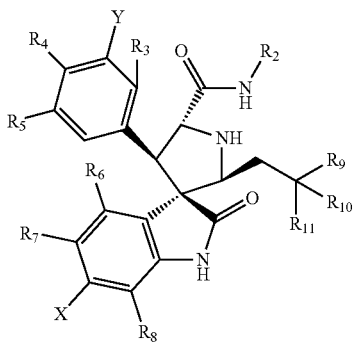

II wherein,

X is selected from F, Cl or Br;

Y is selected from F, Cl or Br;

$R_9$, $R_{10}$ are both methyl, or linked to form a cyclopropyl, cyclobutyl, cyclopentyl or cyclohexyl group;

$R_{11}$ is selected from hydrogen, methyl, ethyl, hydroxymethyl, 2-hydroxylethyl, hydroxycarbonyl, methoxycarbonyl, 2-methoxyethyl, isopropyl, cyclopropyl, 4-pyranyl, substituted 4-piperidinyl, substituted phenyl, substituted benzyl or substituted 2-furanyl;

$R_2$ is selected from aryl, substituted aryl, heteroaryl and substituted heteroaryl having the formulas

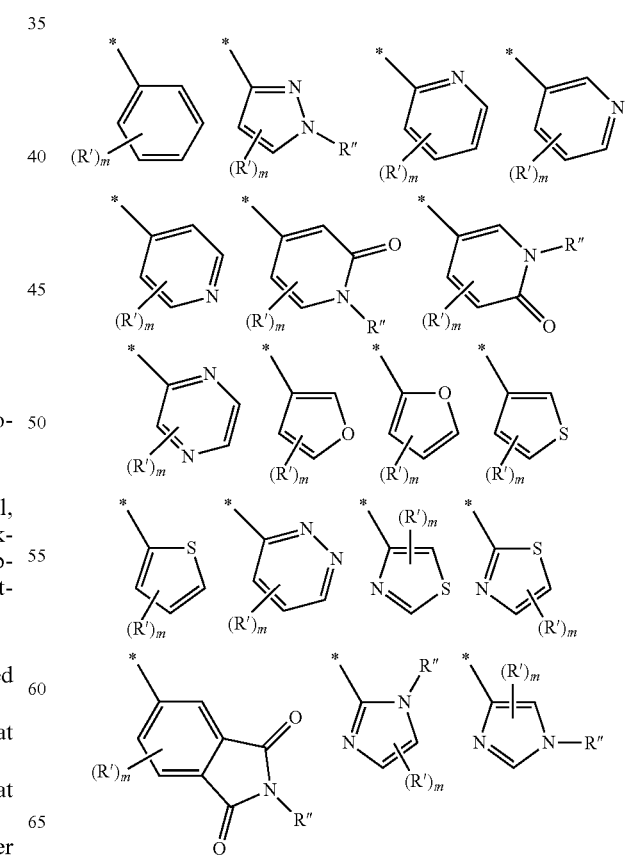

187

-continued

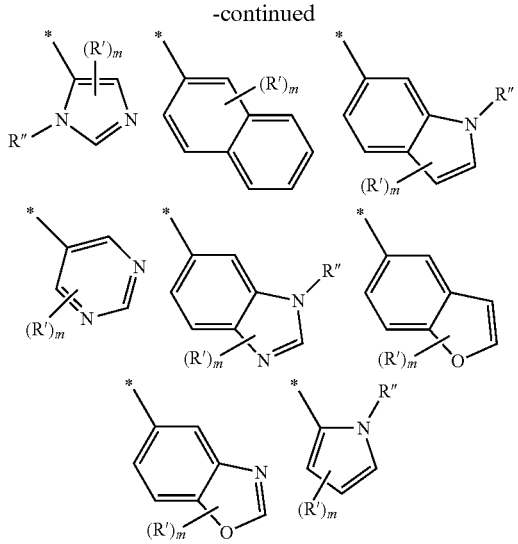

R' is selected from hydrogen, lower alkyl, lower-alkenyl, lower-alkynyl, dioxo-lower-alkylene (forming e.g. a benzodioxyl group), halogen, hydroxy, CN, CF$_3$, NH$_2$, N(H, lower-alkyl), N(lower-alkyl)$_2$, aminocarbonyl, lower-alkylaminocarbonyl, carboxy, NO$_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, NH$_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted aminosulfonyl and lower-alkyl which can optionally be substituted with halogen, hydroxy, NH$_2$, N(H, lower-alkyl) or N(lower-alkyl)$_2$ R" is one group selected from hydrogen, lower alkyl, lower-alkenyl, lower-alkynyl, hydroxy, CN, CF$_3$, aminocarbonyl, carboxy, lower-alkoxy, thio-lower-alkoxy, lower-alkylsufonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted aminosulfonyl and lower-alkyl which can optionally be substituted with halogen, hydroxy, NH$_2$, N(H, lower-alkyl) or N(lower-alkyl)$_2$ m=1-5

R$_3$, R$_4$, R$_5$ is selected from H or F with the proviso that at least two of R$_3$, R$_4$, R$_5$ are hydrogen; and

188

R$_6$, R$_7$, R$_8$ is selected from H or F with the proviso that at least two of R$_6$, R$_7$, R$_8$ are hydrogen or a pharmaceutically acceptable salt or enantiomer thereof.

3. The compound of claim 1 wherein

X is F, Cl or Br;

Y is F, Cl or Br;

R$_1$ is

R$_2$ is selected from aryl, substituted aryl, heteroaryl and substituted heteroaryl having the formulas

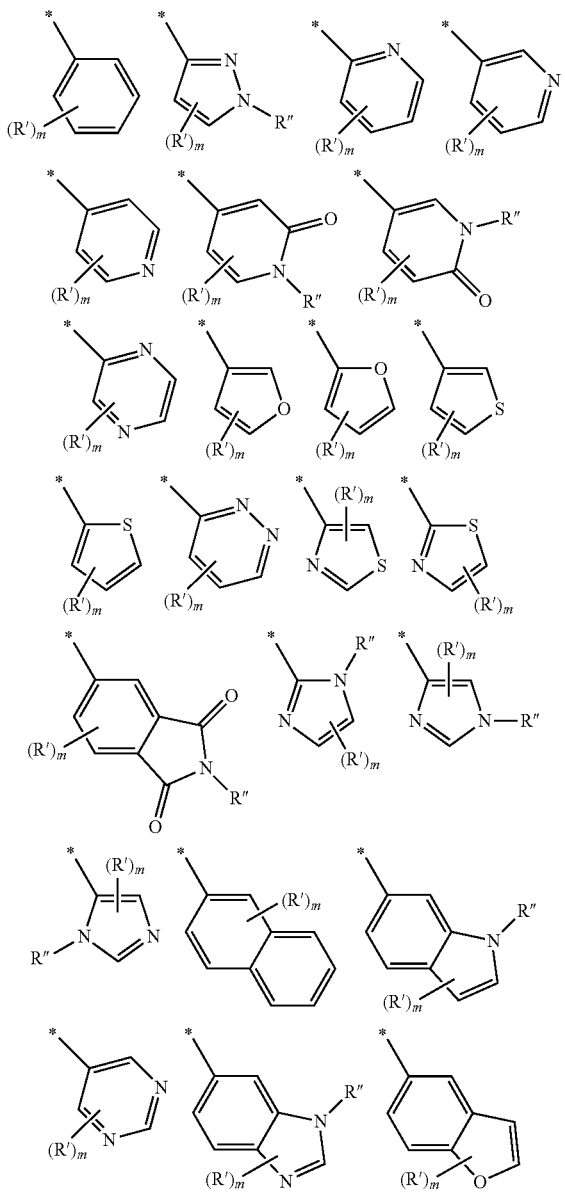

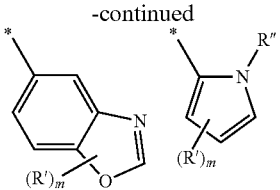

R' is selected from hydrogen, lower alkyl, lower-alkenyl, lower-alkynyl, dioxo-lower-alkylene, halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$ R" is one group selected from hydrogen, lower alkyl, lower-alkenyl, lower-alkynyl, hydroxy, CN, $CF_3$, aminocarbonyl, carboxy, lower-alkoxy, thio-lower-alkoxy, lower-alkylsufonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$ m=1-3

$R_3$, $R_4$, $R_5$ is selected from H or F with the proviso that at least two of $R_3$, $R_4$, $R_5$ are hydrogen; and $R_6$, $R_7$, $R_8$ is selected from H or F with the proviso that at least two of $R_6$, $R_7$, $R_8$ are hydrogen.

4. The compound of claim 1 wherein

X is F, Cl or Br;

Y is F, Cl or Br;

$R_1$ is

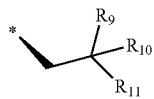

$R_9$, $R_{10}$, $R_{11}$ are methyl;

$R_2$ is selected from the group consisting of heteroaryl and substituted heteroaryl having the formulas

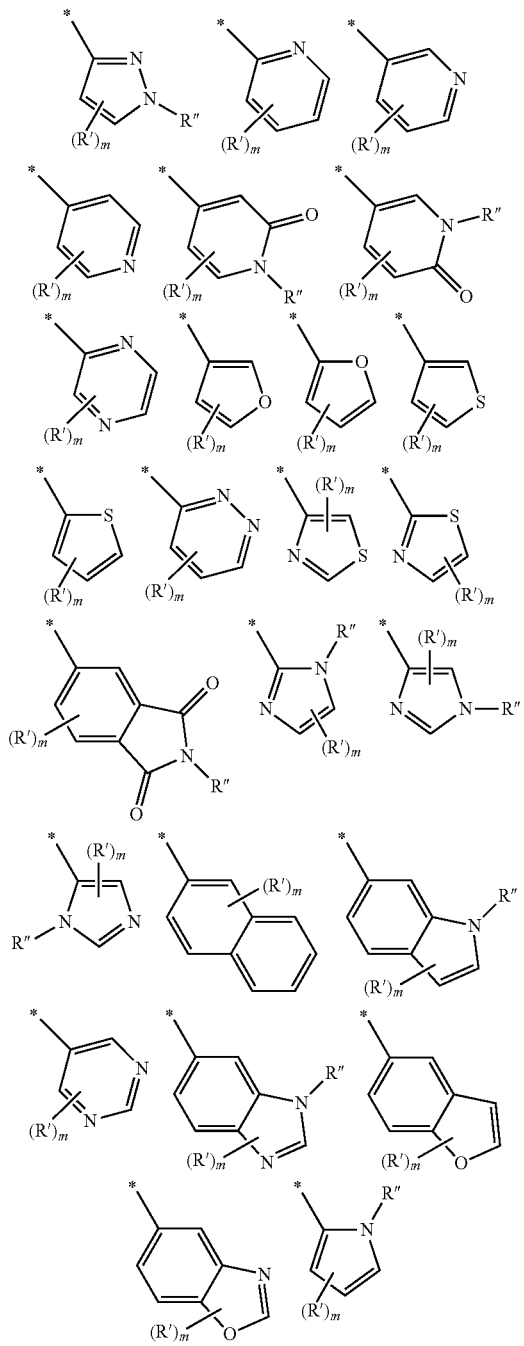

R' is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin- 1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl substituted with halogen, hydroxy, $NH_2$, N(H, lower-alkyl) or N(lower-alkyl)$_2$, R″ is selected from the group consisting of hydrogen, lower alkyl, lower-alkenyl, lower-alkynyl, hydroxy, CN, $CF_3$, aminocarbonyl, carboxy, lower-alkoxy, thio-lower-alkoxy, lower-alkylsufonyl, aminosulfonyl, lower-alkylcarbonyl, lower-alkoxycarbonyl, lower-alkoxycarbonyl, fluoro-lower-alkyl, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkylsubstituted with halogen, hydroxy, $NH_2$, N(H, lower-alkyl) or N(lower-alkyl)$_2$, m=1-3, $R_3$, $R_4$, $R_5$ is selected from H or F with the proviso that at least two of $R_3$, $R_4$, $R_5$ are hydrogen; and $R_6$, $R_7$, $R_8$ is selected from H or F with the proviso that at least two of $R_6$, $R_7$, $R_8$ are hydrogen and the pharmaceutically acceptable salts and esters and enantiomers thereof.

5. The compound of claim 1 wherein
X is F, Cl or Br;
Y is F, Cl or Br;
$R_1$ is

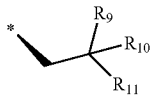

$R_9$, $R_{10}$, $R_{11}$ are methyl;
$R_2$ is a substituted phenyl of the formula

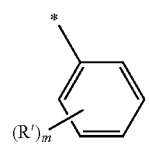

R' is selected from the group consisting of hydrogen, lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, lower-alkylaminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$, m=1-3, $R_3$, $R_4$, $R_5$ is selected from H or F with the proviso that at least two of $R_3$, $R_4$, $R_5$ are hydrogen;

$R_6$, $R_7$, $R_8$ is selected from H or F with the proviso that at least two of $R_6$, $R_7$, $R_8$ are hydrogen and the pharmaceutically acceptable salts and esters and enantiomers thereof.

6. The compound of claim 1 wherein
X is F, Cl or Br;
Y is F, Cl or Br;
$R_1$ is

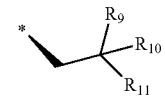

$R_9$, $R_{10}$, $R_{11}$ are methyl;
$R_2$ is a substituted phenyl of the formula

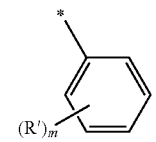

R' is selected from the group consisting of lower-alkenyl, lower-alkynyl, dioxo-lower-alkylene (forming e.g. a benzodioxyl group), hydroxy, CN, $CF_3$, aminocarbonyl, lower-alkylaminocarbonyl, carboxy, $NO_2$, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$, m=1-3, $R_3$, $R_4$, $R_5$ is selected from H or F with the proviso that at least two of $R_3$, $R_4$, $R_5$ are hydrogen;

$R_6$, $R_7$, $R_8$ is selected from H or F with the proviso that at least two of $R_6$, $R_7$, $R_8$ are hydrogen and the pharmaceutically acceptable salts and esters and enantiomers thereof.

7. A compound of formula I selected from the group consisting of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-acetyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-fluoro-phenyl)-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiophene-2-carboxylic acid methyl ester and rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid methyl ester.

8. A compound of claim 1 selected from the group consisting of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid, chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-chloro-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-methoxy-phenyl)-amide, rac-2-chloro-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-3-chloro-phenyl)-amide and rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (1-methyl-2-oxo-1,2-dihydro-pyridin-4-yl)-amide.

9. A compound of claim 1 selected from the group consisting of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1-propyl-1,2-dihydro-pyridin-4-yl)-amide, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]amino}-benzoic acid methyl ester, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid (3-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid p-tolylamide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-methanesulfonyl-phenyl)-amide, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid (2-oxo-1,2-dihydro-pyridin-4-yl)-amide and chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide.

10. A compound of claim 1 selected from the group consisting of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-acetyl)-phenyl]-amide, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid [1-(2-hydroxy-ethyl)-1 H-pyrazol-3-yl]-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester, rac-3-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid (3-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide and chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylcarbamoyl-phenyl)-amide.

11. A compound of claim 1 selected from the group consisting of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid p-tolylamide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-fluoro-4-methanesulfonyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-oxo-1,2-dihydro-pyridin-4-yl)-amide, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid [4-(2-hydroxy-acetyl)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid[1-(2-hydroxy-ethyl)-1H-pyrazol-3-yl]-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide and rac-(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide.

12. A compound of claim 1 selected from the group consisting of rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-phenyl)-amide, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-phenyl)-amide, acetic acid rac-3-[(2'S,3'R,4'S,5'R)-6-chloro-4'-(3-chloro-2-fluoro-phenyl)-5'-(4-cyano-phenylcarbamoyl)-2-oxo-1,2-dihydro-spiro[indole-3,3'-pyrrolidin]-2'-yl]-2, 2-dimethyl-propyl ester, rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(3-hydroxy-2,2-dimethyl-propyl)-2-oxo-1,2-dihydro-spiro[indole-3,3'-pyrrolidine]-5'-carboxylic acid (4-carbamoyl-phenyl)-amide, rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]amino}-3-methoxy-benzoic acid methyl ester and rac-4-{[(2'S,3'R,4'R,5'R)-6-chloro-4'-(3-chloro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid.

13. A compound of claim 1 selected from the group consisting of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid, chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-cyano-2-methoxy-phenyl)-amide, rac-(2'S,3'R,4'S,5'R)-6-chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (4-carbamoyl-2-methoxy-phenyl)-amide, rac-(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide, rac-(2'S,3'R,4'R, 5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-cyano-2-methoxy-phenyl)-amide, rac-(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide, rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-2-methoxy-phenyl)-amide and rac-(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide.

14. A compound of claim 1 selected from the group consisting of rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]-amino}-3-methoxy-benzoic acid methyl ester, rac-4-{[(2'S,3'R,4'S,5'R)-4'-(3-bromo-2-fluoro-phenyl)-6-chloro-2'-(2,2-dimethyl-propyl)-2-oxo-1,2-dihydro-spiro[indole-3,3'-pyrrolidine]-5'-carbonyl]-amino}-3-methoxy-benzoic acid, rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester, rac-4-{[(2'S,3'R,4'S,5'R)-6-bromo-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid, rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester, rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid, rac-4-{[(2'S,3'R,4'R,5'R)-6-chloro-4'-(3-chloro-4-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid methyl ester, rac-4-{[(2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carbonyl]-amino}-3-methoxy-benzoic acid , rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-ethoxy-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-ethoxy-phenyl)-amide and rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide.

15. A compound of claim 1 selected from the group consisting of chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-hydroxy-ethoxy)-2-methoxy-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-nitro-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-amino-2-methoxy-phenyl)-amide, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid (4-acetylamino-2-methoxy-phenyl)-amide, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid (4-acetyl-2-methoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-morpholin-4-yl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2,6-dimethyl-morpholin-4-yl)-2-methoxy-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-trifluoromethoxy-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid phenylamide and chiral (2'S,3'R,4'R,5'R)-6-chloro-4'-(3-chloro-5-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide.

16. A compound of claim 1 selected from the group consisting of rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid methyl ester, rac-3-butoxy-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzoic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-butoxy-4-carbamoyl-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-methoxy-4-tetrazol-1-yl-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(morpholine-4-sulfonyl)-phenyl]-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-methanesulfonylamino-2-methoxy-phenyl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(tetrahydro-pyran-4-yloxy)-phenyl]-amide, chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-phenyl)-acetic acid tert-butyl ester, chiral (4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methoxy-phenyl)-acetic acid, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethyl-2-methoxy-phenyl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (3-methoxy-pyridin-4-yl)-amide and rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-dimethylamino-2-methoxy-phenyl)-amide.

17. A compound of claim 1 selected from the group consisting of rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methylamino-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-3-methylamino-benzoic acid, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [2-methoxy-4-(2-methylsulfanyl-ethoxy)-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfonyl-ethoxy)-2-methoxy-phenyl]-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-methanesulfinyl-ethoxy)-2-methoxy-phenyl]-amide, rac-(2'S,3'R,4'S,5'R)-6-chloro-4'-(3-chloro-2-fluoro-phenyl)-2'-(2,2-dimethyl-propyl)-7-fluoro-2-oxo-1 ,2-dihydro-spiro[indole-3,3'-pyrrolidine]-5'-carboxylic acid (4-cyano-phenyl)-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-phenyl)-amide, rac-(2'S,3' R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-cyano-2-methoxy-phenyl)-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid (4-carbamoyl-2-methoxy-phenyl)-amide, rac-(2'S,3'R,4'S,5'R)-6-chloro-4'-(3-chloro-2-fluoro-phenyl)-2'-(2,2-dimethyl-propyl)-7-fluoro-2-oxo-1,2-dihydro-spiro[indole-3,3'-pyrrolidine]-5'-carboxylic acid [4-(2-hydroxy-ethoxy)-2-methoxy-phenyl]-amide and chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(3-methanesulfonyl-propoxy)-2-methoxy-phenyl]-amide.

18. A compound of claim 1 selected from the group consisting of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-cyano-pyridin-3-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (6-carbamoyl-pyridin-3-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-cyano-pyrimidin-5-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (2-carbamoyl-pyrimidin-5-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-thiophen-2-yl)-amide, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-thiophen-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [6-(2-hydroxy-ethoxy)-4-methoxy-pyridin-3-yl]-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-1-methyl-1H-pyrrole-2-carboxylic acid tert-butyl ester, rac-(2'S,3'R,4'S,5'R)-6-chloro-4'-(3-chloro-2-fluoro-phenyl)-2'-(2, 2-dimethyl-propyl)-2-oxo-1,2-dihydro-spiro[indole-3,3'-pyrrolidine]-5'-carboxylic acid (1-methyl-1H-pyrrol-2-yl)-amide and rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid ethyl ester.

19. A compound of claim 1 selected from the group consisting of rac-2-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-thiazole-4-carboxylic acid, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-thiazol-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-cyano-pyridin-2-yl)-amide, rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (5-carbamoyl-pyridin-2-yl)-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-furan-2-carboxylic acid methyl ester, acetic acid chiral 2-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-methoxy-phenoxy)-ethyl ester, chiral (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid[4-(2-hydroxy-ethoxy)-3-methoxy-phenyl]-amide, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbony]-amino}-phenoxy)-acetic acid methyl ester, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenoxy)-acetic acid, rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbony]-amino}-phenyl)-propionic acid methyl ester, rac-3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid and rac-(2'S,3'R,4'S,5' R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoylmethoxy-phenyl)-amide.

20. A compound of claim 1 selected from the group consisting of rac-(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid [4-(2-carbamoyl-ethyl)-phenyl]-amide, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzo[b]thiophene-2-carboxylic acid methyl ester, rac-5-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-benzo[b]thiophene-2-carboxylic acid, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid methyl ester, rac-4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbony]-amino}-2-fluoro-5-methoxy-benzoic acid, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenylamino)-acetic acid ethyl ester, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbony]-amino}-phenylamino)-acetic acid, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-acetic acid ethyl ester, rac-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-acetic acid, chiral 4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-2-fluoro-5-methoxy-benzoic acid , chiral 3-(4-{[(2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-phenyl)-propionic acid and chiral (2'S,3R,4'S,5'R)-6-chloro-4'-(3-chloro-2-fluorophenyl)-N-(4-(cyanocarbamoyl)-2-methoxyphenyl)-2'-(2,2-dimethyl-propyl)-2-oxospiro[indoline-3,3'-pyrrolidine]-5'-carboxamide.

21. A pharmaceutical composition comprising a compound of claim 1, or a pharmaceutically acceptable salt or enantiomer thereof, as an active ingredient together with a pharmaceutically acceptable carrier or excipient.

22. The compound: chiral (2'S, 3'R, 4'S, 5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (4-carbamoyl-2-methoxy-phenyl)-amide.

* * * * *